US 12,426,914 B2

(12) United States Patent
Hatta et al.

(10) Patent No.: US 12,426,914 B2
(45) Date of Patent: *Sep. 30, 2025

(54) MEDICAL DEVICE AND TREATMENT METHOD

(71) Applicant: TERUMO KABUSHIKI KAISHA, Tokyo (JP)

(72) Inventors: Tomonori Hatta, San Jose, CA (US); Junichi Kobayashi, Cupertino, CA (US); Taiga Nakano, Cupertino, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 459 days.

This patent is subject to a terminal disclaimer.

(21) Appl. No.: 17/364,121

(22) Filed: Jun. 30, 2021

(65) Prior Publication Data

US 2021/0322051 A1 Oct. 21, 2021

Related U.S. Application Data

(63) Continuation of application No. 15/180,557, filed on Jun. 13, 2016, now Pat. No. 11,096,715, which is a
(Continued)

(30) Foreign Application Priority Data

Nov. 4, 2014 (JP) ................. 2014-224105

(51) Int. Cl.
*A61B 17/3207* (2006.01)
*A61F 2/01* (2006.01)
*A61B 17/221* (2006.01)

(52) U.S. Cl.
CPC ............. *A61B 17/320725* (2013.01); *A61B 17/320758* (2013.01); *A61F 2/013* (2013.01);
(Continued)

(58) Field of Classification Search
CPC .... A61B 17/320725; A61B 17/320758; A61B 17/221; A61B 2017/2212;
(Continued)

(56) References Cited

U.S. PATENT DOCUMENTS

| 4,895,560 A | 1/1990 | Papantonakos |
| 5,030,201 A | 7/1991 | Palestrant |

(Continued)

FOREIGN PATENT DOCUMENTS

| JP | H10151136 A | 6/1998 |
| JP | 2003504090 A | 2/2003 |

(Continued)

OTHER PUBLICATIONS

U.S. Appl. No. 15/586,844, filed May 4, 2017, naming Tomonori Hatta, Junichi Kobayashi and Taiga Nakano as inventors.
(Continued)

*Primary Examiner* — Ashley L Fishback
*Assistant Examiner* — Chima U Igboko
(74) *Attorney, Agent, or Firm* — Buchanan Ingersoll & Rooney PC

(57) ABSTRACT

A treatment method and medical device are disclosed for cutting a substance inside a body lumen. The medical device for cutting substances inside a body lumen including a rotatable tubular drive shaft; an expanding part connected to a distal side of the tubular drive shaft; a cutting part covering the expanding part; and an elongated tube extending through the tubular drive shaft and connected to the expanding part, wherein a distal end of the expanding part is placed distal to a distal end of the cutting part.

21 Claims, 34 Drawing Sheets

Related U.S. Application Data continuation-in-part of application No. 14/931,335, filed on Nov. 3, 2015, now Pat. No. 11,083,485.

(60) Provisional application No. 62/104,487, filed on Jan. 16, 2015.

(52) U.S. Cl.
CPC ..... *A61B 17/221* (2013.01); *A61B 2017/2212* (2013.01); *A61B 2017/320716* (2013.01); *A61B 2017/320733* (2013.01); *A61F 2002/016* (2013.01); *A61F 2002/018* (2013.01)

(58) Field of Classification Search
CPC ....... A61B 2017/320716; A61B 2017/320733; A61F 2/013; A61F 2002/016; A61F 2002/018
See application file for complete search history.

(56) References Cited

U.S. PATENT DOCUMENTS

| | | | |
|---|---|---|---|
| 5,211,651 A | 5/1993 | Reger et al. | |
| 5,314,438 A * | 5/1994 | Shturman | A61M 25/01 606/159 |
| 5,391,144 A | 2/1995 | Sakurai et al. | |
| 5,490,859 A | 2/1996 | Mische et al. | |
| 5,571,122 A | 11/1996 | Kelly et al. | |
| 5,662,671 A | 9/1997 | Barbut et al. | |
| 5,792,157 A | 8/1998 | Mische et al. | |
| 5,972,019 A | 10/1999 | Engelson et al. | |
| 6,096,054 A | 8/2000 | Wyzgala et al. | |
| 6,656,203 B2 | 12/2003 | Roth et al. | |
| 6,818,001 B2 | 11/2004 | Wulfman et al. | |
| 7,150,756 B2 | 12/2006 | Levinson et al. | |
| 7,662,163 B2 | 2/2010 | Grayzel et al. | |
| 11,096,715 B2 * | 8/2021 | Hatta | A61B 17/320725 |
| 2002/0010487 A1 | 1/2002 | Evans et al. | |
| 2002/0151906 A1 | 10/2002 | Demarais et al. | |
| 2002/0169472 A1 | 11/2002 | Douk et al. | |
| 2004/0158270 A1 | 8/2004 | Wyzgala et al. | |
| 2005/0197597 A1 | 9/2005 | Douk | |
| 2009/0171293 A1 | 7/2009 | Yang et al. | |
| 2010/0130850 A1 | 5/2010 | Pakter | |
| 2011/0196348 A1 * | 8/2011 | Brandeis | A61B 17/12109 606/1 |
| 2011/0306867 A1 | 12/2011 | Gopinathan et al. | |
| 2014/0107481 A1 | 4/2014 | Wulfman | |
| 2014/0275777 A1 * | 9/2014 | Gunday | A61B 17/320725 600/109 |
| 2014/0309672 A1 | 10/2014 | Labropoulos et al. | |
| 2016/0120565 A1 | 5/2016 | Kobayashi et al. | |
| 2016/0120568 A1 | 5/2016 | Kobayashi et al. | |
| 2016/0120569 A1 | 5/2016 | Kobayashi et al. | |
| 2016/0120570 A1 | 5/2016 | Kobayashi et al. | |
| 2016/0278805 A1 | 9/2016 | Hatta et al. | |
| 2017/0258488 A1 | 9/2017 | Hatta et al. | |

FOREIGN PATENT DOCUMENTS

| | | |
|---|---|---|
| WO | 9944513 A2 | 9/1999 |
| WO | 0158382 A2 | 8/2001 |
| WO | 2005030063 A1 | 4/2005 |
| WO | 2014152314 A1 | 9/2014 |
| WO | 2015029041 A1 | 3/2015 |

OTHER PUBLICATIONS

U.S. Appl. No. 14/931,335, filed Nov. 3, 2015, naming Tomonori Hatta, Junichi Kobayashi and Taiga Nakano as inventors.
U.S. Appl. No. 14/931,453, filed Nov. 3, 2015, naming Tomonori Hatta, Junichi Kobayashi and Taiga Nakano as inventors.
U.S. Appl. No. 14/931,515, filed Nov. 3, 2015, naming Tomonori Hatta, Junichi Kobayashi and Taiga Nakano as inventors.
U.S. Appl. No. 14/931,623, filed Nov. 3, 2015, naming Tomonori Hatta, Junichi Kobayashi and Taiga Nakano as inventors.
Office Action (Notice of Reasons for Refusal) issued on Jul. 6, 2020, by the Japanese Patent Office in corresponding Japanese Patent Application No. 2019-167237 and an English Translation of the Office Action. (6 pages).
International Search Report (PCT/ISA/210) issued on Sep. 1, 2015, by the Japanese Patent Office as the International Searching Authority for International Application No. PCT/JP2015/065888 (with English translation).
Written Opinion (PCT/ISA/237) issued on Sep. 1, 2015, by the Japanese Patent Office as the International Searching Authority for International Application No. PCT/JP2015/065888 (with English translation).

* cited by examiner

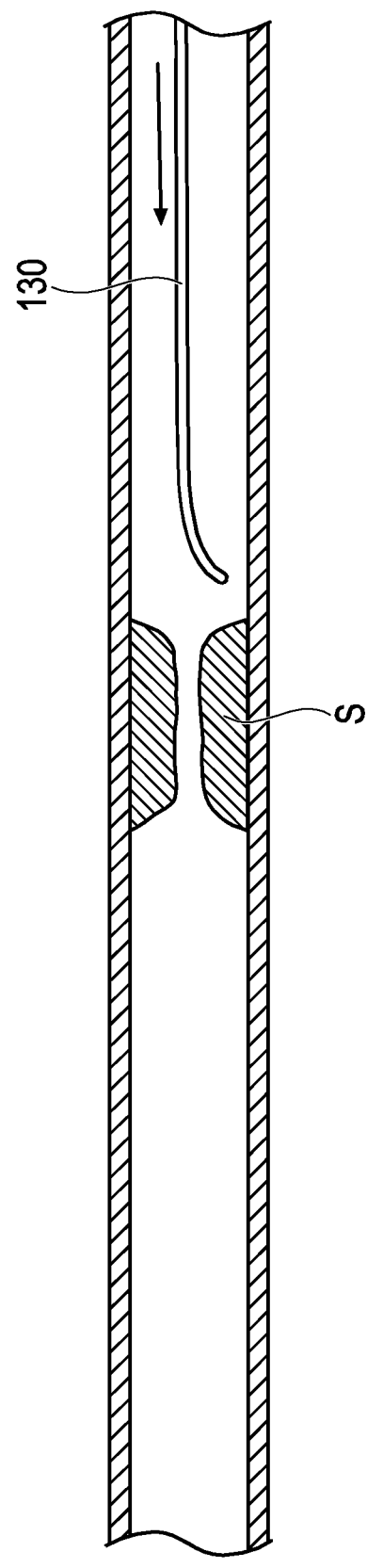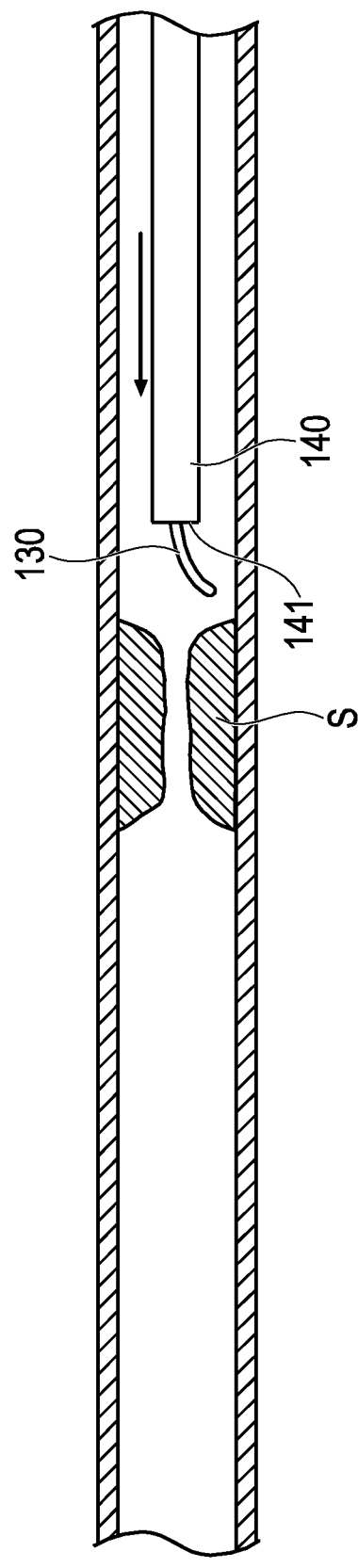

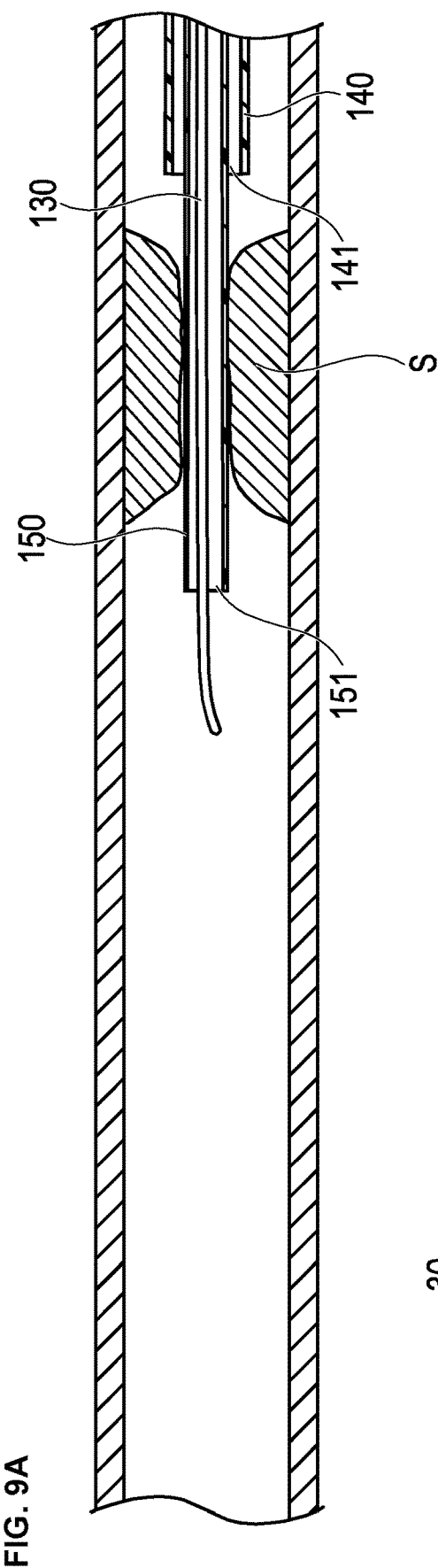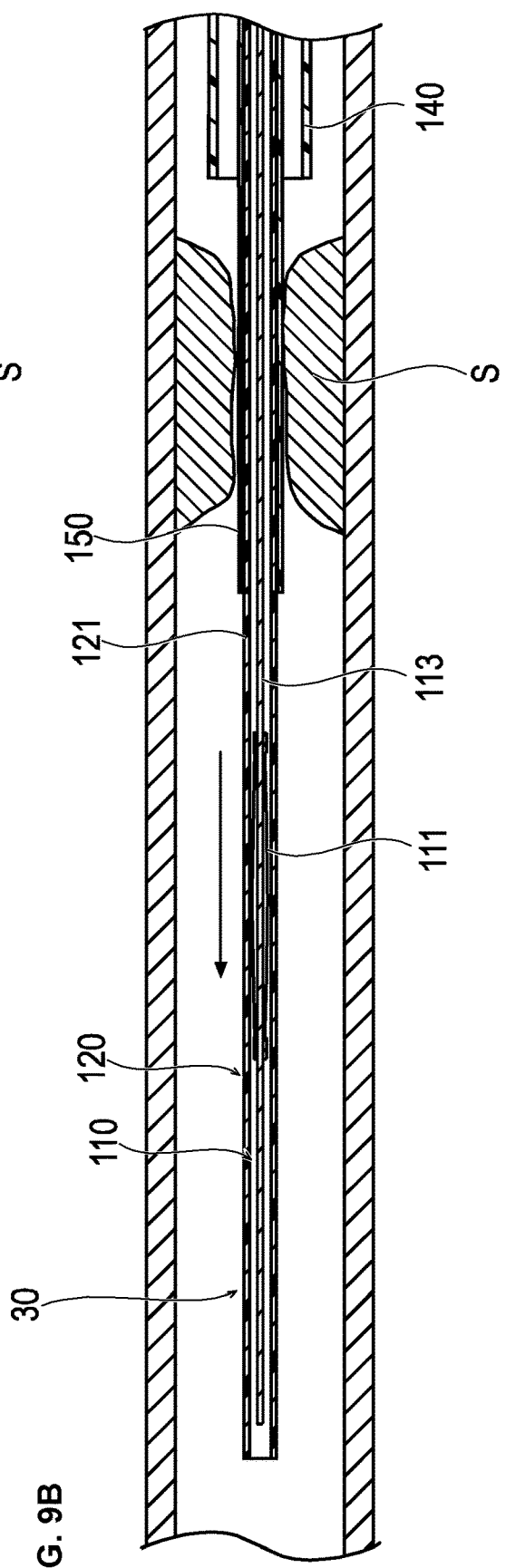

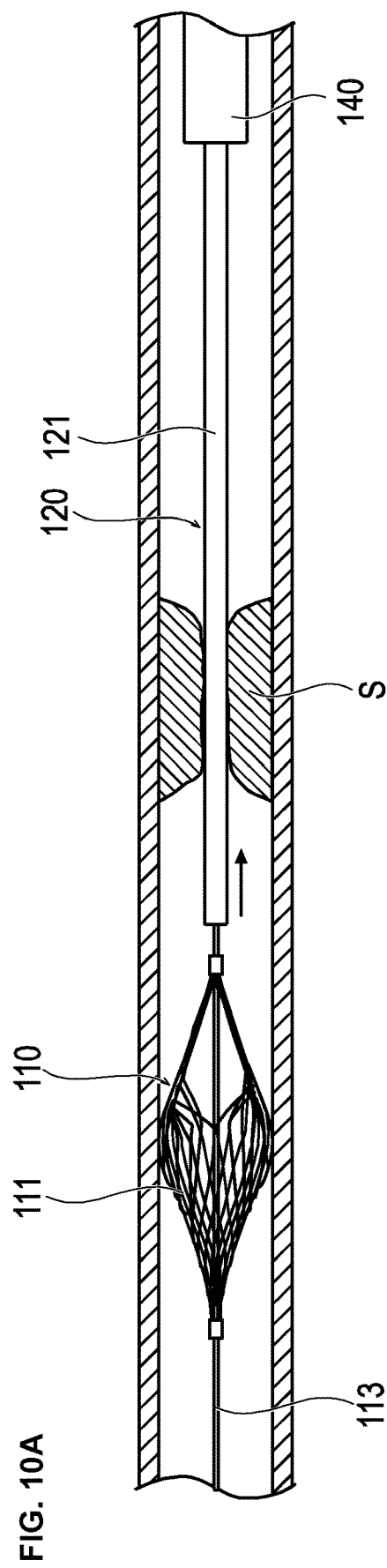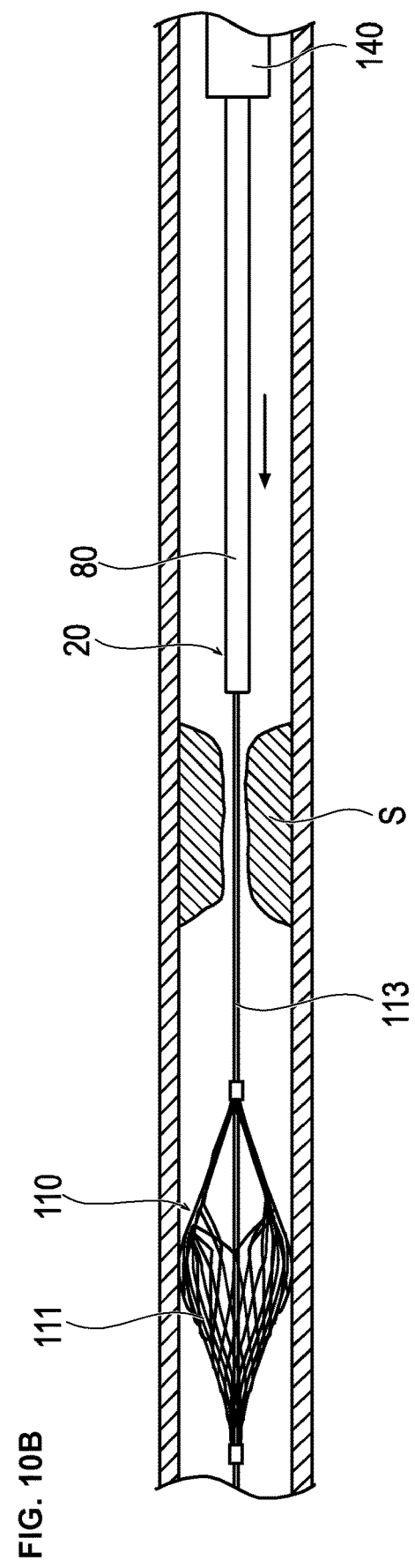

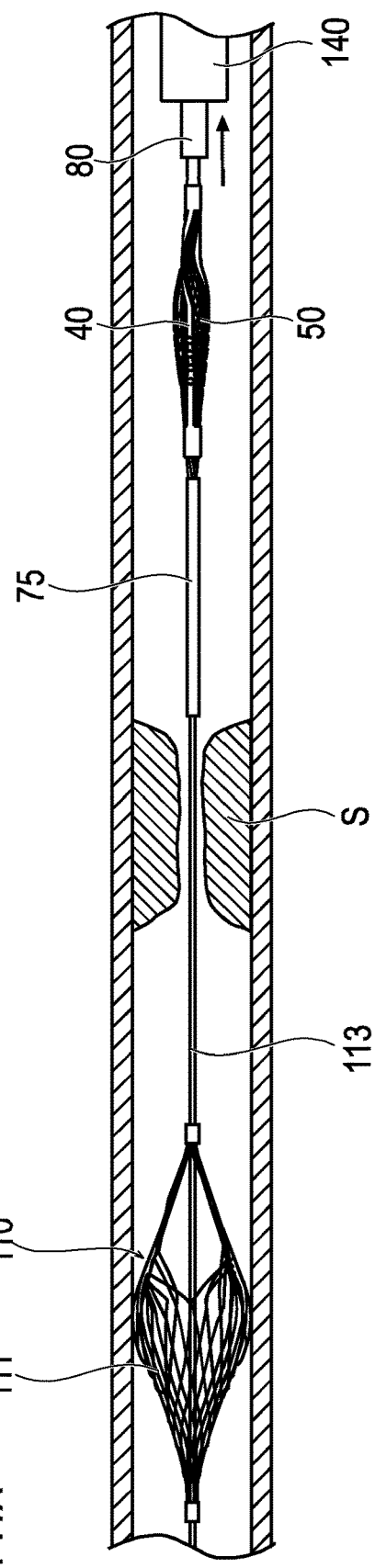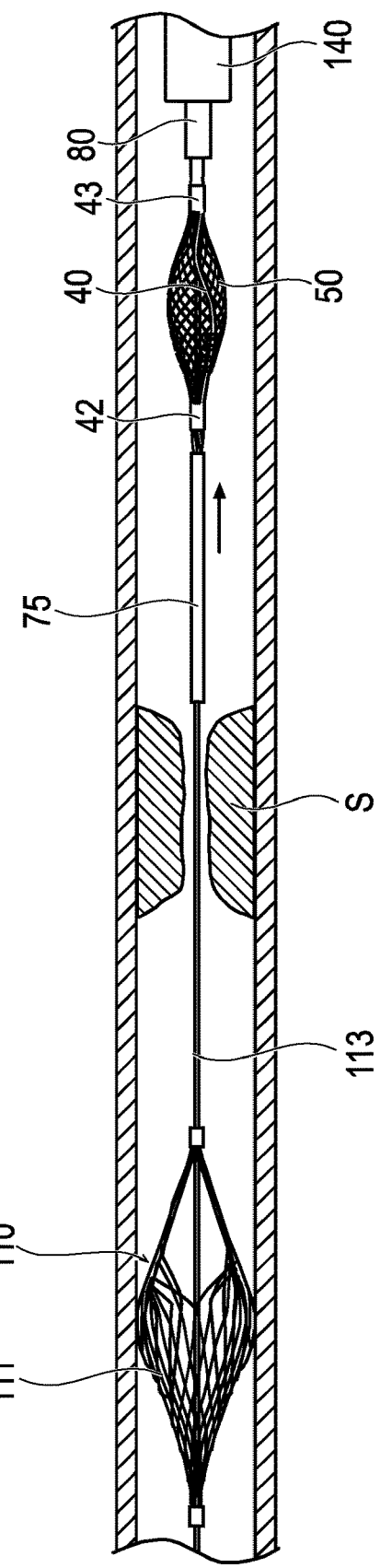

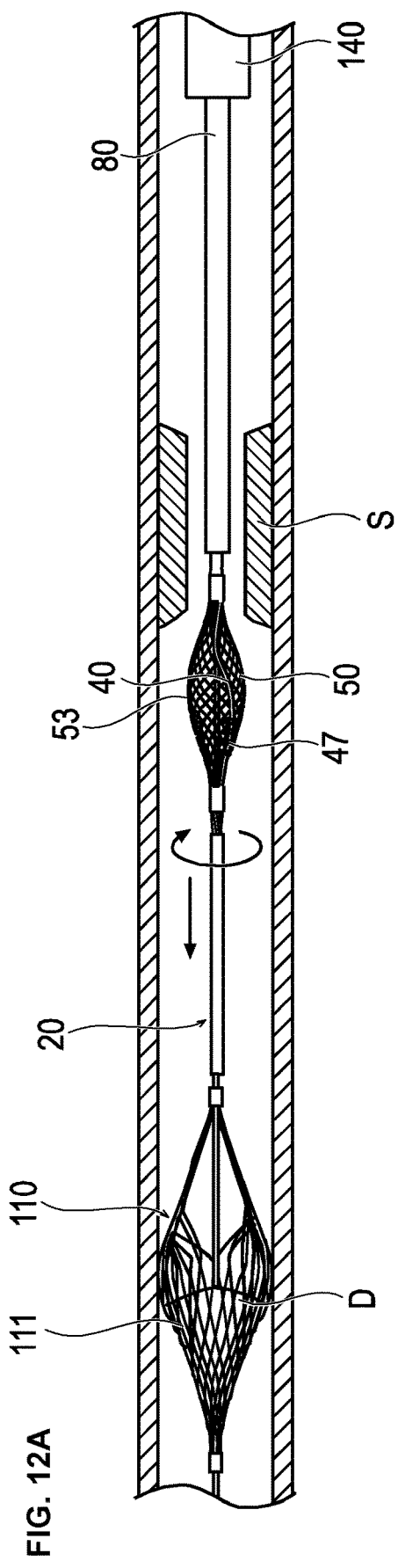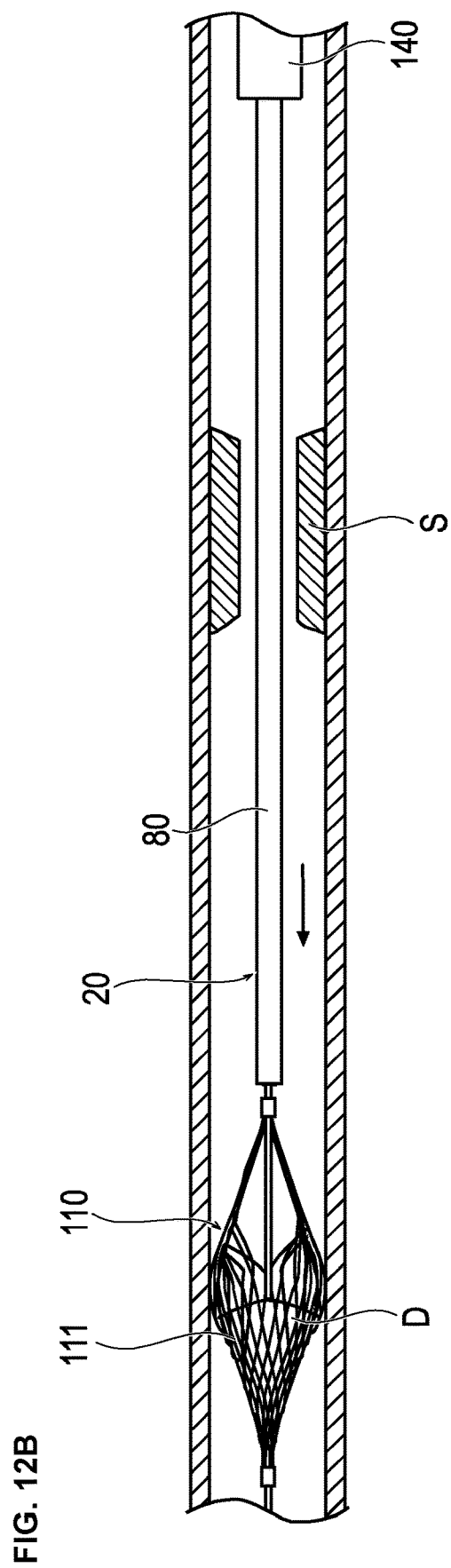
FIG. 12A
FIG. 12B

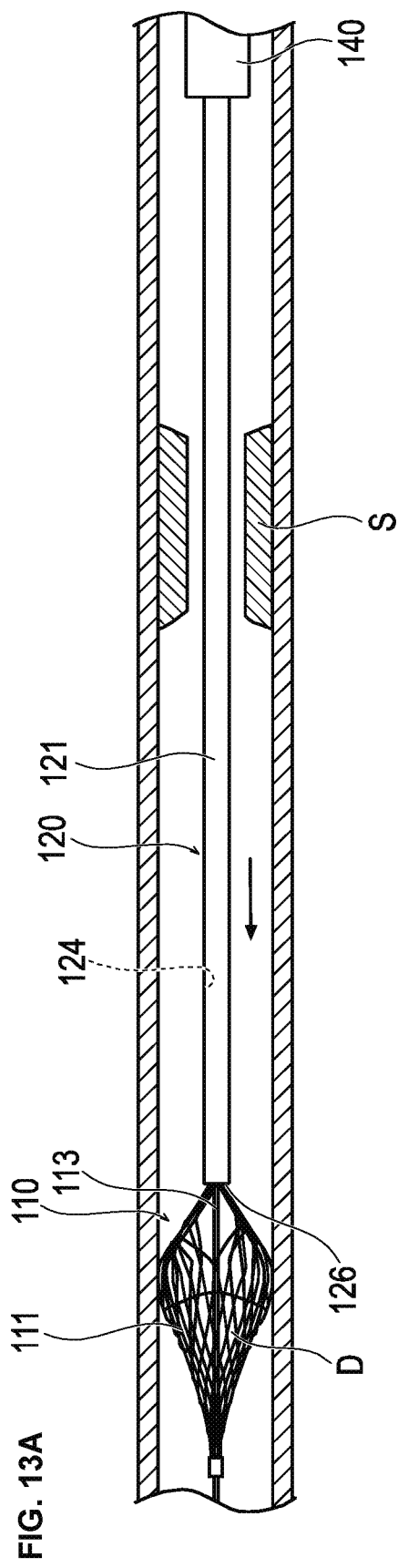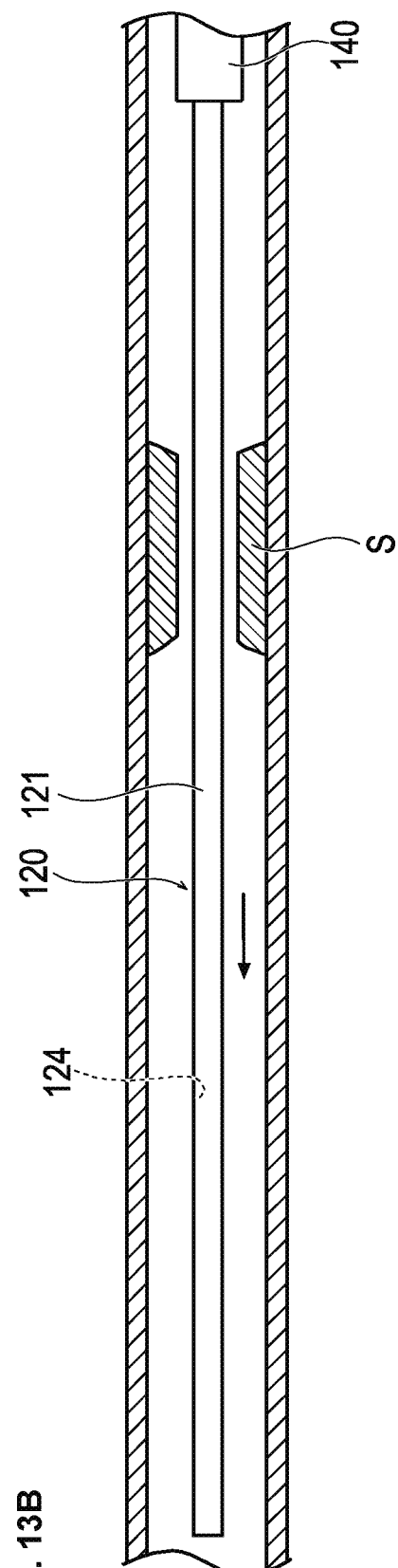

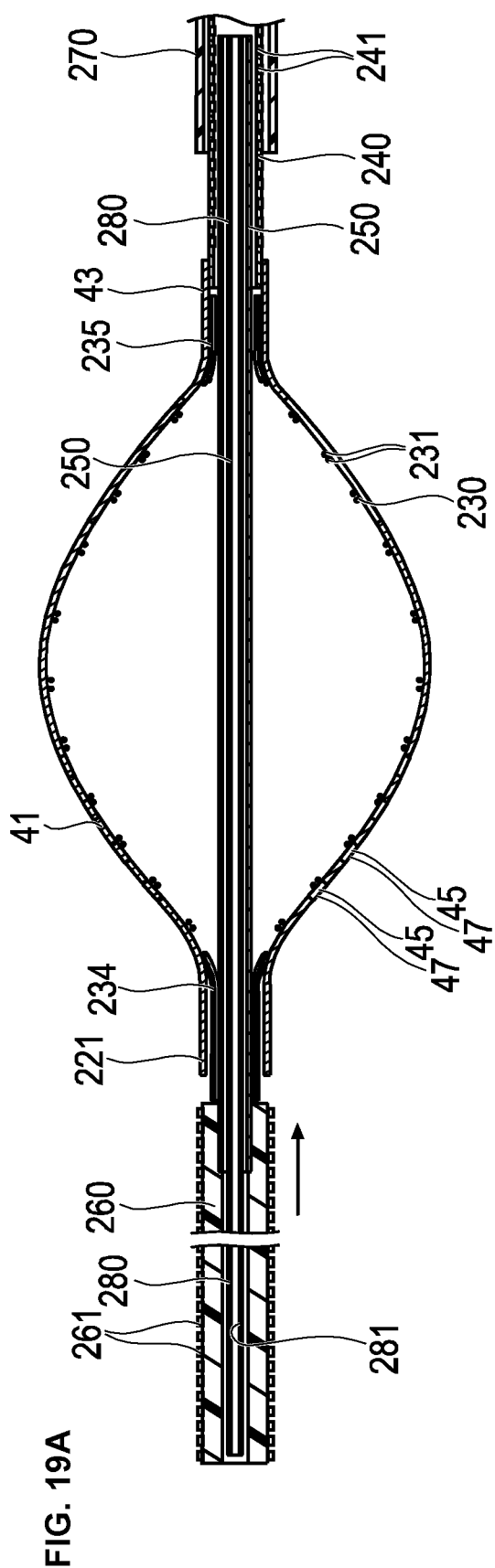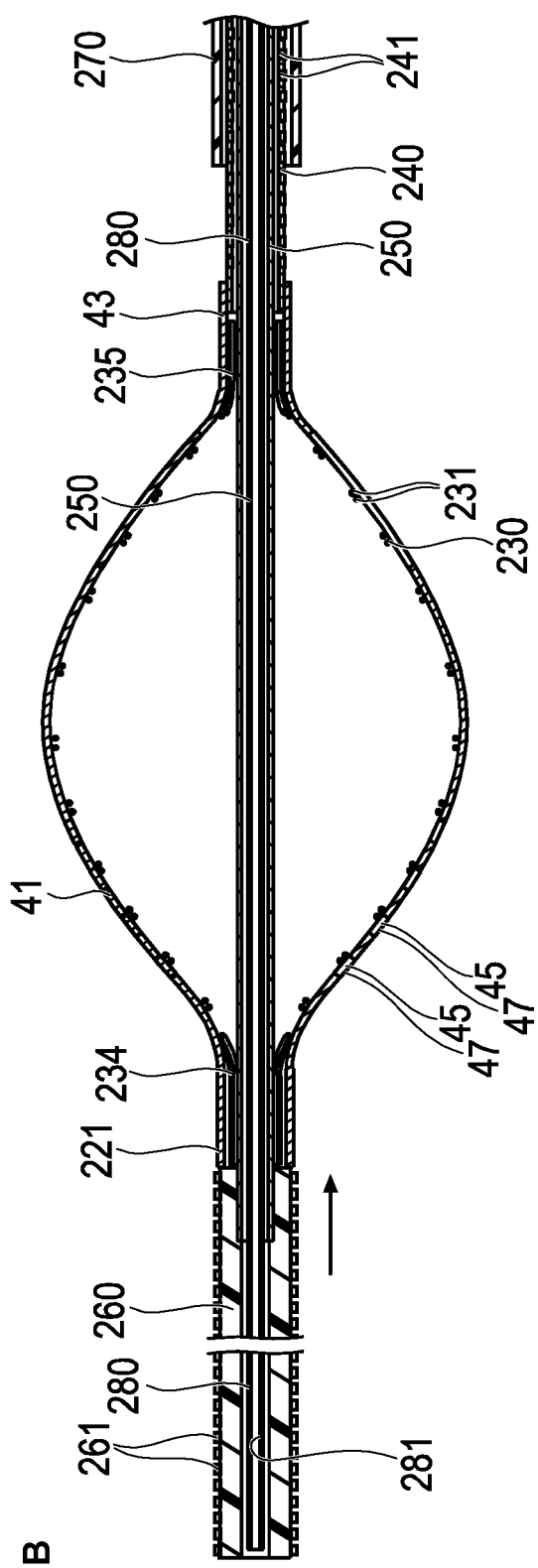
FIG. 19A
FIG. 19B

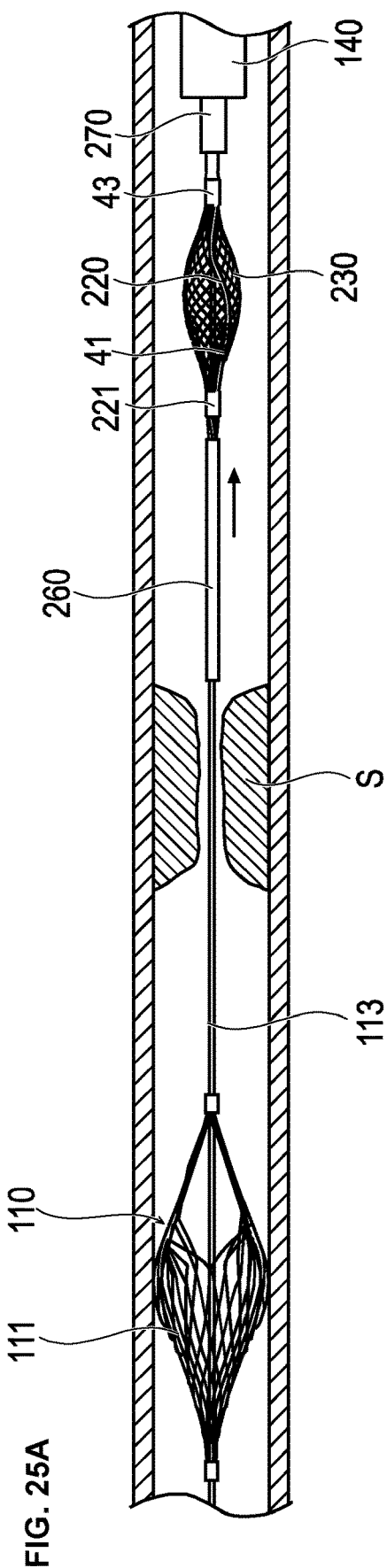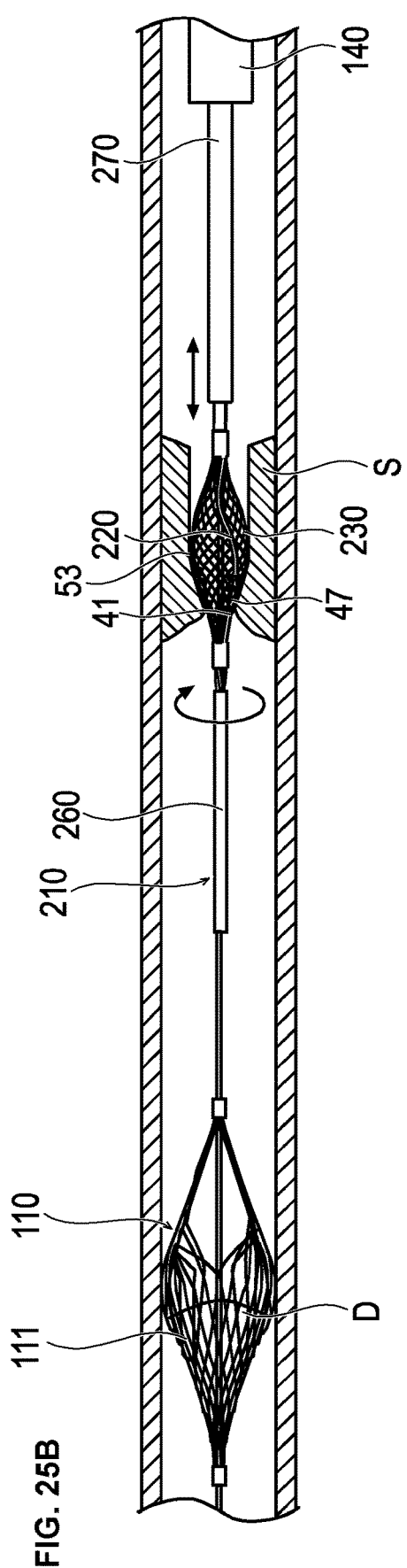

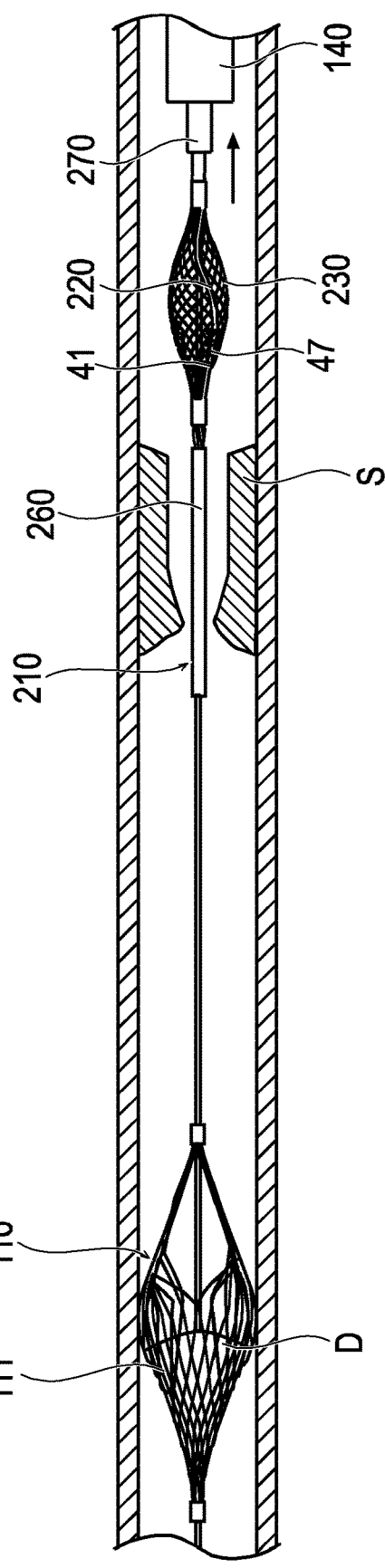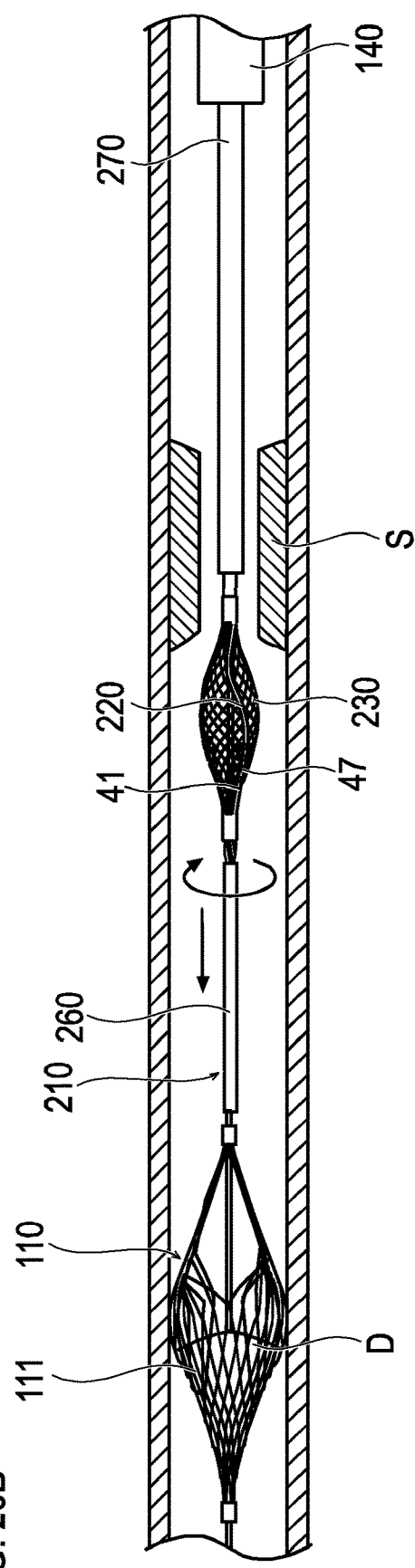
FIG. 26A
FIG. 26B

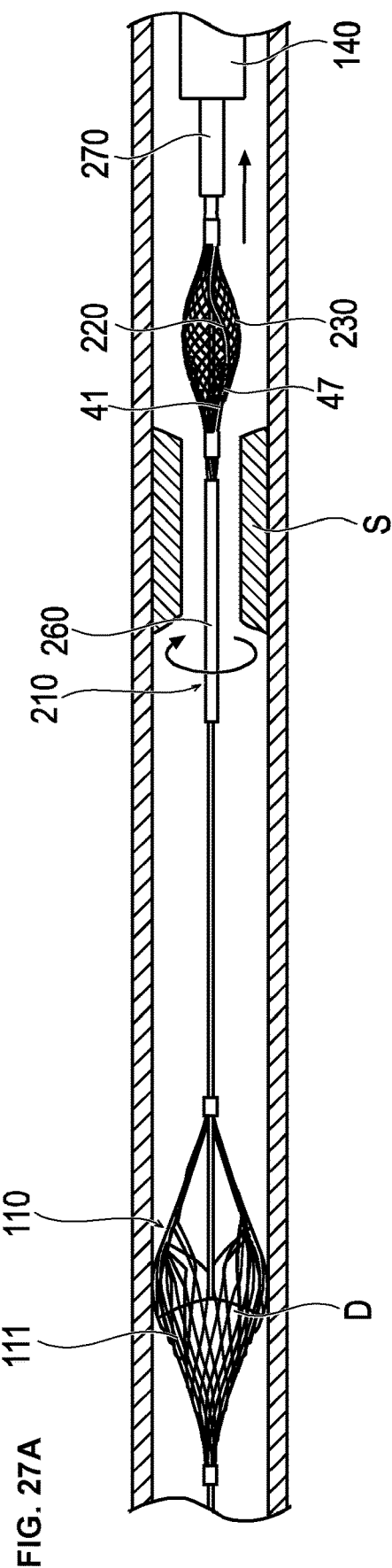
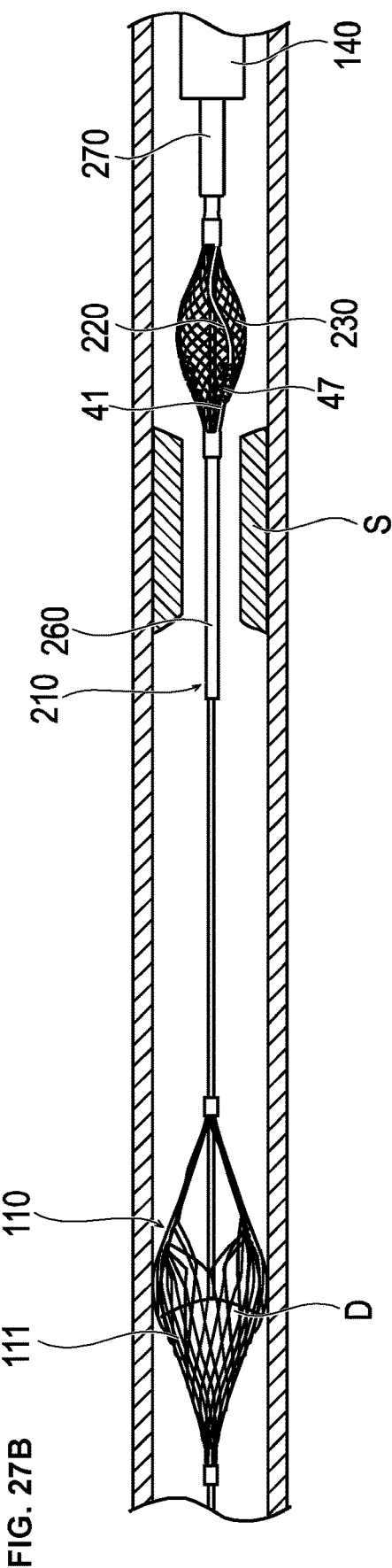

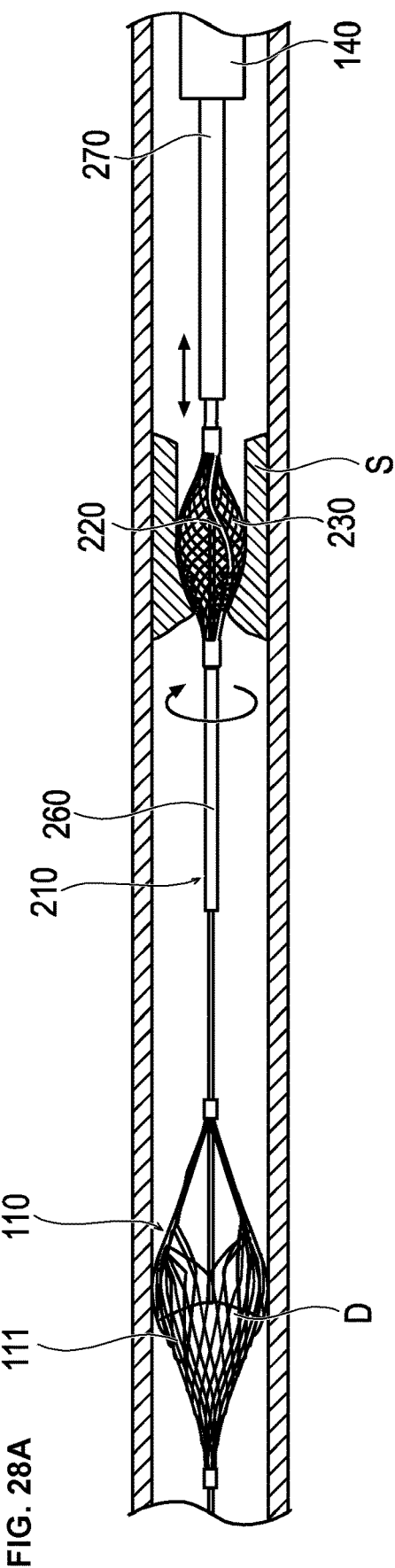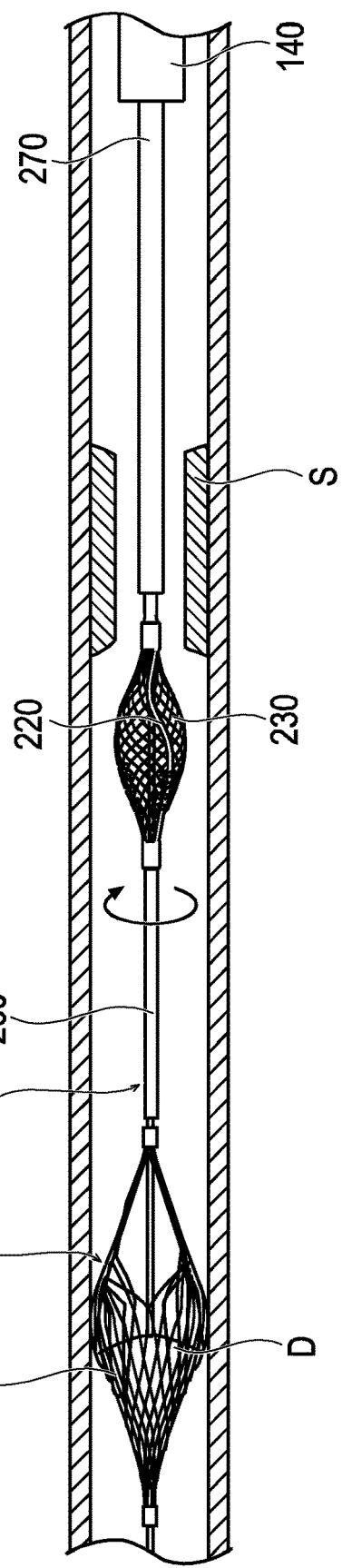

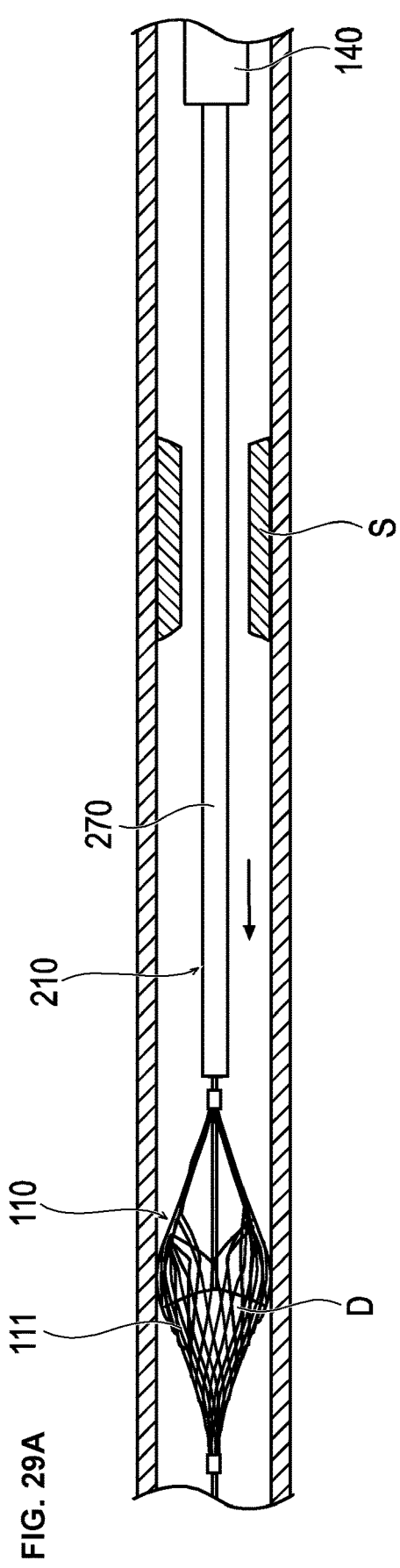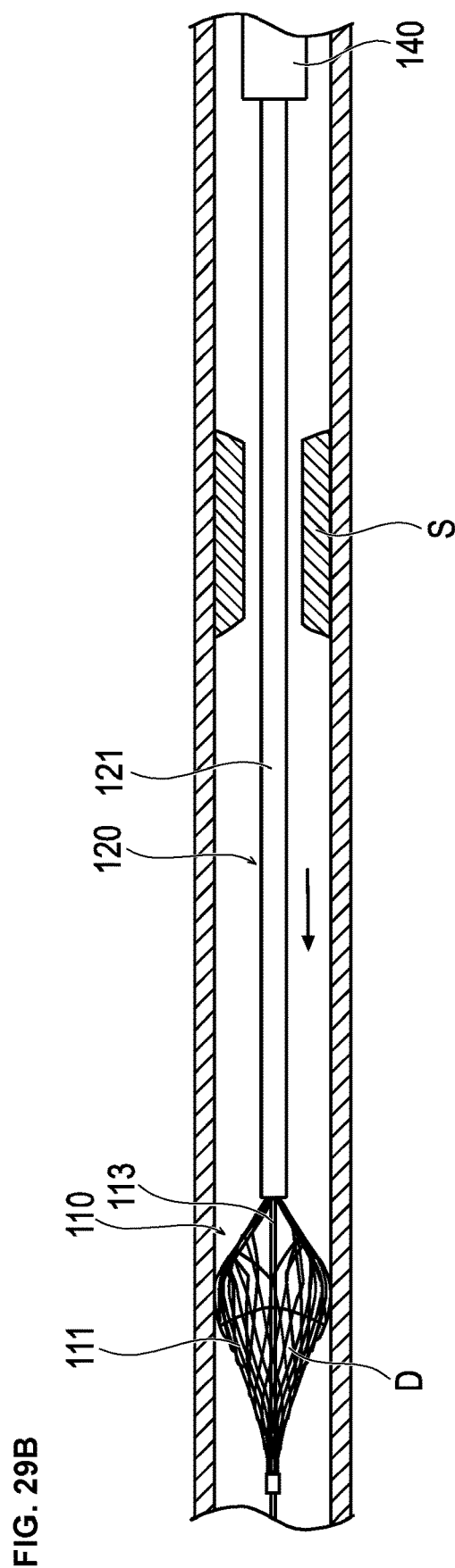

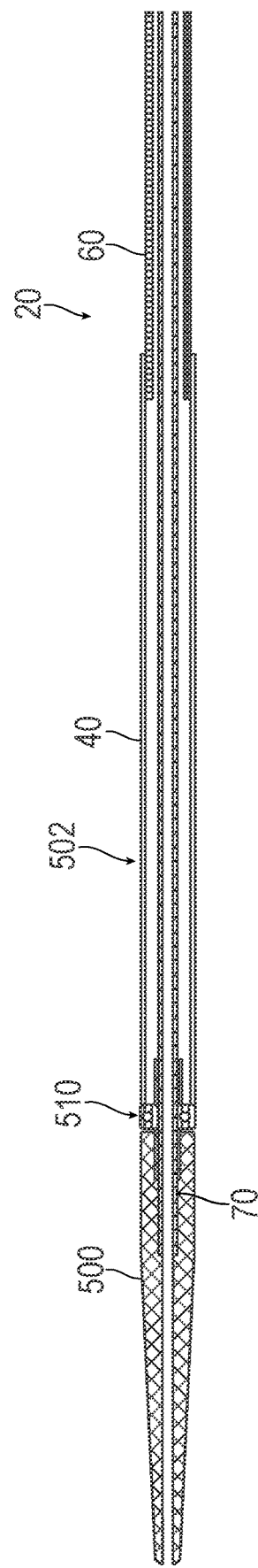
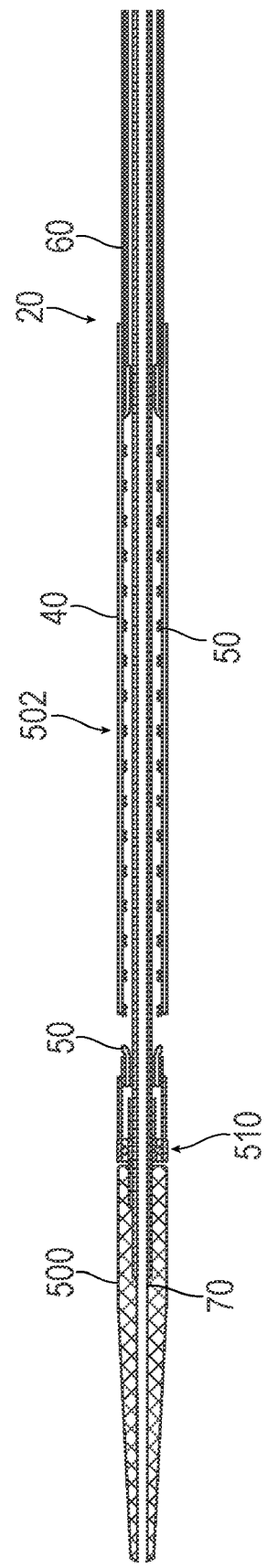
FIG. 35A
FIG. 35B

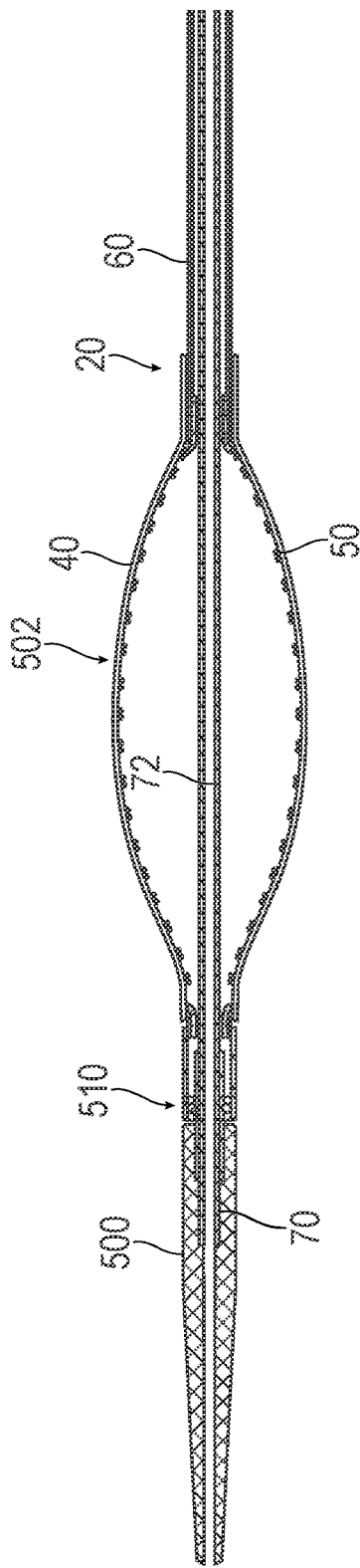
FIG. 36
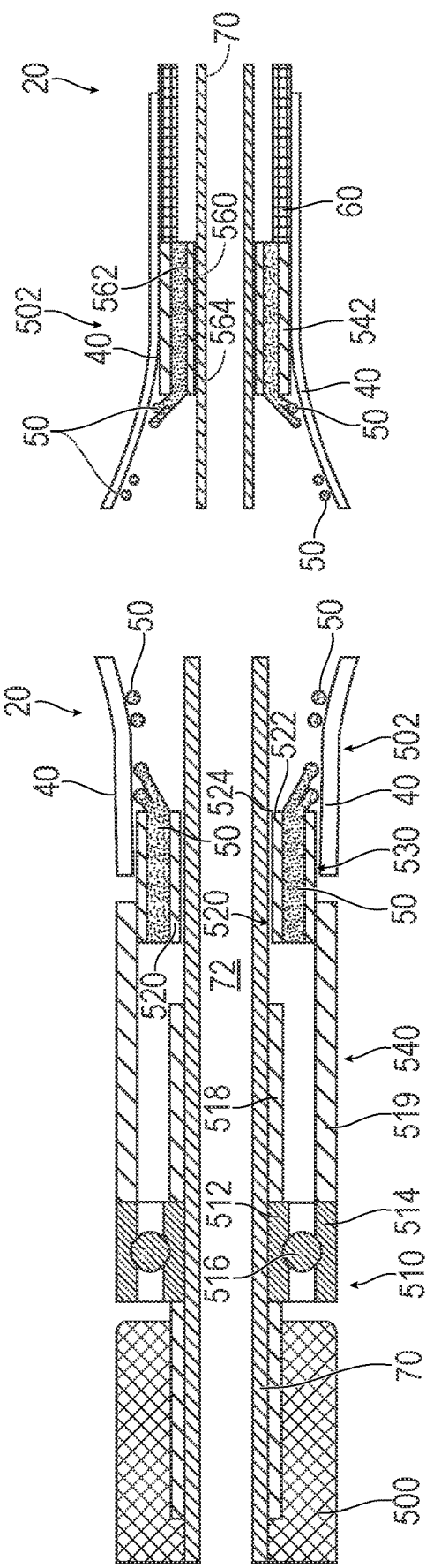
FIG. 37A
FIG. 37B

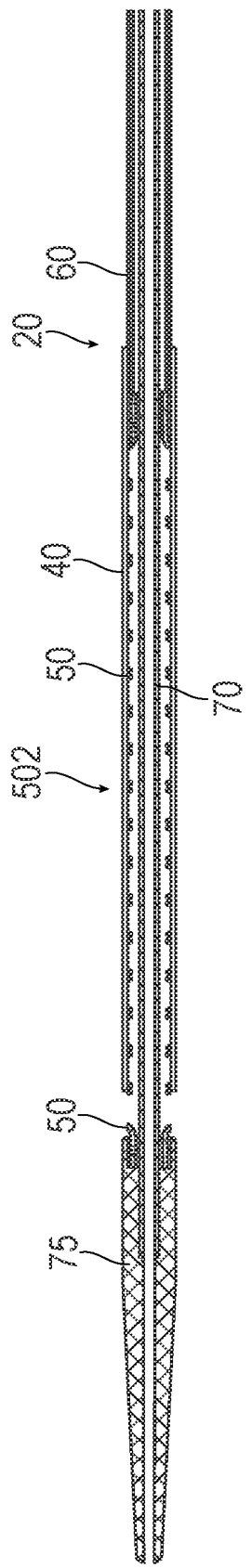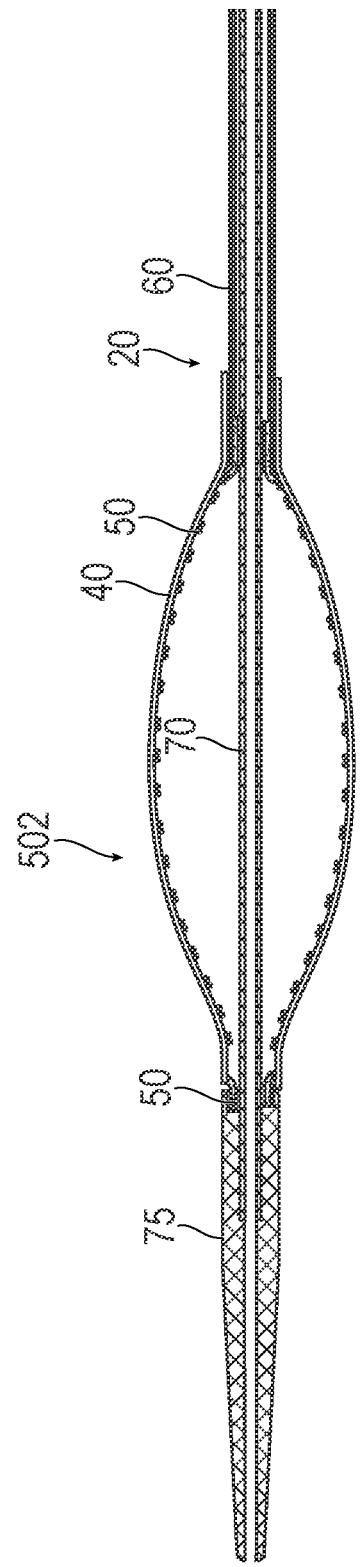
FIG. 38A
FIG. 38B

MEDICAL DEVICE AND TREATMENT METHOD

CROSS-REFERENCES TO RELATED APPLICATIONS

This application is a continuation of U.S. application Ser. No. 15/180,557 filed on Jun. 13, 2016, which is a continuation-in-part of U.S. application Ser. No. 14/931,335 filed on Nov. 3, 2015, which claims priority to Japanese Application No. 2014-224105 filed on Nov. 4, 2014, and U.S. Provisional Patent Application No. 62/104,487 filed on Jan. 16, 2015, the entire contents of all four of which are hereby incorporated by reference.

TECHNICAL FIELD

The present disclosure generally relates to a medical device for cutting a substance from an inner wall surface of a body lumen.

BACKGROUND DISCUSSION

Therapy methods for a stenosed site caused by plaque, thrombus or the like in coronary arteries can include percutaneous transluminal coronary angioplasty (PTCA) of dilating a blood vessel using a balloon, a method of causing a mesh-shaped or coil-shaped stent to indwell the blood vessel as a support for the blood vessel, and the like. However, these methods are less likely to be applied, when the plaque of the stenosed site becomes calcified and hardened or when the stenosed site develops in a bifurcated portion of the coronary arteries. A method, which can enable treatment, can include atherectomy of cutting a stenosis substance such as the plaque, the thrombus, and the like.

For example, as a device for the atherectomy, JP-T-2003-504090 discloses a device in which diamond particles (abrasive materials) adhere to an outer surface of a rotating body located in a distal end portion of a catheter and the rotating body is rotated inside the coronary arteries so as to cut the stenosis substance. The rotating body of this device includes four bars arrayed in the circumferential direction. These bars are expandable so as to fit a diameter of the blood vessel by bending the bars to protrude radially outward.

When expandable and contractible bars are used as in the device disclosed in JP-T-2003-504090, since an edge of the bars comes into contact with the blood vessel, a normal blood vessel is at considerable risk of being damaged. Furthermore, when a hardened stenosis substance such as calcified plaque is cut, the hardened stenosis substance is caught in a gap between the bars, thereby causing an increasing possibility that the device may be damaged.

SUMMARY

A medical device is disclosed which can be relatively easily delivered into a body lumen, which can help ensure a proper cutting range, help reduce the burden on biological tissues, and help prevent the device from being damaged.

A medical device is disclosed for cutting substances inside a body lumen comprising: a rotatable tubular drive shaft; an expanding part connected to a distal side of the drive shaft; a cutting part covering the expanding part; and an elongated tube extending through the drive shaft and connected to the expanding part, wherein a distal end of the expanding part is placed distal to a distal end of the cutting part.

A medical device is disclosed for cutting substances inside a body lumen, the medical device comprising: a drive shaft that is rotatable; at least one strut that is rotatably connected to a distal side of the drive shaft, that extends along a rotation axis, and whose central portion is bent so as to be expandable radially outward; a support portion that is rotatably driven by the drive shaft, that is formed in a mesh shape and a tubular shape while including multiple gaps, at least a portion of which is positioned on a radially inner side of the at least one strut, and that is expandable radially outward by a central portion in a direction extending along the rotation axis being bent, wherein a distal end of the support portion is placed distal to a distal end of the at least one strut; and a linear motion shaft which adjusts a deformation amount of the at least one strut and the support portion.

A treatment method is disclosed for cutting substances inside a body lumen by using a medical device including a rotatable tubular drive shaft, an expanding part connected to a distal side of the drive shaft, a cutting part covering the expanding part, and an elongated tube extending through the drive shaft and connected to the expanding part, wherein a distal end of the expanding part is placed distal to a distal end of the cutting part, and wherein the distal end of the cutting part is spaced apart radially from the distal end of the expanding part, the treatment method comprising: inserting the cutting part and the expanding part which are in a contracted state into the body lumen; detecting a size of a gap between the substances inside the body lumen; expanding the cutting part and the expanding part so as to be larger than the gap between the substances on a further proximal side from the gap between the substances; and cutting the substances by causing the drive shaft to rotate the cutting part and the expanding part so as to be pressed into the gap between the substances.

A medical device is disclosed for cutting substances inside a body lumen, the medical device comprising: an operation unit; a tubular drive shaft configured to extend in an axial direction, the tubular drive shaft having a lumen that extends from a proximal side to a distal end of the tubular drive shaft, the proximal side of the tubular drive shaft being connected to a motor or a drive gear and wherein the tubular drive shaft is configured to be driven and rotatable around the axial direction by the motor or the drive gear; a cutting part configured to be connected to the tubular drive shaft, and wherein the cutting part is configured to rotate around the axial direction in correspondence with the rotation of the tubular drive shaft; an elongated tube configured to extend in the axial direction and configured to penetrate through the lumen of the tubular drive shaft without being fixed to both the tubular drive shaft and the cutting part, the elongated tube having a lumen extending in the axial direction and configured to receive an insertable and removable guide wire, and wherein a proximal end of the elongated tube is located proximal to a proximal end of the motor or the drive gear; an outer sheath configured to accommodate the tubular drive shaft, the outer sheath being configured to be connected to the operation unit, and wherein the operation unit includes the motor or the drive gear; the proximal end of the elongated tube being located in proximity to a proximal wall of the operation unit, and a proximal portion of the elongated tube is held to the proximal wall of the operation unit by a proximal fixing portion arranged between the elongated tube and the operation unit, the proximal fixing portion includes an opening in communication with an opening of the elongated tube; and wherein the tubular drive shaft is configured to be rotatable relative to the elongated tube.

BRIEF DESCRIPTION OF THE DRAWINGS

FIG. 8A is a schematic sectional view illustrating an intravascular state when manual skills are used in a state where a guidewire is inserted into the blood vessel.

FIG. 8B is a schematic sectional view illustrating an intravascular state when manual skills are used in a state where a guiding catheter is inserted into the blood vessel.

FIG. 9A is a schematic sectional view illustrating an intravascular state when manual skills are used in a state where a support catheter is inserted into a stenosed site.

FIG. 9B is a schematic sectional view illustrating an intravascular state when manual skills are used in a state where the filter device is inserted into the blood vessel.

FIG. 10A is a schematic sectional view illustrating an intravascular state when manual skills are used in a state where a filter portion expands.

FIG. 10B is a schematic sectional view illustrating an intravascular state when manual skills are used in a state where the treatment device is inserted into the blood vessel.

FIG. 11A is a schematic sectional view illustrating an intravascular state when manual skills are used in a state where the cutting unit of the treatment device and a support portion are exposed.

FIG. 11B is a schematic sectional view illustrating an intravascular state when manual skills are used in a state where the cutting unit and the support portion expand.

FIG. 12A is a schematic sectional view illustrating an intravascular state when manual skills are used in a state where stenosis substances are cut by the treatment device.

FIG. 12B is a schematic sectional view illustrating an intravascular state when manual skills are used in a state where the cutting unit is accommodated by the outer sheath.

FIG. 13A is schematic sectional view illustrating an intravascular state when manual skills are used in a state when debris collected in the filter portion is aspirated by a catheter.

FIG. 13B is schematic sectional view illustrating an intravascular state when manual skills are used in a state where the filter portion is accommodated inside a tubular body.

FIG. 19A is a longitudinal sectional view illustrating the treatment device in a state before a distal tube comes into contact with a cutting unit.

FIG. 19B is a longitudinal sectional view illustrating the treatment device in a state after the distal tube comes into contact with the cutting unit.

FIG. 25A is a schematic sectional view illustrating an intravascular state when manual skills are used in a state when the cutting unit and the support portion expand.

FIG. 25B is a schematic sectional view illustrating an intravascular state when manual skills are used in a state when stenosis substances are cut by the treatment device.

FIG. 26A is a schematic sectional view illustrating an intravascular state when manual skills are used in a state when the cutting unit and the support portion are pulled out from a stenosed site, and FIG. 26B is a schematic sectional view illustrating an intravascular state when manual skills are used in a state when stenosis substances are cut by the treatment device.

FIG. 27A is a schematic sectional view illustrating an intravascular state when manual skills are used in a state when the cutting unit and the support portion are pulled out from a stenosed site.

FIG. 27B is a schematic sectional view illustrating an intravascular state when manual skills are used in a state when the cutting unit and the support portion expand further.

FIG. 28A is a schematic sectional view illustrating an intravascular state when manual skills are used in a state when stenosis substances are cut by the treatment device.

FIG. 28B is a schematic sectional view illustrating an intravascular state when manual skills are used in a state when stenosis substances have been cut by the treatment device.

FIG. 29A is a schematic sectional view illustrating an intravascular state when manual skills are used in a state when the cutting unit is accommodated by the outer sheath.

FIG. 29B is a schematic sectional view illustrating an intravascular state when manual skills are used in a state when the filter portion is accommodated inside a tubular body.

FIG. 35A is a longitudinal sectional view illustrating the distal end portion of the treatment device according to an exemplary embodiment.

FIG. 35B is a longitudinal sectional view illustrating the distal end portion of the treatment device according to an exemplary embodiment.

FIG. 36 is a longitudinal sectional view illustrating the distal end portion of the treatment device according to an exemplary embodiment in an expanded state.

FIG. 37A is a sectional view illustrating the distal end portion of the treatment device according to an exemplary embodiment.

FIG. 37B is a sectional view illustrating the distal end portion of the treatment device according to an exemplary embodiment.

FIG. 38A is a longitudinal sectional view illustrating the distal end portion of the treatment device according to an exemplary embodiment.

FIG. 38B is a longitudinal sectional view illustrating the distal end portion of the treatment device according to an exemplary embodiment in an expanded state.

DETAILED DESCRIPTION

Figure 1:
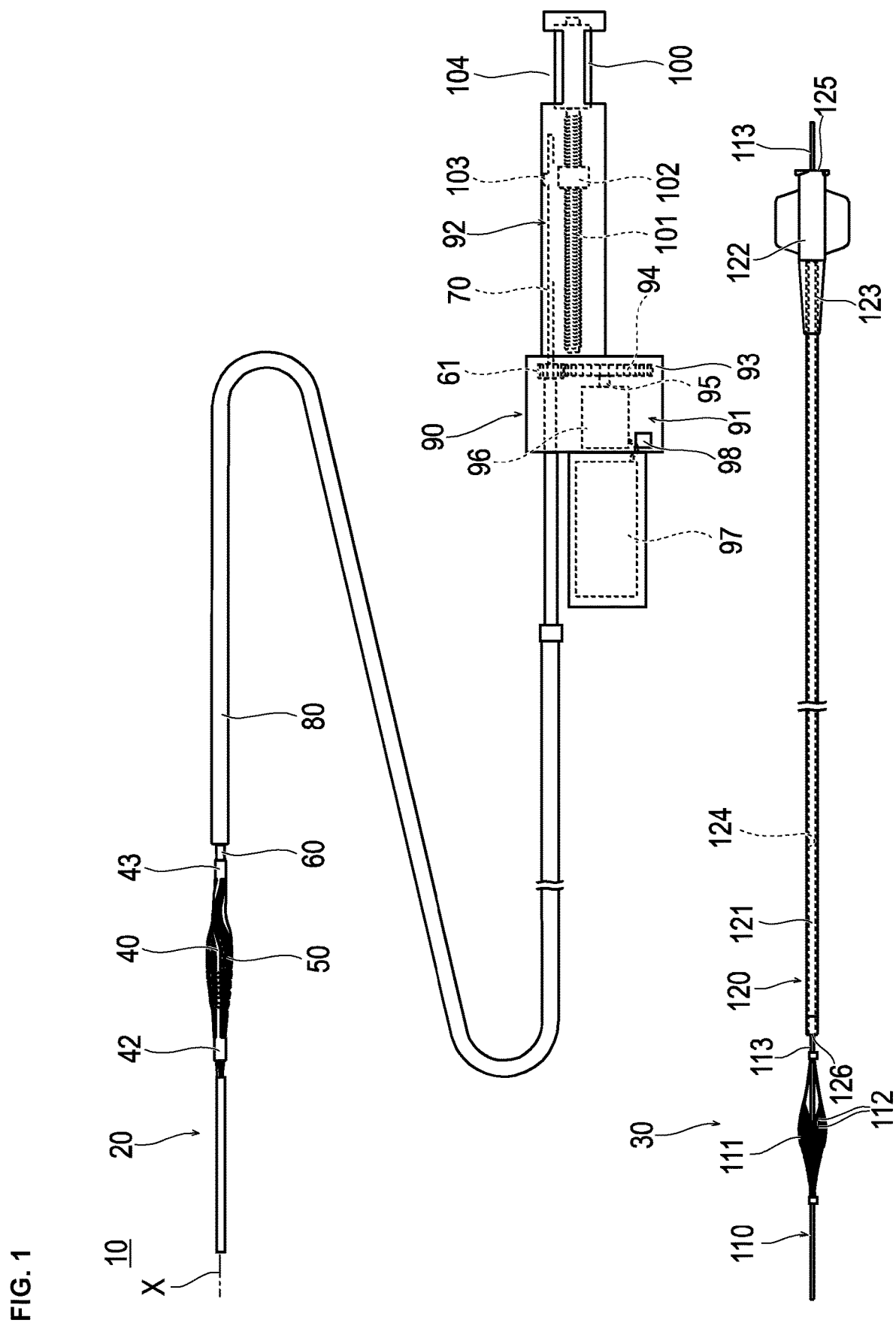
FIG. 1 is a plan view illustrating a state where a cutting unit of a medical device according to a first embodiment contracts.

Hereinafter, embodiments of the present disclosure will be described with reference to the drawings. In order to facilitate description, dimensional ratios in the drawings are exaggerated, and thus are different from actual ratios in some cases.

First Embodiment

A medical device 10 according to a first embodiment of the present disclosure can be used for therapy (treatment) to cut a stenosed site or an occluded site which is caused by plaque, thrombus or the like inside the blood vessel. In this description, a side of the device which is inserted into the blood vessel is referred to as a "distal side", and an operating hand side is referred to as a "proximal side".

As illustrated in FIG. 1, the medical device 10 according to the first embodiment of the present disclosure can include a treatment device 20 which cuts a stenosed site or an occluded site, and a filter device 30 which collects debris (substance) which is cut and dropped off from the stenosed site or the occluded site.

Figure 2:
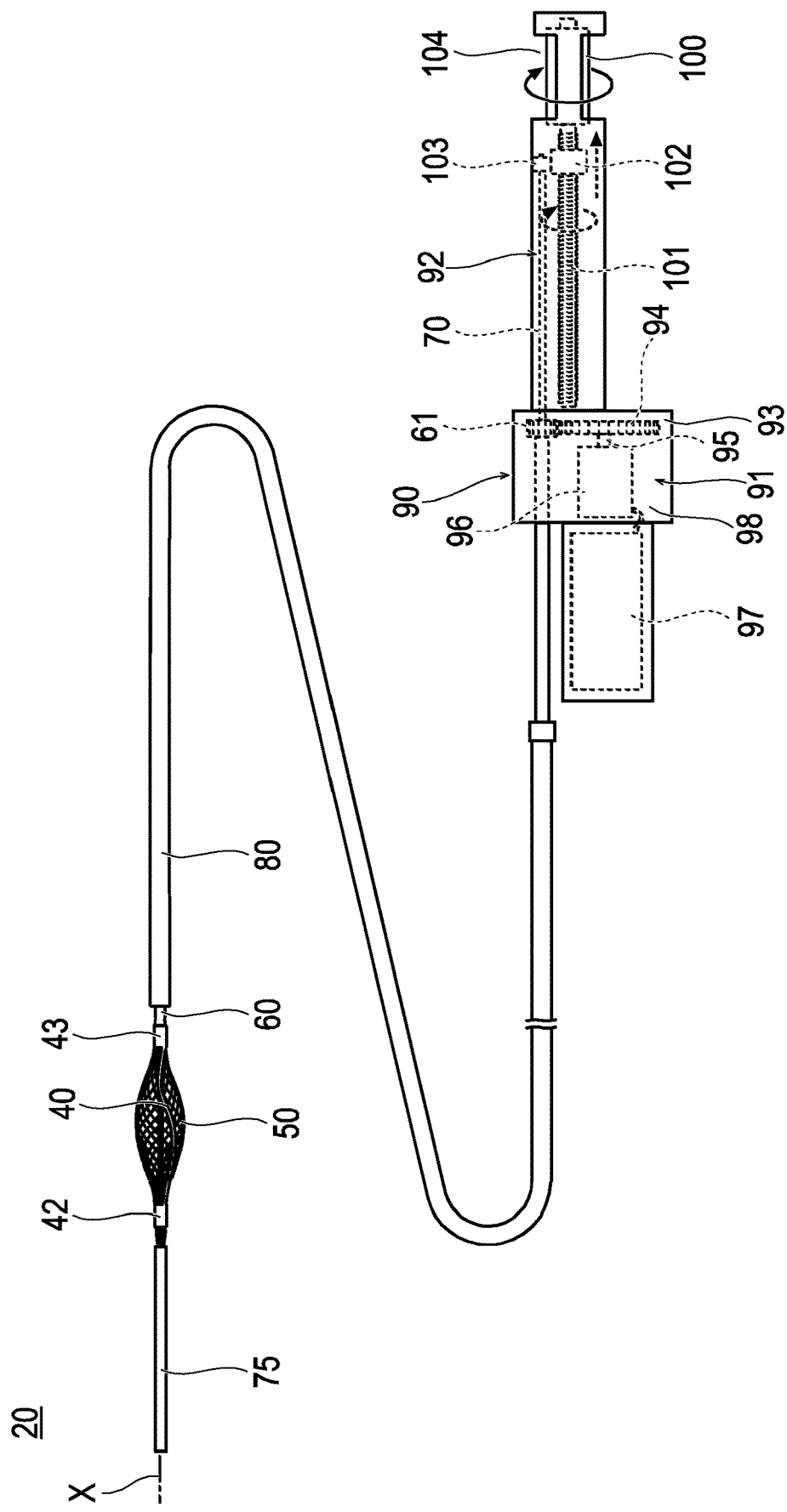
FIG. 2 is a plan view illustrating a state where a cutting unit of a treatment device expands.
Figure 3:
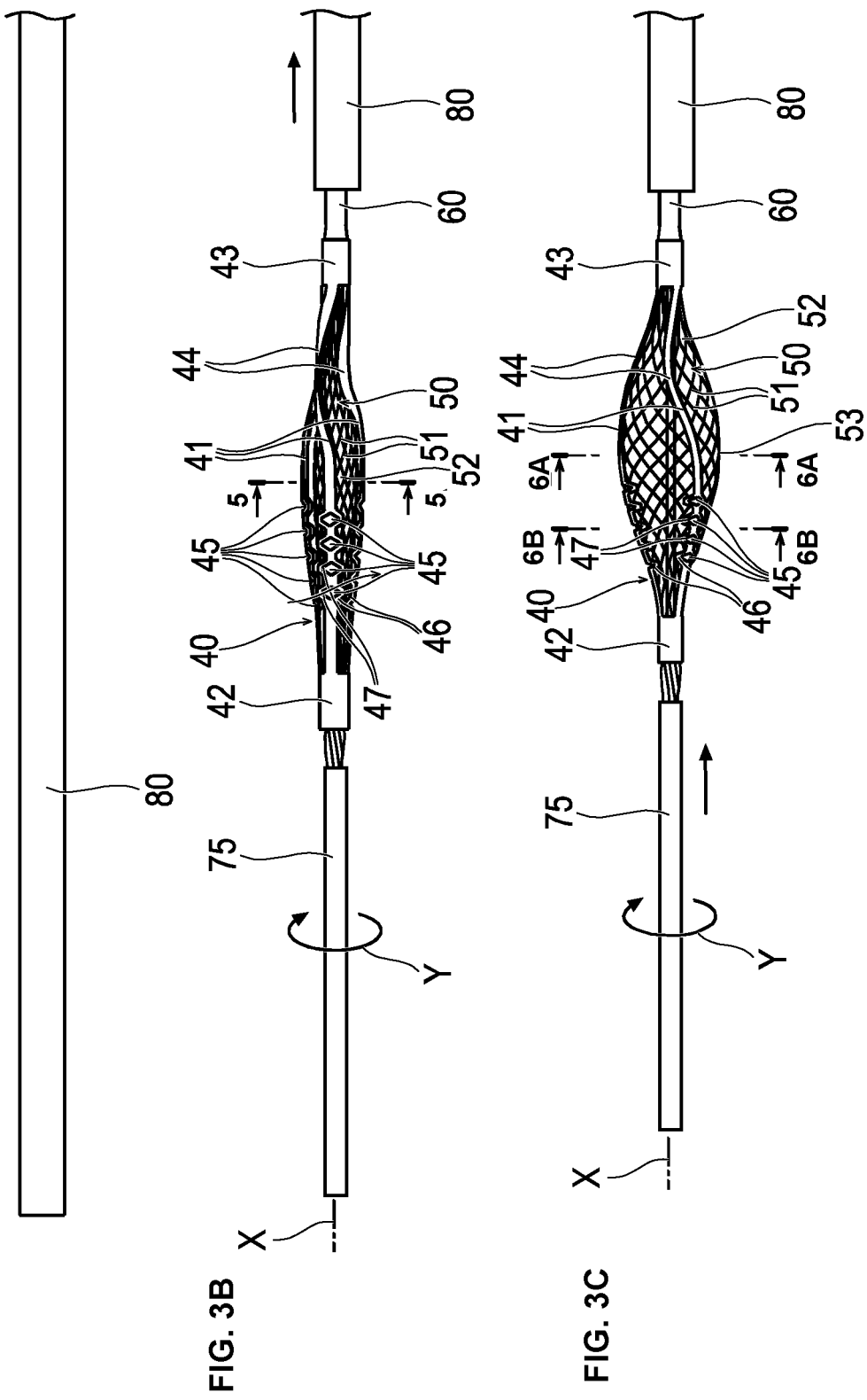
FIG. 3A is a plan view illustrating a distal end portion of the treatment device in a state where the cutting unit is accommodated in an outer sheath.
FIG. 3B is a plan view illustrating a distal end portion of the treatment device in a state where the contracting cutting unit protrudes from the outer sheath.
FIG. 3C is a plan view illustrating a distal end portion of the treatment device in a state where the cutting unit protruding from the outer sheath expands.
Figure 4:
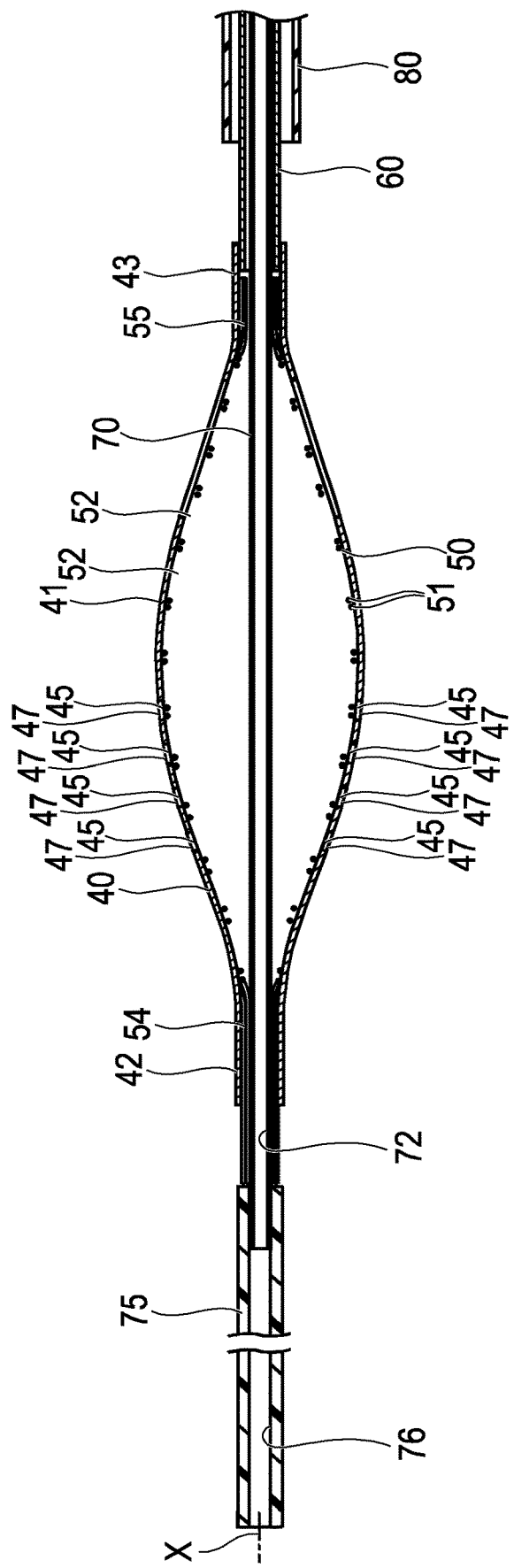
FIG. 4 is a longitudinal sectional view illustrating the distal end portion of the treatment device.
Figure 5:
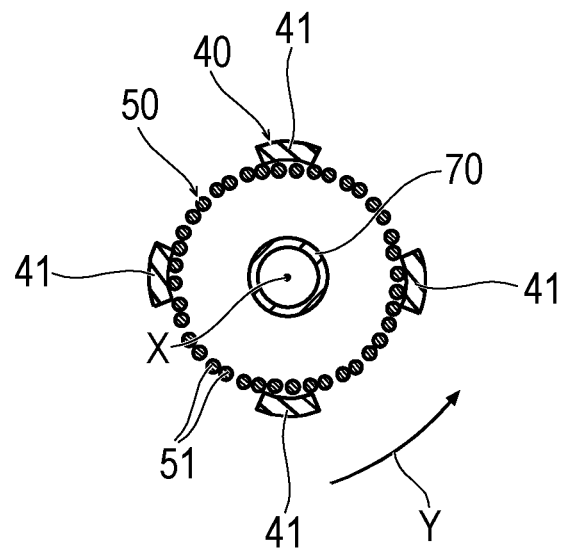
FIG. 5 is a cross-sectional view taken along line 5-5 in FIG. 3B.

As illustrated in FIGS. 1 and 2, the treatment device 20 can include a cutting unit 40 which is expandable and contractible radially outward, a support portion 50 which supports the cutting unit 40, a drive shaft 60 which rotates the cutting unit 40, a linear motion shaft 70 which adjusts a deformation amount of the cutting unit 40, a distal tube 75 which interlocks with a distal side of the linear shaft 70, an outer sheath 80 which can accommodate the cutting unit 40, and an operation unit 90 which is disposed on an operating hand side for operation.

As illustrated in FIGS. 3A to 6, the cutting unit 40 can include at least one (four in the present embodiment) strut 41 which extends along a rotation axis X of the drive shaft 60, a tubular distal fixed end 42 which is formed integrally with the strut 41 on a distal side of each of the plurality of struts 41, and a tubular proximal fixed end 43 which is formed integrally with the strut 41 on a proximal side of each of the plurality of struts 41. If the distal fixed end 42 and the proximal fixed end 43 are moved closer to each other, the strut 41 can shift from a contraction state (refer to FIGS. 3B and 5) of having a substantially linear shape to an expansion state (refer to FIGS. 3C, 6A, and 6B) of being deformed so as to be bent radially outward.

In the strut 41, a tilting portion 44 which is curved so as to tilt to the rotation axis X in a contraction state is formed on the proximal side, and multiple opening portions 45 which penetrate an inner peripheral surface from an outer peripheral surface are formed on the distal side. The strut 41 has wide portions 46 whose width in the circumferential direction (rotating direction Y) is relatively wider than that of the adjacent portion. The opening portions 45 are respectively formed in the wide portions 46. The opening portion 45 is formed at multiple locations (four or five locations in the present embodiment) along the extending direction of the strut 41. An inner edge portion of the opening portion 45 functions as a blade 47 for cutting a stenosed site or an occluded site. A position where the blade 47 of the strut 41 is formed is located on the further distal side from a portion where an outer diameter of the strut 41 is maximized in an expansion state (substantially central portion in a direction extending along the rotation axis X). In accordance with an exemplary embodiment, it can be preferable to chamfer an edge portion other than the inner edge portion configuring the blade 47 of the opening portion 45 in the strut 41.

The strut 41 having four opening portions 45 formed therein and the strut 41 having five opening portions 45 formed therein are alternately arranged in the circumferential direction. Therefore, when the cutting unit 40 is cut out from one tubular body by means of laser processing, machining or the like, the four opening portions 45 and the five opening portions 45 can be alternately arranged so as to be shifted from each other, thereby enabling the opening portion 45 to secure a suitable width. In addition, since the blade 47 of the strut 41 adjacent in the circumferential direction is arranged so as to be shifted, a predetermined portion can be prevented from being unevenly cut off. Accordingly, a stenosed site or an occluded site can be effectively cut.

Figure 6A:
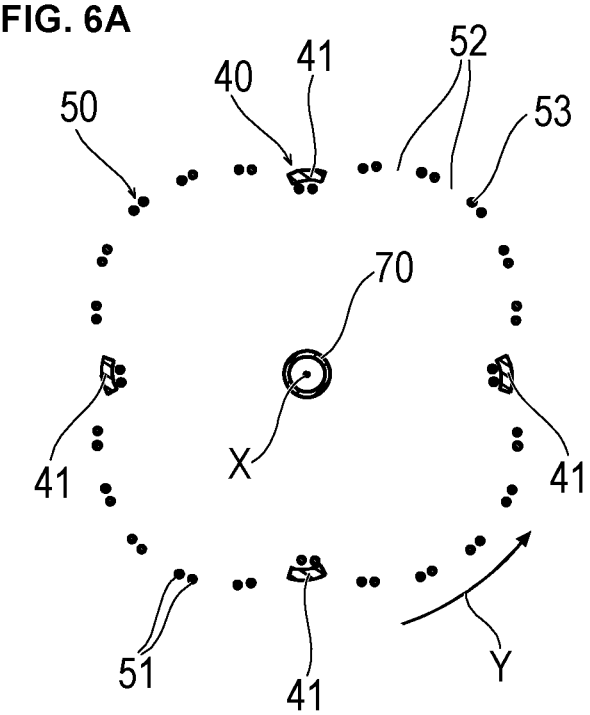
FIG. 6A is a cross-sectional view of the treatment device in an expansion state taken along line 6A-6A in FIG. 3C.
Figure 6B:
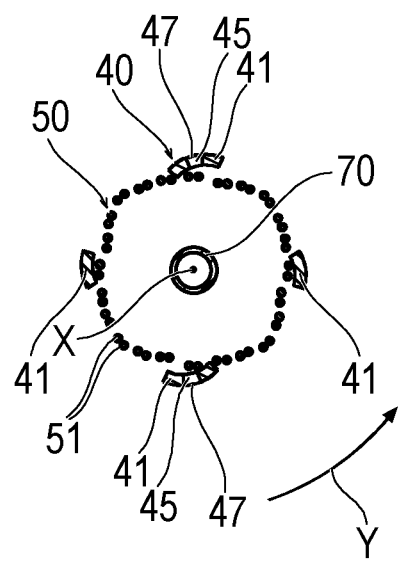
FIG. 6B is a cross-sectional view of the treatment device in an expansion state taken along line 6B-6B in FIG. 3C.

If the strut 41 is brought into an expansion state, an outer peripheral surface of a portion having the blade 47 formed therein is deformed so as to tilt radially inward as it goes toward a side in the rotating direction Y (refer to FIG. 6B). Therefore, when the strut 41 is rotated in the expansion state, the strut 41 can come into smooth contact with a contact target from a side tilting radially inward in the strut 41. Accordingly, excessive damage to biological tissues can be reduced. In addition, since the strut 41 is formed by being cut out from a tubular body having a diameter which is smaller than a diameter in the expansion state, the radius of curvature of the outer peripheral surface of the strut 41 is smaller than a distance from the rotation axis X to the outer peripheral surface of the strut 41 in the expansion state. Therefore, an edge portion of the strut 41 becomes further less likely to come into contact with the contact target. Accordingly, excessive damage to biological tissues can be further reduced.

For example, as a configuration material of the cutting unit 40, a shape memory alloy which is provided with a shape memory effect or super-elasticity by means of heat treatment, stainless steel, or the like can be preferably used. As the shape memory alloy, Ni—Ti-based alloys, Cu—Al—Ni-based alloys, Cu—Zn—Al-based alloys, combinations thereof, or the like are preferably used.

The support portion 50 is arranged so as to support the cutting unit 40 radially inward from the cutting unit 40, is formed by braiding multiple wires 51, and is formed in a tubular shape so as to have a gap 52 between the wires 51. A distal end portion 54 of the support portion 50 is configured so that the multiple wires 51 gather into a tubular shape, and is fixed to an inner side surface of the distal fixed end 42 of the strut 41 and the outer peripheral surface of the linear motion shaft 70 (refer to FIG. 4). A proximal end portion 55 of the support portion 50 is configured so that the multiple wires 51 gather into a tubular shape, and is fixed to an inner peripheral surface of the proximal fixed end 43 of the strut 41.

If the distal fixed end 42 and the proximal fixed end 43 are moved close to each other, the support portion 50 can shift from a contraction state (refer to FIG. 3B) where the support portion has a tubular shape having a substantially uniform outer diameter to an expansion state (refer to FIGS. 3C and 4) where the support portion 50 is deformed so that a central portion of the support portion 50 is bent radially outward.

A maximum expansion portion 53 whose outer diameter is largest in the support portion 50 in the expansion state protrudes radially outward between the struts 41 since a gap between the struts 41 in the expansion state increases (refer to FIG. 6A). Therefore, a portion which expands outward most in the strut 41 in the expansion state and is likely to come into contact with biological tissues is located further radially inward from the maximum expansion portion 53 of the support portion 50. Accordingly, normal biological tissues can be prevented from being damaged by the edge portion of the strut 41.

Then, in a portion in the vicinity of the blade 47 of the strut 41, a distance from the rotation axis X is short (diameter is small), and the wide portion 46 is formed. Accordingly, a gap between the struts 41 is narrow. Thus, the support portion 50 located in the vicinity of the blade 47 is prevented from protruding radially outward from the portion between the struts 41. Therefore, the blade 47 can be brought into contact with a contact target without being hindered by the support portion 50 (refer to FIG. 6B).

In order not to cause damage to the biological tissues in contact, it is preferable to form the wire 51 so that rigidity of the wire 51 is lower than that of the strut 41 and a corner portion in a cross section has the curvature, and is more preferable to form the wire 51 so that the cross section has a circular shape.

For example, an outer diameter of the wire 51 is 0.05 mm to 0.15 mm, although the outer diameter can be optionally selected depending on materials, application conditions or the like of the wire 51.

A configuration material of the wire 51 is preferably a flexible material. For example, a shape memory alloy which is provided with a shape memory effect or super-elasticity by means of heat treatment, stainless steel, Ta, Ti, Pt, Au, W, polyolefin such as polyethylene, polypropylene and the like, polyamide, polyester such as polyethylene terephthalate or the like, fluorine-based polymer such as ETFE and the like, polyether ether ketone (PEEK), polyimide, or the like can be preferably used. As the shape memory alloy, Ni—Ti-based alloys, Cu—Al—Ni-based alloys, Cu—Zn—Al-based alloys, combinations thereof, or the like are preferably used. For example, structures having multiple materials combined therewith include a structure in which a core wire made of Pt is covered with Ni—Ti alloy in order to provide contrast, and a structure a core wire made of Ni—Ti alloy is subjected to gold plating.

For example, an inner diameter of the cutting unit 40 in a contraction state is 0.9 mm to 1.6 mm, although the inner diameter can be optionally selected depending on each inner diameter of applied body lumens or the like. As an example, the inner diameter can be set to 1.4 mm. For example, an outer diameter of the cutting unit 40 in the contraction state is 1.1 mm to 1.8 mm, although the outer diameter can be optionally selected depending on each inner diameter of applied body lumens or the like. As an example, the inner diameter can be set to 1.7 mm. For example, a length of the cutting unit 40 in a direction extending along the rotation axis X is 10 mm to 30 mm, although the length can be optionally selected depending on applications. As an example, the length can be set to 20 mm.

For example, the maximum outer diameter of the cutting unit 40 in an expansion state is 3.0 mm to 8.0 mm, although the maximum outer diameter can be optionally selected depending on each inner diameter of applied body lumens or the like. As an example, the maximum outer diameter can be set to 7.0 mm.

For example, a length in which the maximum expansion portion 53 of the support portion 50 in the expansion state protrudes radially outward from the strut 41 is 0.05 mm to 0.5 mm, although the length can be optionally selected. As an example, the length can be set to 0.2 mm.

As illustrated in FIGS. 1 to 4, the drive shaft 60 is formed in a tubular shape, a distal side of the drive shaft 60 is fixed to the proximal fixed end 43 of the cutting unit 40, and a driven gear 61 is fixed to a proximal side of the drive shaft 60. A proximal portion of the drive shaft 60 rotatably interlocks with a casing 91 of the operation unit 90.

The drive shaft 60 is flexible. Moreover, the drive shaft 60 has properties in which rotational power acting from the proximal side can be transmitted to the distal side. For example, the drive shaft 60 is configured to include a tubular body having a shape of a multi-layer coil such as a three-layer coil or the like whose winding directions are alternately rightward, leftward, and rightward, and a reinforcing member incorporated in the drive shaft 60 such as wires or the like made of polyolefin such as polyethylene, polypropylene and the like, polyamide, polyester such as polyethylene terephthalate or the like, fluorine-based polymer such as ETFE and the like, polyether ether ketone (PEEK), polyimide, or combinations thereof.

For example, an inner diameter of the drive shaft 60 is 0.7 mm to 1.4 mm, although the inner diameter can be optionally selected. As an example, the inner diameter can be set to 1.2 mm. For example, an outer diameter of the drive shaft 60 is 0.8 mm to 1.5 mm, although the outer diameter can be optionally selected. As an example, the outer diameter can be set to 1.35 mm.

The linear motion shaft 70 is a tubular body which can move in the direction of the rotation axis X relative to the drive shaft 60 in order to expand and contract the cutting unit 40 and the support portion 50. The linear motion shaft 70 penetrates the drive shaft 60, the cutting unit 40, and the support portion 50. In the linear motion shaft 70, a distal side of the linear motion shaft 70 is fixed to the distal end portion 54 of the wire 51, and a proximal side of the linear motion shaft 70 is connected to a moving mechanism 92 which linearly moves the linear motion shaft 70 along the rotation axis X. The linear shaft 70 internally has a lumen 72 into which a guidewire can be inserted.

A configuration material of the linear motion shaft 70 is preferably a flexible material. For example, a shape memory alloy which is provided with a shape memory effect or super-elasticity by means of heat treatment, stainless steel, Ta, Ti, Pt, Au, W, polyolefin such as polyethylene, polypropylene and the like, polyamide, polyester such as polyethylene terephthalate or the like, fluorine-based polymer such as ETFE and the like, polyether ether ketone (PEEK), polyimide, or the like can be preferably used. As the shape memory alloy, Ni—Ti-based alloys, Cu—Al—Ni-based alloys, Cu—Zn—Al-based alloys, combinations thereof, or the like are preferably used. In addition, the linear motion shaft 70 may be configured to include multiple materials, or a reinforcing material such as a wire or the like may be incorporated therein.

For example, an inner diameter of the linear motion shaft 70 is 0.5 mm to 1.2 mm, although the inner diameter can be optionally selected. As an example, the inner diameter can be set to 0.95 mm. For example, an outer diameter of the linear motion shaft 70 is 0.6 mm to 1.3 mm, although the outer diameter can be optionally selected. As an example, the outer diameter can be set to 1.05 mm.

The outer sheath 80 is a tubular body for covering the outer side of the drive shaft 60, and is movable and rotatable with respect to the drive shaft 60 in a direction extending along the rotation axis X. The outer sheath 80 is operable by gripping the proximal portion. The outer sheath 80 can internally accommodate the cutting unit 40 and the support portion 50 in a contraction state by being moved to the distal side. The cutting unit 40 and the support portion 50 can be exposed outward by moving the outer sheath 80 to the proximal side.

A configuration material of the outer sheath 80 is not particularly limited. However, for example, polyolefin such as polyethylene, polypropylene and the like, polyamide, polyester such as polyethylene terephthalate or the like, fluorine-based polymer such as ETFE and the like, polyether ether ketone (PEEK), polyimide, or the like can be preferably used. In addition, the outer sheath 80 may be configured to include multiple materials, or a reinforcing material such as a wire or the like may be incorporated therein.

For example, an inner diameter of the outer sheath 80 can be 1.2 mm to 1.9 mm, although the inner diameter can be optionally selected. As an example, the inner diameter can be set to 1.8 mm. For example, an outer diameter of the outer sheath 80 can be 1.3 mm to 2.0 mm, although the outer diameter can be optionally selected. As an example, the outer diameter can be set to 2.0 mm.

The distal tube 75 is fixed to the distal side of the linear motion shaft 70. A lumen 76 is formed inside the distal tube 75. The lumen 76 communicates with the lumen 72 of the linear motion shaft 70.

A configuration material of the distal tube 75 is not particularly limited. However, for example, polyolefin such as polyethylene, polypropylene, ethylene-propylene copolymer, ethylene-vinyl acetate copolymer, or the like polyvinyl chloride, polystyrene, polyamide, polyimide, combinations thereof, or the like can be preferably used.

As illustrated in FIGS. 1 and 2, the operation unit 90 can include the casing 91, a drive mechanism 93 which provides the drive shaft 60 with a rotating force, and the moving mechanism 92 which moves the linear motion shaft 70 along the rotation axis X.

The drive mechanism 93 can include a drive gear 94 which meshes with the driven gear 61, a motor 96 which serves as a drive source including a rotary shaft 95 to which the drive gear 94 is fixed, a battery 97 such as an electric cell or the like which supplies power to the motor 96, and a switch 98 which controls driving of the motor 96. The switch 98 is turned on and the rotary shaft 95 of the motor 96 is rotated, thereby rotating the driven gear 61 meshing with the drive gear 94 and rotating the drive shaft 60. If the drive shaft 60 is rotated, the cutting unit 40, the support portion 50, and the distal tube 75, which are fixed to the distal side of the drive shaft 60.

The moving mechanism 92 can include a dial 100 which can be rotated by an operator's finger, a rotatable feed screw 101, which coaxially interlocks with the dial 100, a moving base 102 which is linearly movable by the feed screw 101, and a bearing portion 103 which is fixed to the moving base 102 and which rotatably supports the linear motion shaft 70.

The dial 100 is rotatably held inside the casing 91, and an outer peripheral surface of the dial 100 is exposed from an opening portion 104 formed in the casing 91. The dial 100 is rotatable by the finger operating the outer peripheral surface. The feed screw 101 is rotatably held inside the casing 91. The moving base 102 has a female screw to which the feed screw 101 is screwed, is not rotatable with respect to the casing 91, and is linearly movable along the rotation axis X. The bearing portion 103, which is fixed to the moving base 102 applies a moving force to the linear motion shaft 70 in response to the movement of the moving base 102. Accordingly, it is preferable to use a thrust bearing which can receive a thrust force.

Figure 7:
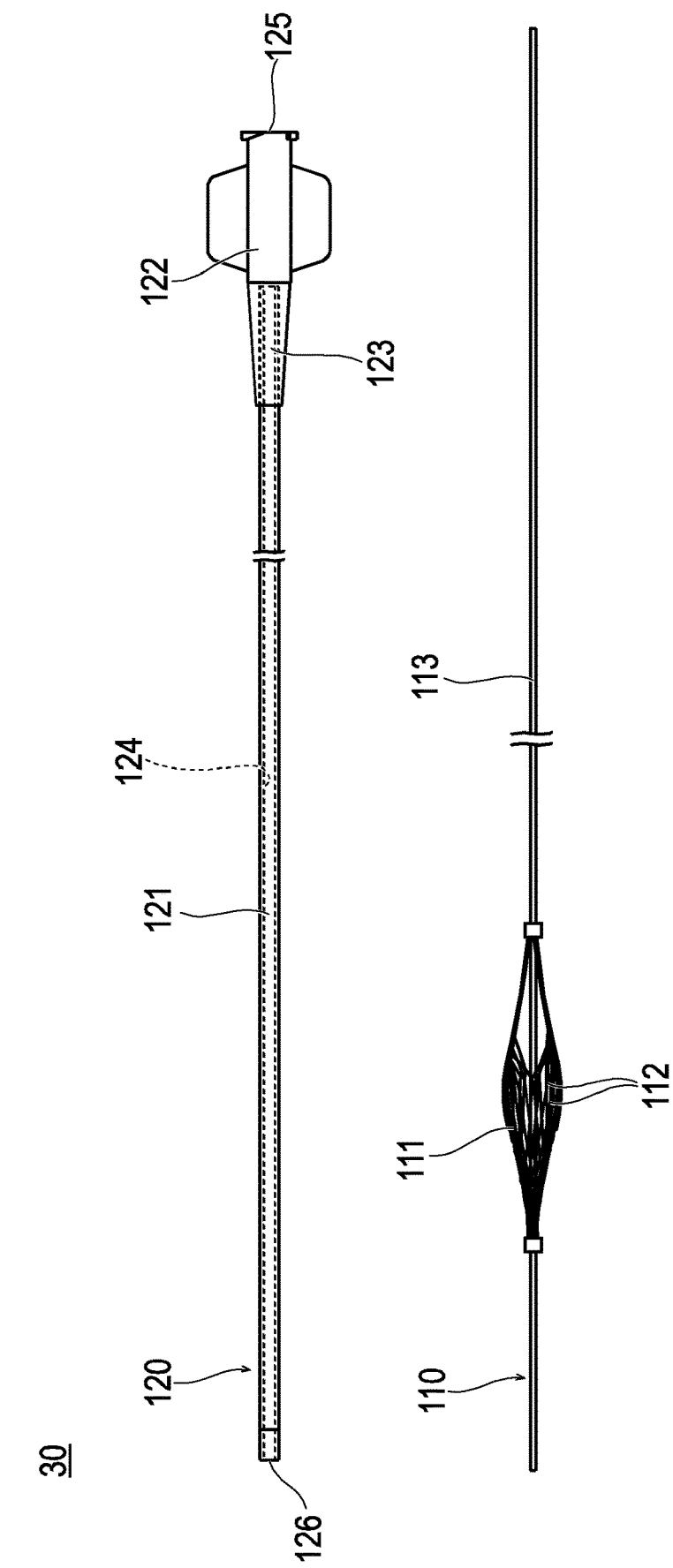
FIG. 7 is a plan view illustrating a filter device.

As illustrated in FIGS. 1 and 7, the filter device 30 can include a filter instrument 110 which has a function as a filter, and a sheath 120 which can accommodate the filter instrument 110.

The filter instrument 110 can include a filter portion 111 which is obtained by braiding multiple element wires 112, and an elongated shaft 113 which interlocks with the filter portion 111 by penetrating the filter portion 111.

The filter portion 111 can contract when being accommodated inside the sheath 120, and can expand by using a self-expansion force when being released from the sheath 120. In the filter portion 111, a distal side is shaped into a closed cage and interlocks with the shaft portion 113, and a proximal side interlocks with the shaft portion 113 by the multiple element wires 112 being collectively twisted.

An outer diameter of the element wire 112 can be optionally selected depending on materials, usage, or the like of the element wire 112. However, for example, the outer diameter is 20 μm to 100 μm. As an example, the outer diameter can be set to 40 μm.

A configuration material of the element wire 112 is preferably a flexible material. For example, a shape memory alloy which is provided with a shape memory effect or super-elasticity by means of heat treatment, stainless steel, Ta, Ti, Pt, Au, W, polyolefin such as polyethylene, polypropylene and the like, polyamide, polyester such as polyethylene terephthalate or the like, fluorine-based polymer such as ETFE and the like, polyether ether ketone (PEEK), polyimide, or the like can be preferably used. As the shape memory alloy, Ni—Ti-based alloys, Cu—Al—Ni-based alloys, Cu—Zn—Al-based alloys, combinations thereof, or the like are preferably used. For example, structures having multiple materials combined therewith include a structure in which a core wire made of Pt is covered with Ni—Ti alloy in order to provide contrast, and a structure a core wire made of Ni—Ti alloy is subjected to gold plating.

A configuration material of the shaft portion 113 is not particularly limited. However, for example, stainless steel, a shape memory alloy, or the like can be preferably used.

The sheath 120 can include a tubular body 121, a hub 122, and a kink resistant protector 123. The tubular body 121 can include a lumen 124 which can accommodate the filter instrument 110, and is open in a tubular body opening portion 126 formed in the distal end portion. The hub 122 is fixed to the proximal end portion of the tubular body 121, and can include a hub opening portion 125, which communicates with the lumen 124. The kink resistant protector 123 can be a flexible member for covering an interlock portion between the tubular body 121 and the hub 122, and can help prevent kinking of the tubular body 121.

A configuration material of the tubular body 121 is not particularly limited. However, for example, polyolefin such as polyethylene, polypropylene, ethylene-propylene copolymer, ethylene-vinyl acetate copolymer, or the like, polyvinyl chloride, polystyrene, polyamide, polyimide, combinations thereof, or the like can be preferably used.

Next, a method of using the medical device 10 according to the present embodiment will be described by exemplifying a case where stenosis substances inside the blood vessel are cut.

First, an introducer sheath (not illustrated) is percutaneously inserted into the blood vessel on a further upstream side (proximal side) from a stenosed site S in the blood vessel. A guidewire 130 is inserted into the blood vessel via the introducer sheath. Then, the guidewire 130 is pushed so as to move forward and reach a proximal side of the stenosed site S, as illustrated in FIG. 8A. Thereafter, a proximal end portion of the guidewire 130, which is located outside the body is inserted into a catheter opening portion 141 on a distal side of a guiding catheter 140. As illustrated in FIG. 8B, the guiding catheter 140 is inserted into the blood vessel along the guidewire 130 so as to reach the proximal side of the stenosed site S.

Next, the proximal end portion of the guidewire 130, which is located outside the body is inserted into a catheter opening portion 151 on a distal side of a support catheter 150, and the support catheter 150 is pushed to move forward to the proximal side of the stenosed site S. Thereafter, as illustrated in FIG. 9A, the support catheter 150 and the guidewire 130 are caused to reach a further distal side from the stenosed site S. Thereafter, the guidewire 130 is removed therefrom in a state where the support catheter 150 remains inside the blood vessel.

Then, the filter device 30 in which the filter instrument 110 is accommodated inside the sheath 120 is prepared. The filter portion 111 is arranged at a position close to the distal end portion of the tubular body 121 of the sheath 120, and a shape of the filter portion 111 is restricted to a contraction state. Then, as illustrated in FIG. 9B, the filter device 30 is inserted into the blood vessel via the support catheter 150 so as to reach the further distal side from the stenosed site S. Thereafter, the support catheter 150 is removed therefrom.

Next, the sheath 120 is moved to the proximal side relative to the filter instrument 110 so that the filter portion 111 protrudes to the distal side from the tubular body 121.

In this manner, as illustrated in FIG. 10A, the filter portion 111 is brought into an expansion state by using its own restoring force. An outer peripheral portion of the filter portion 111 which is shaped into a cage comes into contact with an inner wall surface of the blood vessel. At this time, the filter portion 111 is open toward the stenosed site S on the upstream side (proximal side). Thereafter, the sheath 120 is removed therefrom by leaving the filter instrument 110 behind.

Next, the treatment device 20 in a state where the cutting unit 40 and the support portion 50 contracts and are accommodated inside the outer sheath 80 is prepared. The proximal end portion of the shaft portion 113 is inserted into the distal side opening portion of the distal tube 75. As illustrated in FIG. 10B, the proximal end portion of the shaft portion 113 is caused to reach the inside of the blood vessel via the guiding catheter 140. Then, as illustrated in FIG. 11A, the outer sheath 80 is moved to the proximal side, and the cutting unit 40 and the support portion 50 are exposed inside the blood vessel. In this state, the cutting unit 40 and the support portion 50 are in a contraction state. Thereafter, if the dial 100 is rotated as illustrated in FIG. 2, the feed screw 101 is rotated, the moving base 102 is moved to the proximal side, and the linear motion shaft 70 interlocking with the moving base 102 is moved to the proximal side. If the linear motion shaft 70 is moved to the proximal side, the distal fixed end 42 of the cutting unit 40 moves so as to be closer to the proximal fixed end 43. As illustrated in FIG. 11B, the cutting unit 40 and the support portion 50 are brought into a state of expanding radially outward. A size of the cutting unit 40 and the support portion 50 can be optionally adjusted depending on a rotation amount of the dial 100. In this way, as compared to a case of cutting by using a rotating body in which an abrasive material or the like adheres to an outer surface of a balloon whose diameter is regulated during expansion, the cutting unit 40 can effectively perform cutting, since a size during the expansion can be optionally adjusted to a desirable size.

Next, if the switch 98 of the operation unit 90 is turned on, a driving force of the motor 96 is transmitted from the drive gear 94 to the driven gear 61, the drive shaft 60 interlocking with the driven gear 61 is rotated, and the cutting unit 40 and the support portion 50 which interlock with the drive shaft 60 are rotated. If the cutting unit 40 and the support portion 50 are rotated, the linear motion shaft 70 interlocking with both of these on the distal side is also rotated. The proximal portion of the linear motion shaft 70 is supported by the bearing portion 103. Accordingly, even when being rotated, the cutting unit 40 and the support portion 50 can maintain an expansion state.

Next, in a state where the cutting unit 40 and the support portion 50 are rotated, the treatment device 20 is pushed so as to move forward as illustrated in FIG. 12A. In this manner, the blade 47 formed in the cutting unit 40 comes into contact with the stenosed site S and cut stenosis substances. The stenosis substances are changed to debris D so as to flow to the distal side (downstream side). The debris D flowing to the distal side enters the inside of the filter portion 111 located on the distal side, and is filtered and collected by the filter portion 111. In this manner, the debris D can be prevented from flowing to the peripheral blood vessel. Accordingly, a new stenosed site can be prevented from developing in the peripheral blood vessel.

Then, when the stenosed site S is cut, the maximum expansion portion 53 whose outer diameter is largest in the support portion 50 protrudes radially outward between the struts 41. A portion which expands outward most in the strut 41 and is likely to come into contact with biological tissues is located further radially inward from the maximum expansion portion 53 (refer to FIG. 6A). In this manner, the maximum expansion portion 53 of the support portion 50, which has a lower influence on the biological tissues than the strut 41 comes into contact with the biological tissues. Accordingly, normal biological tissues can be prevented from being damaged by the edge portion of the strut 41, and thus, safety can be improved. In addition, since the blade 47 is not formed in a portion which expands outward most in the strut 41 and which is likely to come into contact with biological tissues, normal biological tissues can be prevented from being damaged, and thus safety can be improved. Furthermore, a portion in the vicinity of the blade 47 of the strut 41 has a short distance from the rotation axis X (diameter is small), and has the wide portion 46 formed therein. Accordingly, the support portion 50 is less likely to protrude radially outward between the struts 41. Therefore, the blade 47 can be brought into contact with the stenosed site S without hindering the support portion 50.

In addition, in the strut 41, the outer peripheral surface having the blade 47 formed therein is deformed so as to tilt radially inward as it goes toward a side in the rotating direction Y (refer to FIG. 6B). Therefore, the strut 41 comes into smooth contact with a contact target such as the stenosed site S, the biological tissues, or the like from a side tilting radially inward in the strut 41. Accordingly, excessive damage to the biological tissues can be reduced. In addition, since the strut 41 is formed by being cut out from a tubular body having a diameter which is smaller than a diameter in the expansion state, the radius of curvature of the outer peripheral surface of the strut 41 is smaller than a distance from the rotation axis X to the outer peripheral surface of the strut 41 in the expansion state. Therefore, the edge portion of the strut 41 becomes further less likely to come into contact with the contact target. Accordingly, excessive damage to the biological tissues can be further reduced.

In addition, the support portion 50 is disposed on the inner side of the strut 41. Accordingly, the dropped hard debris D is less likely to be interposed between the struts 41, and the strut 41 is not rolled up outward. Therefore, the strut 41 can be prevented from being damaged or broken.

In addition, since the strut 41 having the blade 47 formed therein is supported by the support portion 50, a radial force (force acting in the radial direction) increases. Accordingly, regardless of the expandable and contractible structure, improved cutting capability can be demonstrated. In addition, a gap between the struts 41 is complemented by the support portion 50. Accordingly, as a whole, the cross section formed by the strut 41 and the support portion 50 becomes substantially circular, thereby enabling the cutting unit 40 to be centered at a suitable position. In addition, a portion of the debris D cut off and generated by the blade 47 of the strut 41 can be collected into the support portion 50.

After the stenosis substances are completely cut, the switch 98 is turned off, and the rotation of the drive shaft 60 is stopped. Then, if the dial 100 is rotated in reverse as compared to when the cutting unit 40 and the support portion 50 expand, as illustrated in FIG. 1, the feed screw 101 is rotated, the moving base 102 is moved to the distal side, and the linear motion shaft 70 interlocking with the moving base 102 is moved to the distal side. If the linear motion shaft 70 is moved to the distal side, the distal fixed end 42 of the cutting unit 40 moves so as to be separated from the proximal fixed end 43, and the cutting unit 40 and the support portion 50 are brought into a state of contracting radially inward. Thereafter, the outer sheath 80 is moved to the distal side. As illustrated in FIG. 12B, the cutting unit 40 and the support portion 50 are accommodated inside the outer sheath 80, and the treatment device 20 is removed therefrom via the guiding catheter 140.

Next, the proximal end portion of the shaft portion 113 is inserted into the tubular body opening portion 126 of the sheath 120 (suction catheter). As illustrated in FIG. 13A, the sheath 120 is inserted into the blood vessel via the guiding catheter 140. In this state, a Y-connector (not illustrated) is connected to the sheath 120 so as to communicate with the hub opening portion 125 of the sheath 120, and a syringe is connected to an opening portion into which the shaft portion 113 of the Y-connector is not inserted. Thereafter, if a suction force is applied by pulling out a pusher of the syringe, negative pressure is generated inside the lumen 124 extending from the distal side to the proximal side. Accordingly, the debris D inside the filter portion 111 can be pulled into the lumen 124 through the tubular body opening portion 126. When the debris D is aspirated by using the syringe, the tubular body 121 is moved forward and rearward, if necessary. In this manner, the debris D can be aspirated effectively. As described above, the debris D inside the filter portion 111 is partially or completely aspirated, and is pulled into the lumen 124, thereby bringing the filter portion 111 into a state where the filter portion 111 is likely to contract. An instrument (suction catheter) for aspirating the debris D may be a catheter which is different from the sheath 120. In addition, without being limited to the syringe, an instrument for applying a suction force may be a pump, for example.

Next, if the shaft portion 113 is moved to the distal side relative to the sheath 120, as illustrated in FIG. 13B, the filter portion 111 is pulled out by the shaft portion 113, and is moved into the lumen 124 of the tubular body 121.

Thereafter, the filter instrument 110 is removed therefrom together with the sheath 120. The guiding catheter 140 and the introducer sheath are removed therefrom, thereby causing a user to finish manual skills. The filter instrument 110 may not be accommodated in the sheath 120. Instead of using the sheath 120, the filter instrument 110 may be directly accommodated inside the guiding catheter 140. In this case, the debris D may not be aspirated and removed therefrom.

As described above, the medical device 10 according to the first embodiment is a device for cutting substances inside a body lumen. The medical device 10 can include the drive shaft 60 that is rotatable, at least one strut 41 that rotatably interlocks with the distal side of the drive shaft 60, that extends along a rotation axis X, and whose central portion is bent so as to be expandable radially outward, and the support portion 50 that rotatably interlocks with the distal side of the drive shaft 60, that is formed in a mesh shape and a tubular shape while including multiple gaps, at least a portion of which is positioned on a radially inner side of the strut 41, and that is expandable radially outward by a central portion in a direction extending along the rotation axis X being bent. Therefore, the strut 41 and the support portion 50 can be easily delivered into and are caused to expand in the body lumen, thereby enabling a proper cutting range to be secured. Furthermore, according to the medical device 10, the support portion 50 supports the strut 41 from the radially inner side. Accordingly, excessive damage to the biological tissues, which is caused by the edge portion of the strut 41 can be reduced, and substances can be prevented from being caught in the gap between the struts 41. Therefore, it is possible to prevent the device from being damaged or broken.

The strut 41 is configured so that the blade 47 for cutting the substances is formed at a position on the further distal side from the portion which expands most radially outward in an expansion state. Accordingly, the blade 47 is less likely to come into contact with the biological tissues, thereby ensuring safety. The substances can be effectively cut by pressing the strut 41 into the stenosed site S and bringing the blade 47 into contact with the substances inside the body lumen.

In addition, the maximum expansion portion 53 in an expansion state which expands most radially outward from the support portion 50 protrudes radially outward further than the strut 41 from a portion between the struts 41. Accordingly, the maximum expansion portion 53 of the support portion 50, which has a lower influence on the biological tissues than the strut 41 comes into contact with the biological tissues. Therefore, normal biological tissues can be prevented from being damaged by the edge portion of the strut 41, and thus, safety can be improved.

In addition, in the strut 41 in an expansion state, the outer peripheral surface having the blade 47 formed therein tilts radially inward as it goes toward a side in the rotating direction Y. Therefore, the strut 41 comes into smooth contact with a contact target from a side tilting radially inward in the strut 41. Accordingly, excessive damage to the biological tissues, which is caused by the strut 41 can be reduced.

In addition, the strut 41 is configured to have the wide portion 46 whose width in the circumferential direction is relatively wider than that of an adjacent portion, and the wide portion 46 has the blade 47 formed therein. Accordingly, the wide portion 46 prevents the support portion 50 from protruding radially outward. Therefore, the blade 47 can be favorably brought into contact with the contact target without being hindered by the support portion 50.

The length in which the maximum expansion portion 53 in an expansion state protrudes radially outward from the strut 41 is greater than the length in which the support portion 50 protrudes radially outward from a portion between the struts 41 in the portion having the wide portion 46 arranged therein. Accordingly, the maximum expansion portion 53 is brought into contact with the biological tissues, thereby helping prevent normal biological tissues from being damaged by the strut 41. Even so, the blade 47 of the strut 41 is effectively brought into contact with the substances inside the body lumen. Accordingly, the substances can be favorably cut.

The strut 41 is configured to have the tilting portion 44 which tilts to the rotation axis X in a contraction state. Accordingly, the outer peripheral surface of the strut 41 can be set to tilt at a desired angle by using an asymmetric shape of the tilting portion 44 in an expansion state, thereby allowing a further degree of freedom in design. Therefore, the strut 41 can be set to have an angle by which the biological tissues are less likely to be damaged and the substances inside the body lumen can be cut relatively easily. In addition, the tilting portion 44 is disposed on the proximal side of the strut 41. In this manner, a portion on the proximal side of the strut 41 comes into contact with the support portion 50 by using a wide area. Accordingly, the support portion 50 can be prevented from being misaligned with the strut 41.

In addition, according to the present disclosure, a treatment method is disclosed for cutting substances inside a body lumen. The treatment method is adopted by using a medical device including a drive shaft that is rotatable, at least one strut that rotatably interlocks with a distal side of the drive shaft, that extends along a rotation axis, and whose central portion is bent so as to be expandable radially outward, and a support portion that is rotatably connected to the distal side of the drive shaft, that is formed in a mesh shape and a tubular shape while including multiple gaps, at least a portion of which is positioned on a radially inner side of the strut, and that is expandable radially outward by a central portion in a direction extending along the rotation axis being bent. Then, the treatment method can include (i) a step of inserting the strut and the support portion which are in a contraction state into the body lumen, (ii) a step of expanding the strut and the support portion, (iii) a step of cutting the substances inside the body lumen by causing the drive shaft to rotate the strut and the support portion, (iv) a step of contracting the strut and the support portion, and (v) a step of removing the strut and the support portion from the inside of the body lumen. According to the treatment method, the strut and the support portion are inserted into the body lumen so as to be easily delivered into the body lumen, thereby helping enable a proper cutting range to be secured. Furthermore, according to the treatment method, the support portion supports the strut from the radially inner side, and the strut is rotated so as to cut the substances. Accordingly, excessive damage to the biological tissues, which is caused by the edge portion of the strut can be reduced, and substances are prevented from being caught in the gap between the struts. Therefore, the device can be prevented from being damaged or broken.

In addition, according to the above-described treatment method, in the step of expanding the strut and the support portion, the maximum expansion portion, which expands most radially outward from the support portion may protrude radially outward further than the strut from a portion between the struts. In this manner, the maximum expansion portion of the support portion, which has a lower influence on the biological tissues than the strut comes into contact with the biological tissues. Accordingly, normal biological tissues can be prevented from being damaged by the edge portion of the strut, and thus, safety can be improved.

In addition, the above-described treatment method may further include a step of installing the filter portion inside the body lumen before the step of cutting the substances inside the body lumen, a step of causing the filter portion to collect the substances inside the body lumen after the step of cutting the substances inside the body lumen, and a step of removing the filter portion from the inside of the body lumen. In this manner, the substances (debris) which are cut and appeared by the blade of the strut can be collected and removed by the filter portion. Accordingly, a new stenosed site or an occluded site can be prevented from developing in the peripheral blood vessel due to the debris flowing to the peripheral blood vessel.

Second Embodiment

In a medical device 200 according to a second embodiment of the present disclosure, a configuration of the cutting unit 40, the outer sheath 80, and the operation unit 90 is particularly different from that of the first embodiment. The same reference numerals are given to elements having the same function as the first embodiment, and description thereof will be omitted.

Figure 14:
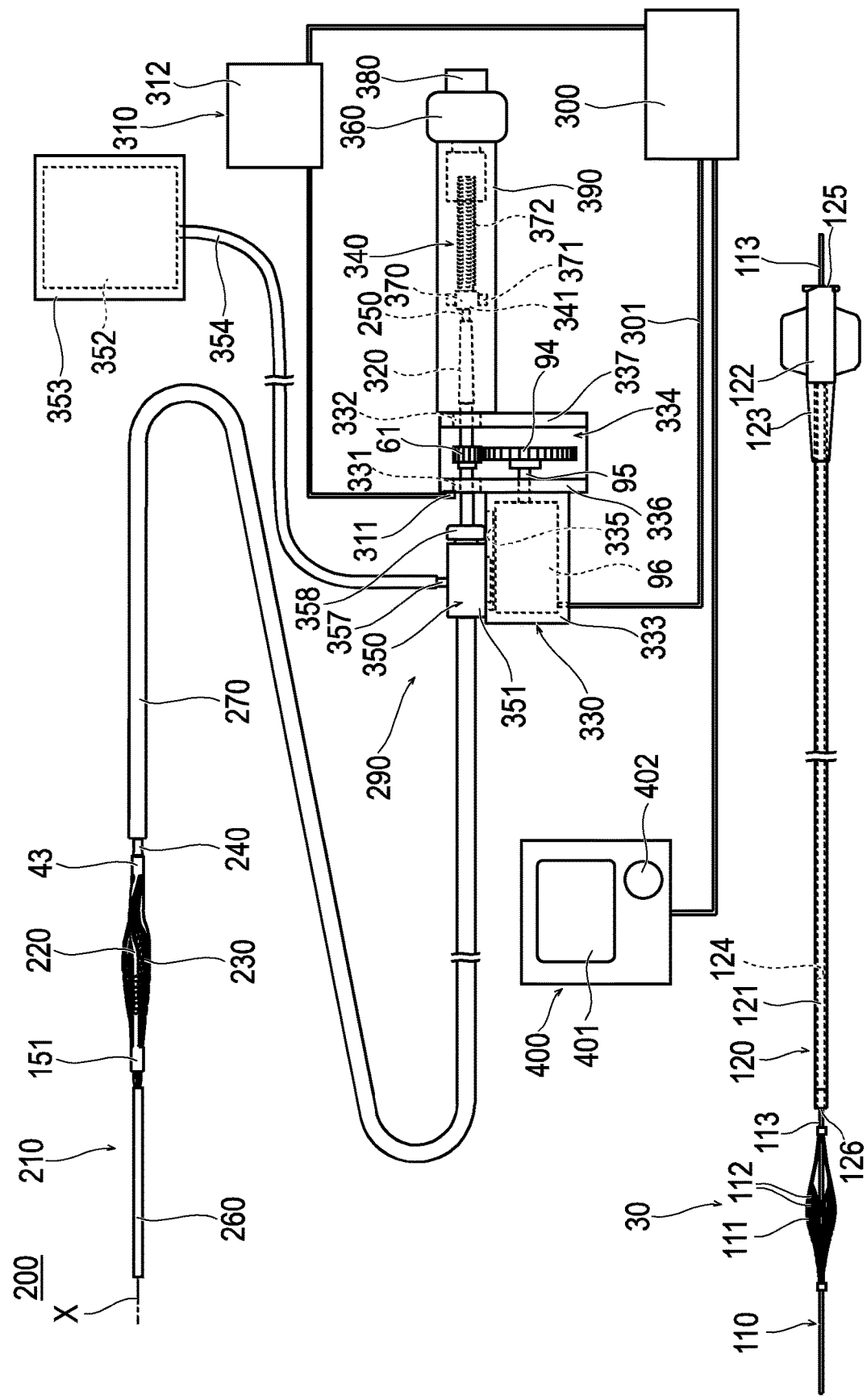
FIG. 14 is a plan view illustrating a state where a cutting unit of a medical device according to a second embodiment contracts.

As illustrated in FIG. 14, the medical device 200 according to the second embodiment of the present disclosure includes a treatment device 210 which cuts a stenosed site or an occluded site, and the filter device 30 which collects debris (substance) which is cut and dropped off from the stenosed site or the occluded site.

Figure 15:
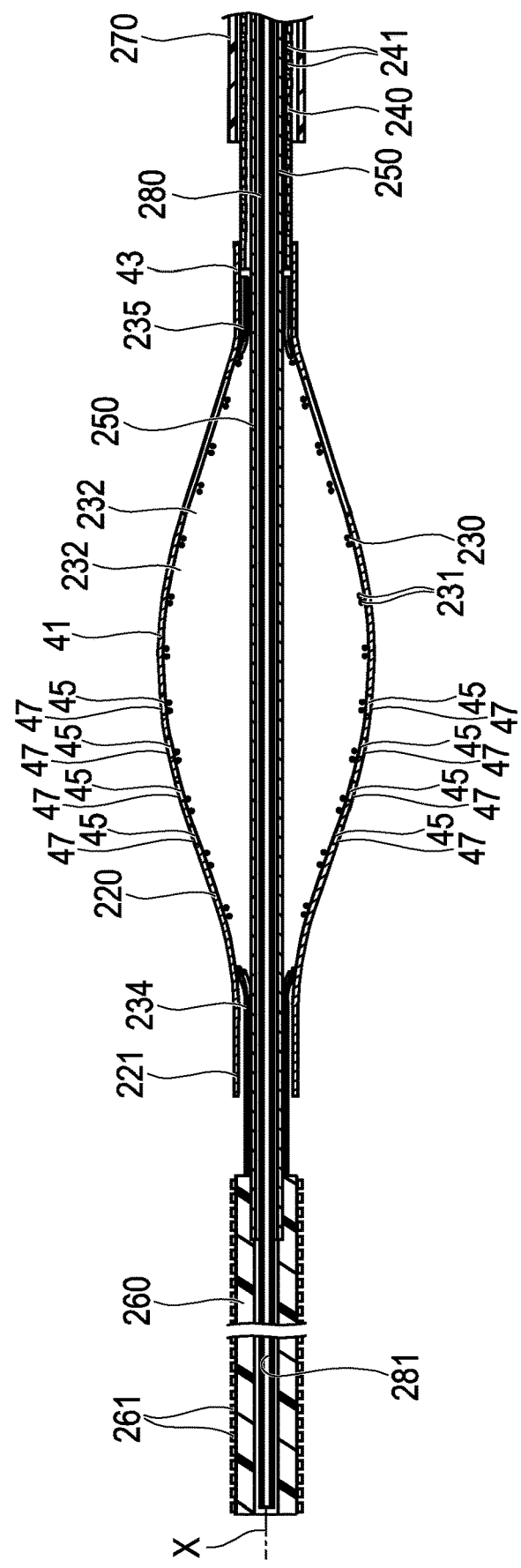
FIG. 15 is a longitudinal sectional view illustrating a distal end portion of the medical device according to the second embodiment.

As illustrated in FIGS. 14 and 15, the treatment device 210 can include a cutting unit 220 which is expandable and contractible radially outward, a support portion 230 which supports the cutting unit 220, a drive shaft 240 which rotates the cutting unit 220, and a linear motion shaft 250 which adjusts a deformation amount of the cutting unit 220. Furthermore, the treatment device 210 can include a distal tube 260 which interlocks with a distal side of the linear shaft 250, an outer sheath 270 which can accommodate the cutting unit 220, an inner tube 280 which is arranged inside the liner motion shaft 250, and an operation unit 290 which is disposed on an operating hand side for operation. Furthermore, the treatment device 210 can include a control unit 300 which controls driving of the drive shaft 240, a pushing/pulling resistance measuring unit 310 (detection unit) which is attached to the drive shaft 240, an interlock portion 320 which interlocks proximal portions of the drive haft 240 and the linear motion shaft 250 with each other, and a notification unit 400 which gives notification that cutting resistance exceeds a threshold value.

The cutting unit 220 can include at least one (four in the present embodiment) strut 41 which extends along the rotation axis X of the drive shaft 240, a tubular distal end portion 221 which is formed integrally with the strut 41 on a distal side of each of the struts 41, and the tubular proximal fixed end 43 which is formed integrally with the strut 41 on a proximal side of each of the struts 41. The distal end portion 221 is not fixed to the support portion 230 and the liner motion shaft 250, and is movable in the axial direction relative to the support portion 230 and the linear motion shaft 250. The distal end portion 221 comes into contact with the proximal portion of the distal tube 260 interlocking with the linear motion shaft 250 by the linear motion shaft 250 moving in a proximal direction with respect to the cutting unit 220 (refer to FIGS. 19A and 19B).

The support portion 230 is arranged so as to support the cutting unit 220 radially inward from the cutting unit 220, and is formed in a tubular shape by braiding multiple wires 231 so as to have a gap 232 between the wires 231. A distal end portion 234 of the support portion 230 is configured so that the multiple wires 231 gather into a tubular shape, and is fixed to the outer peripheral surface of the linear motion shaft 250 without being fixed to an inner side surface of the distal end portion 221 of the cutting unit 220. A proximal end portion 235 of the support portion 230 is configured so that the multiple wires 231 gather into a tubular shape, and is fixed to an inner peripheral surface of the proximal fixed end 43 of the strut 41.

Some of the multiple wires 231 are wires configured to have an X-ray contrast material. In this manner, a position and an expansion diameter of the support portion 230 and the cutting unit 220 can be accurately recognized by using X-ray fluoroscopy, thereby facilitating manual skills. For example, the X-ray contrast materials preferably include gold, platinum, platinum-iridium alloy, silver, stainless steel, molybdenum, tungsten, tantalum, palladium, an alloy thereof or the like. Instead of the support portion 230, a portion of the cutting unit 220 may be configured to have the X-ray contrast material. For example, the inner peripheral surface of the cutting unit 220 may be covered with the X-ray contrast material by means of plating. In this manner, the position and the expansion diameter of the support portion 230 and the cutting unit 220 can be accurately recognized by using X-ray fluoroscopy, thereby further facilitating manual skills.

If the distal end portion 234 and the proximal end portion 235 are moved close to each other, the support portion 230 can shift from a contraction state (refer to FIG. 15) where the support portion 230 has a tubular shape having a substantially uniform outer diameter to an expansion state (refer to FIGS. 19A and 19B) where the support portion 230 is deformed so that a central portion of the support portion 230 is bent radially outward. If the central portion of the support portion 230 is bent radially outward, the distal end portion 234 gradually moves close to the distal tube 260, and the strut 41 arranged on the outer side of the support portion 230 is pressed and expands radially outward by the support portion 230. Until the distal tube 260 comes into contact with the distal end portion 234, as illustrated in FIG. 19A, the distal end portion 221 is not fixed to the support portion 230 and the linear motion shaft 250. Accordingly, a force in the axial direction hardly acts between the distal end portion 221 and the proximal fixed end 43. The cutting unit 220 expands by only a force acting radially outward which is received from the support portion 230. Therefore, a gap is less likely to occur between the strut 41 and the wires 231, and thus, stenosis substances or debris are not interposed between the strut 41 and the wires 231. Accordingly, the strut 41 can be prevented from being damaged, and normal biological tissues can be prevented from being damaged by the edge portion of the strut 41. If the distal tube 260 moving together with the linear motion shaft 250 comes into contact with the distal end portion 221, as illustrated in FIG. 19B, the distal end portion 221 receives a force in the proximal direction from the distal tube 260, and a force of contracting the distal end portion 221 in the axial direction acts on the distal end portion 221. In this manner, the strut 41 expands not only by the force acting radially outward which is received from the support portion 230, but also by the contraction force. Therefore, while a desirable state is maintained where a gap is less likely to occur between the strut 41 and the wires 231, the support portion 230 can be prevented from pressing the cutting unit 220 more than necessary.

Figure 16:
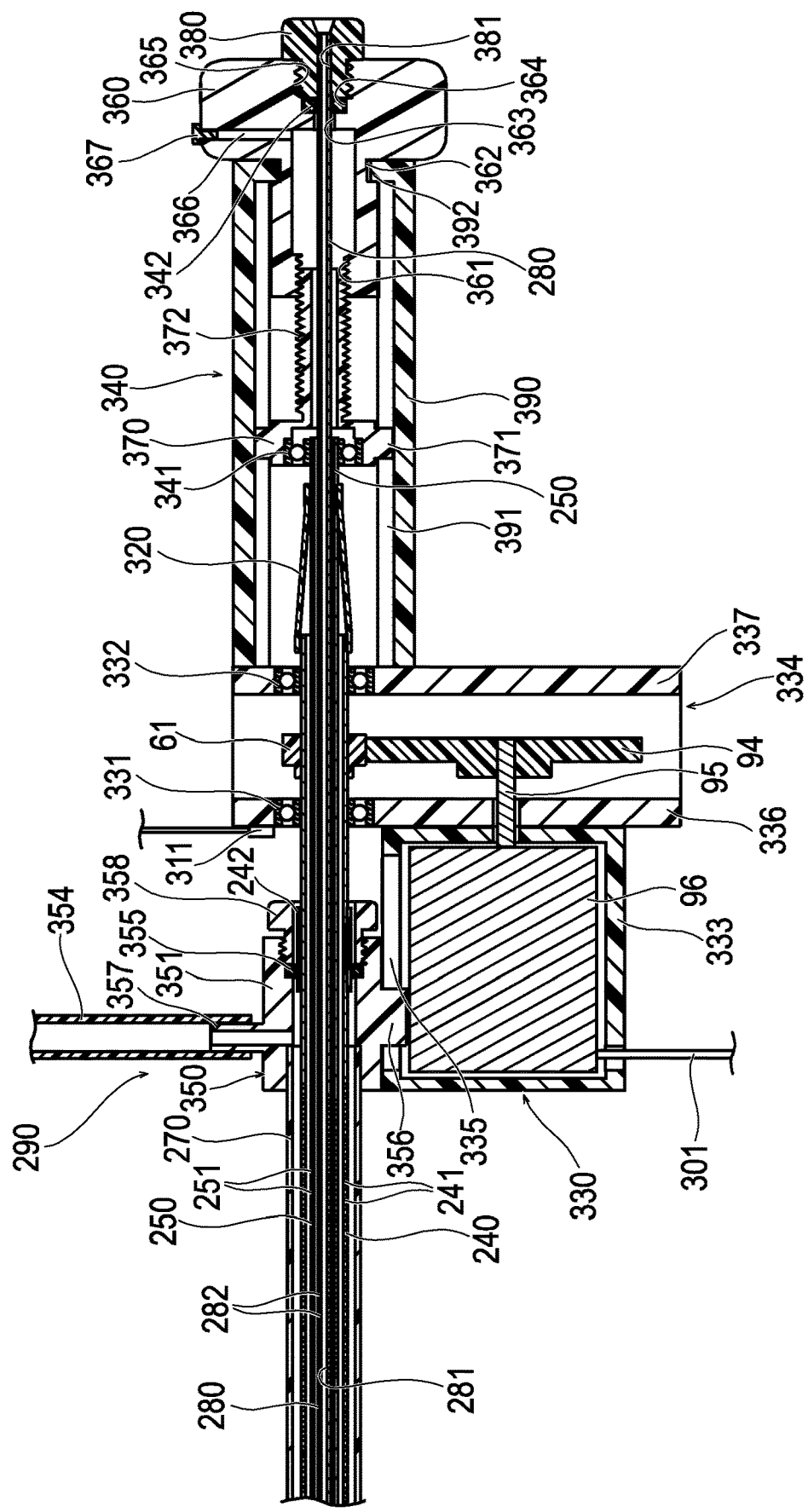
FIG. 16 is a longitudinal sectional view illustrating a proximal portion of a treatment device according to the second embodiment.

As illustrated in FIGS. 15 and 16, the drive shaft 240 is formed in a tubular shape. The distal side is fixed to the proximal fixed end 43 of the cutting unit 220, and the driven gear 61 is fixed to the proximal side. Multiple hole portions 241 through which a fluid can be circulated are formed to penetrate the outer peripheral surface from the inner peripheral surface in at least a portion of the drive shaft 240. A portion of the outer peripheral surface of the proximal portion of the drive shaft 240 is covered with a cover portion 242 for decreasing a frictional force by coming into slidable contact with a first sealing portion 355 inside the operation unit 290.

Figure 17:
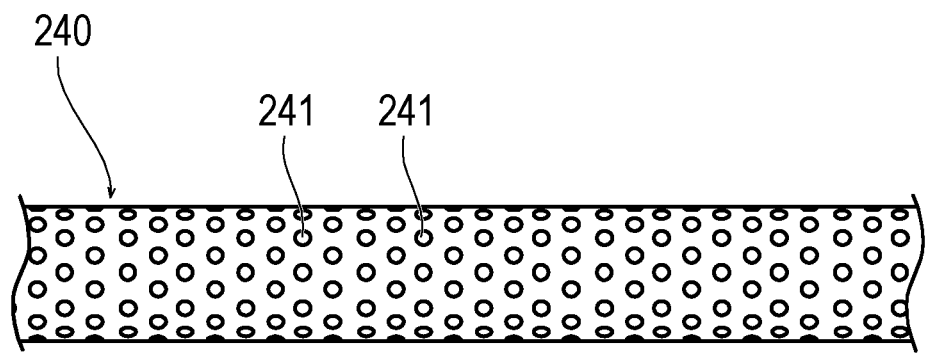
FIG. 17 is a plan view illustrating a drive shaft according to the second embodiment.
Figure 18:
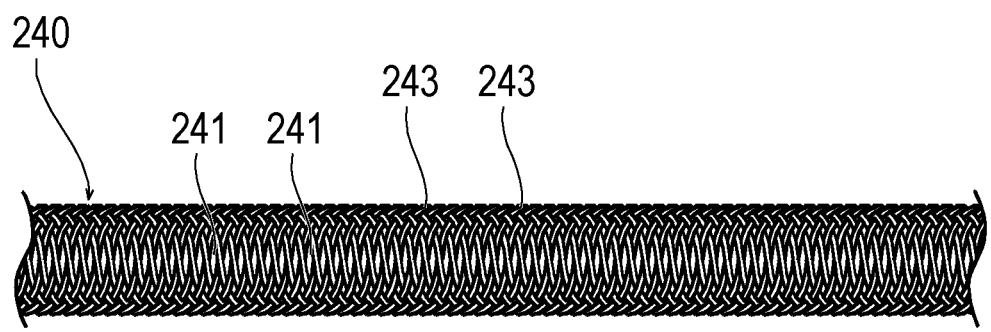
FIG. 18 is a plan view illustrating another example of the drive shaft according to the second embodiment.

A configuration material of the cover portion 242 is preferably low friction material, and is a fluorine-based resin material such as polytetrafluoroethylene (PTFE) or the like. As illustrated in FIG. 17, the hole portions 241 of the drive shaft 240 may be configured to serve as multiple through-holes disposed in the tubular body. Alternatively, as illustrated in FIG. 18, the hole portions 241 may be configured to include a gap formed from a braided body of braided wires 243. In addition, the drive shaft 240 may be configured to include coils so that the hole portions 241 are gaps of the coils. The hole portions 241 may be entirely or partially formed in the drive shaft 240. When the drive shaft 240 in which the hole portions 241 are disposed in a predetermined range is formed by using the braided body or the coils, the braided body or the coils which have gaps are partially covered with a material such as a resin or the like. In this manner, the drive shaft 240 can be easily formed.

As illustrated in FIGS. 15 and 16, the linear motion shaft 250 is a tubular body which can move in the direction of the rotation axis X relative to the drive shaft 240 in order to expand and contract the cutting unit 220 and the support portion 230. The linear motion shaft 250 penetrates the drive shaft 240, the cutting unit 220, and the support portion 230. In the linear motion shaft 250, a distal side of the linear motion shaft 250 is fixed to the distal end portion 234 of the wire 231, and a proximal side of the distal end portion 234 is connected to a moving mechanism 340, which linearly moves the linear motion shaft 250 along the rotation axis X. The proximal side of the linear motion shaft 250 further protrudes to the proximal side from the drive shaft 240. Multiple hole portions 251 through which a fluid can be circulated are formed to penetrate the outer peripheral surface from the inner peripheral surface in at least a portion of the linear motion shaft 250. Similarly to the hole portions 241 of the drive shaft 240, the hole portions 251 of the linear motion shaft 250 may be configured to serve as multiple through-holes disposed in the tubular body. Alternatively, the hole portions 251 may be configured to include gaps of a threaded body or coils.

The interlock portion 320 is a tubular expandable and contractible member which interlocks with the proximal portion of the linear motion shaft 250 and the proximal portion of the drive shaft 240 to each other, and a diameter of the interlock portion 320 decreases in a tapered shape in the proximal direction. The interlock portion 320 interlocks with the linear motion shaft 250 and the drive shaft 240 in a liquid-tight manner. The interlock portion 320 maintains liquid-tightness between the linear motion shaft 250 and the drive shaft 240 in the operation unit 290, and allows the linear motion shaft 250 to move to the drive shaft 240 in the axial direction. The linear motion shaft 250 and the drive shaft 240 which are relatively moved interlock with each other by the expandable and contractible interlock portion 320. Accordingly, it is not necessary to employ a sealing structure such as an O-ring or the like which causes friction. Without losing the driving force, the liquid-tightness between the linear motion shaft 250 and the drive shaft 240 can be maintained. In addition, the interlock portion 320 is twisted, thereby enabling the linear motion shaft 250 and the drive shaft 240 to be aligned with each other in the rotating direction.

A configuration material of the interlock portion 320 is not particularly limited as long as the material is expandable and contractible. However, for example, various rubber materials such as natural rubber, isoprene rubber, butadiene rubber, chloroprene rubber, silicone rubber, fluorine rubber, styrene-butadiene rubber and the like; various thermoplastic elastomers such as styrene-based, polyolefin-based, polyurethane-based, polyester-based, polyimide-based, polybutadiene-based, trans-polyisoprene-based, fluororubber-based, chlorinated polyethylene-based elastomers, and the like; or the like can be preferably used.

The outer sheath 270 is a tubular body for covering the outer side of the drive shaft 240, and is movable in the direction extending along the rotation axis X. The outer sheath 270 is operable by gripping the proximal portion. The outer sheath 270 can internally accommodate the cutting unit 220 and the support portion 230 in a contraction state by being moved to the distal side. The cutting unit 220 and the support portion 230 can be exposed outward by moving the outer sheath 270 to the proximal side.

The inner tube 280 is arranged inside the linear motion shaft 250, and is a tubular body which internally has a lumen 281 into which the filter device 30, a guidewire, or the like can be inserted. The inner tube 280 is movable to the linear motion shaft 250 in the direction extending along the rotating direction X. Multiple hole portions 282 through which a fluid can be circulated are formed to penetrate the outer peripheral surface from the inner peripheral surface in at least a portion of the inner tube 280. Similarly to the hole portions 241 of the drive shaft 240, the hole portions 282 of the inner tube 280 may be configured to serve as multiple through-holes disposed in the tubular body. Alternatively, the hole portions 282 may be configured to include gaps of a threaded body or coils.

The distal tube 260 is fixed to the distal side of the linear motion shaft 250. The inner tube 280 is arranged inside the distal tube 260. Multiple convex portions 261 can be formed on the outer peripheral surface of the distal tube 260. For example, the convex portions 261 can be formed by means of embossing, or can be formed by disposing multiple holes. Alternatively, the convex portions 261 can be formed by attaching fine metal powder or the like to the surface of the distal tube 260, or can be formed by mixing the material of the distal tube 260 with the fine metal powder or the like. For example, as the material of the metal powder, stainless steel or the like can be preferably used.

As illustrated in FIG. 14, the pushing/pulling resistance measuring unit 310 (detection unit) can include a sensor 311 for detecting pushing/pulling resistance (resistance in the axial direction) acting on the drive shaft 240 when the cutting unit 220 and the support portion 230 are pushed to and pulled out from a stenosed site, and a measuring device 312 which calculates the pushing/pulling resistance by receiving a signal from the sensor 311. For example, the sensor 311 is a strain gauge attached in the vicinity of a first bearing portion 331 which receives the pushing/pulling resistance. The measuring device 312 can calculate the pushing/pulling resistance, based on the signal received from the sensor 311, and transmits the result to the control unit 300. A portion to which the sensor 311 is attached is not particularly limited as long as the pushing/pulling resistance of the drive shaft 240 can be detected.

As illustrated in FIGS. 14 and 16, the operation unit 290 includes a drive mechanism 330 which provides the drive shaft 240 with a rotating force, a moving mechanism 340 which moves the linear motion shaft 250 along the rotation axis X, and a liquid supply unit 350 which supplies a physiological salt solution or the like into the outer sheath 270.

The liquid supply unit 350 can include a first housing 351 to which the outer sheath 270 is fitted, a container bag 352 which contains the physiological slat solution, a pressurizing bag 353 for pressurizing the container bag 352, a connection tube 354 which connects the container bag 352 and the first housing 351 to each other, a first sealing portion 355 which is arranged inside the first housing 351, and a fixing portion 358 for fixing the first sealing portion 355.

The first housing 351 is a tubular member, and is movable to a second housing 333 in the axial direction while a second cam portion 356 which is slidably fitted to a second cam groove 335 formed in the second housing 333 in which the motor 96 is accommodated is formed on the outer peripheral surface of the first housing 351. The outer sheath 270 is fitted and fixed to the first housing 351 from the distal side. For example, the first sealing portion 355 is an O-ring or an X-ring, is arranged inside the proximal portion of the first housing 351, and comes into slidable contact with the cover portion 242 on the outer peripheral surface of the drive shaft 240 entering the inside of the first housing 351 after passing through the inside of the outer sheath 270. The first sealing portion 355 is fixed by the fixing portion 358 twisted into the first housing 351 from the proximal side. The first sealing portion 355 allows the drive shaft 240 to rotate and to move in the axial direction, and maintains liquid-tightness between the drive haft 240 and the first housing 351.

In addition, a port portion 357 to which the connection tube 354 extending from the container bag 352 is connected is formed in the first housing 351. The physiological salt solution supplied from the container bag 352 can flow into the first housing 351 through the port portion 357. The pressurized physiological salt solution flowing into the first housing 351 can flow into the outer sheath 270 on the distal side, since the flow to the proximal side is regulated by the first sealing portion 355.

The drive mechanism 330 can include the drive gear 94 which meshes with the driven gear 61, the motor 96 which serves as a drive source including the rotary shaft 95 to which the drive gear 94 is fixed, the control unit 300 which controls current supply to the motor 96, and the first bearing portion 331 and the second bearing portion 332 which rotatably support the linear motion shaft 250. Furthermore, the drive mechanism 330 includes the second housing 333 which accommodates the motor 96, and a frame body 334 which interlocks with the second housing 333 and which holds the first bearing portion 331 and the second bearing portion 332.

As described above, the second housing 333 is a box-shaped member which accommodates the motor 96. The second cam groove 335 to which the second cam portion 356 of the first housing 351 is slidably fitted is formed on an outer surface of the second housing 333.

The frame body 334 can include a first partition wall 336 and a second partition wall 337 which are parallel to each other. The second housing 333 is fixed to the first partition wall 336 on the distal side, and the moving mechanism 340 is fixed to the second partition wall 337 on the proximal side.

The rotary shaft 95 extending from the motor 96 inside the second housing 333 penetrates the first partition wall 336, and the drive gear 94 is arranged between the first partition wall 336 and the second partition wall 337. In addition, the first bearing portion 331 is arranged on the first partition wall 336, and the drive shaft 240 extending from the first housing 351 is rotatably held by the first bearing portion 331. The driven gear 61 fixed to the drive shaft 240 is located between the first partition wall 336 and the second partition wall 337, and meshes with the drive gear 94. The second bearing portion 332 which rotatably supports the drive shaft 240 is arranged on the second partition wall 337.

If power is supplied to the motor 96 via a cable 301 and the rotary shaft 95 of the motor 96 is rotated, the driven gear 61 meshing with the drive gear 94 is rotated, and the drive shaft 240 supported by the first bearing portion 331 and the second bearing portion 332 is rotated. If the drive shaft 240 is rotated, the cutting unit 220, the support portion 230, and the distal tube 260 which are fixed to the distal side of the drive shaft 240 are rotated. The distal end portion 234 of the support portion 230 is joined to the linear motion shaft 250. Accordingly, if the support portion 230 is rotated, the linear motion shaft 250 is also rotated so as to follow the support portion 230.

The moving mechanism 340 can include a dial 360 which can be rotated by an operator's finger, a moving base 370 which is linearly movable by rotating the dial 360, a third bearing portion 341 which is fixed to the moving base 370 and which rotatably supports the linear motion shaft 250, a second sealing portion 342, and a proximal fixing portion 380 which fixes the second sealing portion 342. Furthermore, the moving mechanism 340 can include a third housing 390, which can accommodate the moving base 370. A first cam groove 391 to which a first cam portion 371 formed to protrude in the moving base 370 is slidably fitted is formed on an inner surface of the third housing 390.

The dial 360 is a cylindrical member arranged on the proximal side of the frame body 334, and is rotatable by operating the outer peripheral surface with a finger. In the dial 360, a portion of the distal end portion is located inside the third housing 390. A groove portion 362 extending in the circumferential direction is formed on the outer peripheral surface of the dial 360. A hook portion 392 formed in the proximal portion of the third housing 390 is fitted to the groove portion 362, thereby restricting the movement of the dial 360 in the axial direction. The dial 360 is held so as to be rotatable with respect to the third housing 390. A feed screw 361 screwed to a screw groove 372 formed in the moving base 370 is formed on an inner peripheral surface of the dial 360. A discharge hole 366 for discharging internal air during priming is formed in the dial 360. The discharge hole 366 can be opened and closed by a stopper 367.

The moving base 370 has the first cam portion 371 fitted to the first cam groove 391 of the third housing 390, and the screw groove 372 to which the feed screw 361 is screwed. Therefore, if the feed screw 361 is rotated, the moving base 370 is not rotatable with respect to the third housing 390, and is linearly movable along the rotation axis X. The third bearing portion 341, which is fixed to the moving base 370 applies a moving force to the linear motion shaft 250 in response to the movement of the moving base 370. Accordingly, it is preferable to use a bearing which can receive force acting in the axial direction (thrust force). Another sealing member may be disposed on the proximal side of the third bearing portion 341.

The second sealing portion 342 can be accommodated in a concave portion 364 formed so as to surround a through-hole 363 through which the linear motion shaft 250 of the dial 360 penetrates on the proximal side of the dial 360. The second sealing portion 342 is an annular member, which comes into contact with the outer peripheral surface of the proximal portion of the linear motion shaft 250 located inside of the second sealing portion 342.

The proximal fixing portion 380 can be a bolt-shaped member which can be twisted so as to be screwed to the screw groove 365 formed in the concave portion 364 of the dial 360. The proximal fixing portion 380 internally has a through-hole 381 in which the inner tube 280 is arranged. The proximal fixing portion 380 is twisted into the concave portion 364 of the dial 360, thereby deforming the second sealing portion 342 and pressing the inner tube 280. In this manner, the proximal fixing portion 380 maintains a liquid-tight state between the dial 360 and the inner tube 280, and holds the inner tube 280.

The control unit 300 supplies a current to the motor 96 via the cable 301, functions as a detection unit which detects a change in the supplied current, and can detect cutting resistance (resistance in the rotating direction) in the cutting unit 220 which is rotatably driven by the motor 96. In addition, from the measuring device 312, the control unit 300 receives a measured result of pushing/pulling resistance (resistance in the axial direction) acting on the drive shaft 240. If the cutting resistance exceeds a preset threshold value, the control unit 300 stops the rotation of the motor 96, and causes the notification unit 400 to display that the cutting resistance exceeds the threshold value. When the cutting resistance exceeds the threshold value, the control unit 300 may decelerate the rotation speed, instead of stopping the rotation of the motor 96. Furthermore, when the pushing/pulling resistance exceeds a preset threshold value, the control unit 300 stops the rotation of the motor 96, and causes the notification unit 400 to display that the cutting resistance exceeds the threshold value. When the pushing/pulling resistance exceeds the threshold value, the control unit 300 may decelerate the rotation speed, instead of stopping the rotation of the motor 96.

The notification unit 400 can include a monitor 401 and a speaker 402 which are connected to the control unit 300 so as to be communicable therebetween. The monitor 401 notifies an operator by displaying that the cutting resistance or the pushing/pulling resistance exceeds the threshold value. The speaker 402 uses sound in order to notify the operator of the fact that the cutting resistance or the pushing/pulling resistance exceeds the threshold value. When the cutting resistance or the pushing/pulling resistance exceeds the threshold value, the control unit 300 may not stop the rotation of the motor 96, and may cause the notification unit 400 only to issue a notification to the operator. In this case, the operator receives the notification from the notification unit 400 visibly or audibly. In this manner, the operator can stop the motor 96, can stop pushing or pulling, or can change a diameter of the cutting unit 220 by rotating the dial 360.

Next, a method of using the medical device 200 according to the second embodiment will be described by exemplifying a case where stenosis substances inside the blood vessel are cut. A method used until the filter instrument 110 is installed is the same as the method described in the first embodiment.

First, similarly to the method described in the first embodiment, an introducer sheath (not illustrated) is percutaneously inserted into the blood vessel on a further upstream side (proximal side) from the stenosed site S in the blood vessel. The guidewire 130 is inserted into the blood vessel, and is caused to reach the proximal side of the stenosed site S via the introducer sheath. Thereafter, as illustrated in FIG. 8B, the guiding catheter 140 is inserted into the blood vessel along the guidewire 130 so as to reach the proximal side of the stenosed site S.

Next, the support catheter 150 is pushed to move forward to the proximal side of the stenosed site S along the guidewire 130. Thereafter, as illustrated in FIG. 9A, the support catheter 150 and the guidewire 130 are caused to reach the further distal side from the stenosed site S. Thereafter, the guidewire 130 is removed therefrom in a state where the support catheter 150 remains inside the blood vessel.

Then, the filter device 30 in which the filter instrument 110 is accommodated inside the sheath 120 is prepared. The filter portion 111 is arranged at a position close to the distal end portion of the tubular body 121 of the sheath 120, and a shape of the filter portion 111 is restricted to a contraction state. Then, as illustrated in FIG. 9B, the filter device 30 is inserted into the blood vessel via the support catheter 150 so as to reach the further distal side from the stenosed site S. Thereafter, the support catheter 150 is removed therefrom.

Next, the sheath 120 is moved to the proximal side relative to the filter instrument 110 so that the filter portion 111 protrudes to the distal side from the tubular body 121. In this manner, as illustrated in FIG. 10A, the filter portion 111 is brought into an expansion state by using its own restoring force. An outer peripheral portion of the filter portion 111 which is shaped into a cage comes into contact with an inner wall surface of the blood vessel. At this time, the filter portion 111 is open toward the stenosed site S on the upstream side (proximal side). Thereafter, the sheath 120 is removed therefrom by leaving the filter instrument 110 behind.

Figure 20:
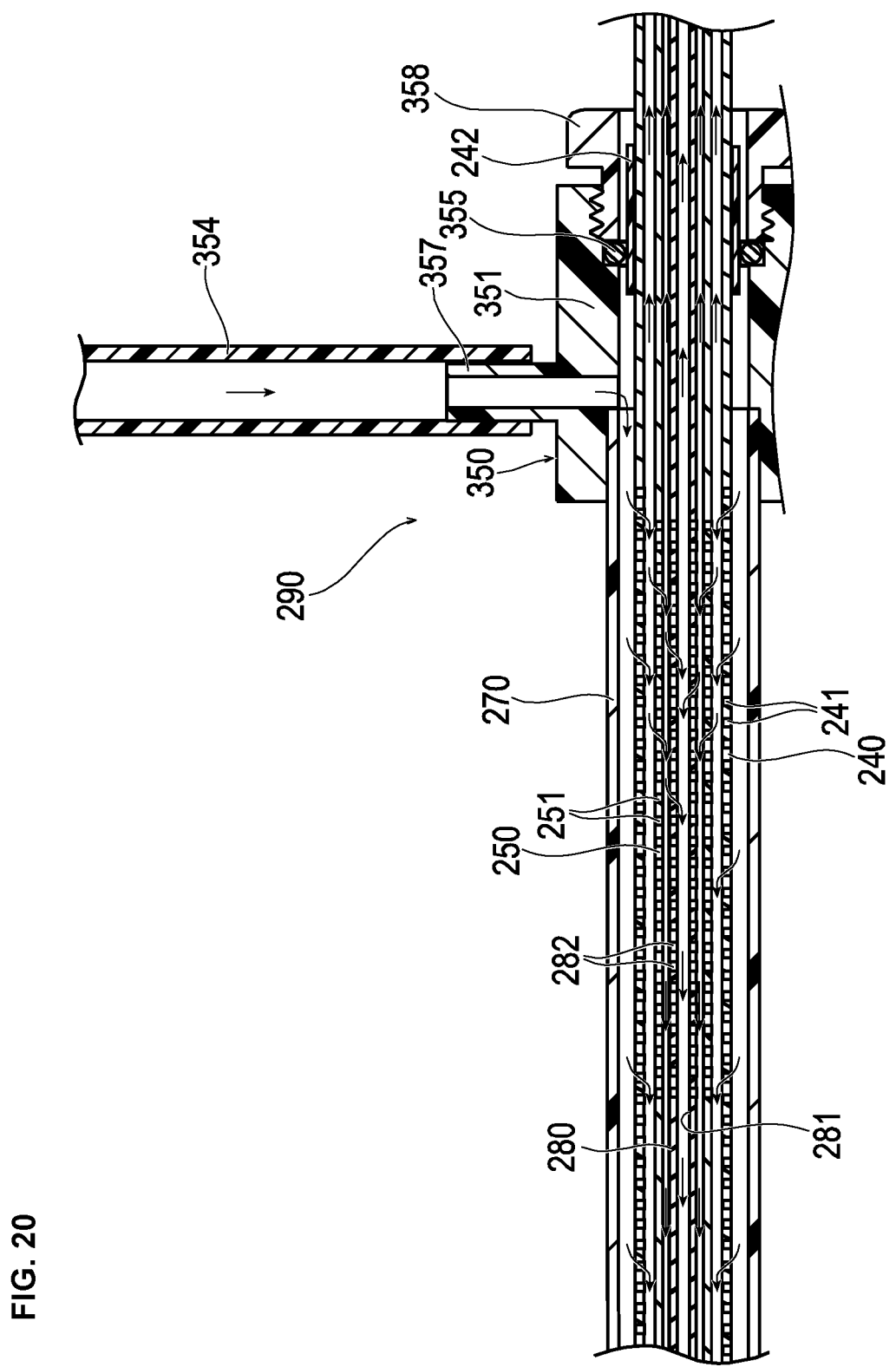
FIG. 20 is a longitudinal sectional view illustrating a liquid supply unit according to the second embodiment.

Next, the treatment device 210 in a state where the cutting unit 220 and the support portion 230 contracts and are accommodated inside the outer sheath 270 is prepared. The container bag 352 is pressurized by the pressurizing bag 353, and a physiological salt solution is supplied into the first housing 351 from the container bag 352 via the connection tube 354. As illustrated in FIG. 20, the physiological salt solution flowing into the first housing 351 moves in the distal direction through the inside of the outer sheath 270, since the movement in the proximal direction is restricted by the first sealing portion 355. If the physiological salt solution flowing into the outer sheath 270 reaches a region where the hole portion 241 of the drive shaft 240 is formed, a portion of the physiological salt solution passes through the hole portion 241, and flows into the drive shaft 240. If the physiological salt solution flowing into the drive shaft 240 reaches a region where the hole portion 251 of the linear motion shaft 250 is formed, a portion of the physiological salt solution passes through the hole portion 251, and flows into the linear motion shaft 250. If the physiological salt solution flowing into the linear motion shaft 250 reaches a region where the hole portion 282 of the inner tube 280 is formed, a portion of the physiological salt solution passes through the hole portion 282, and flows into the lumen 281 of the inner tube 280.

Figure 21:
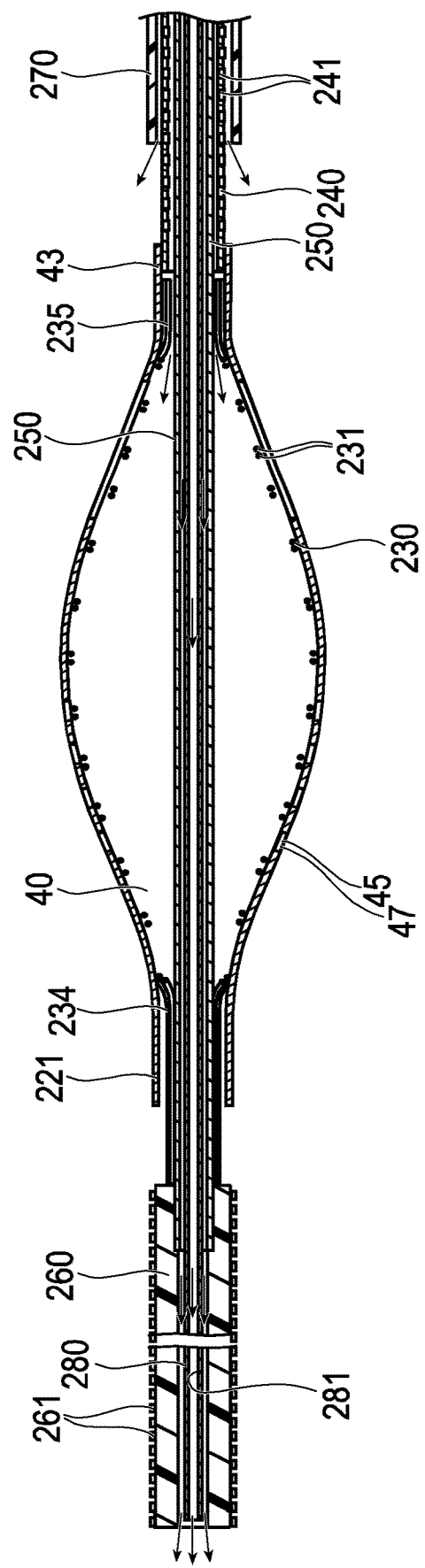
FIG. 21 is a longitudinal sectional view illustrating the distal end portion of the treatment device according to the second embodiment when priming is performed.
Figure 22:
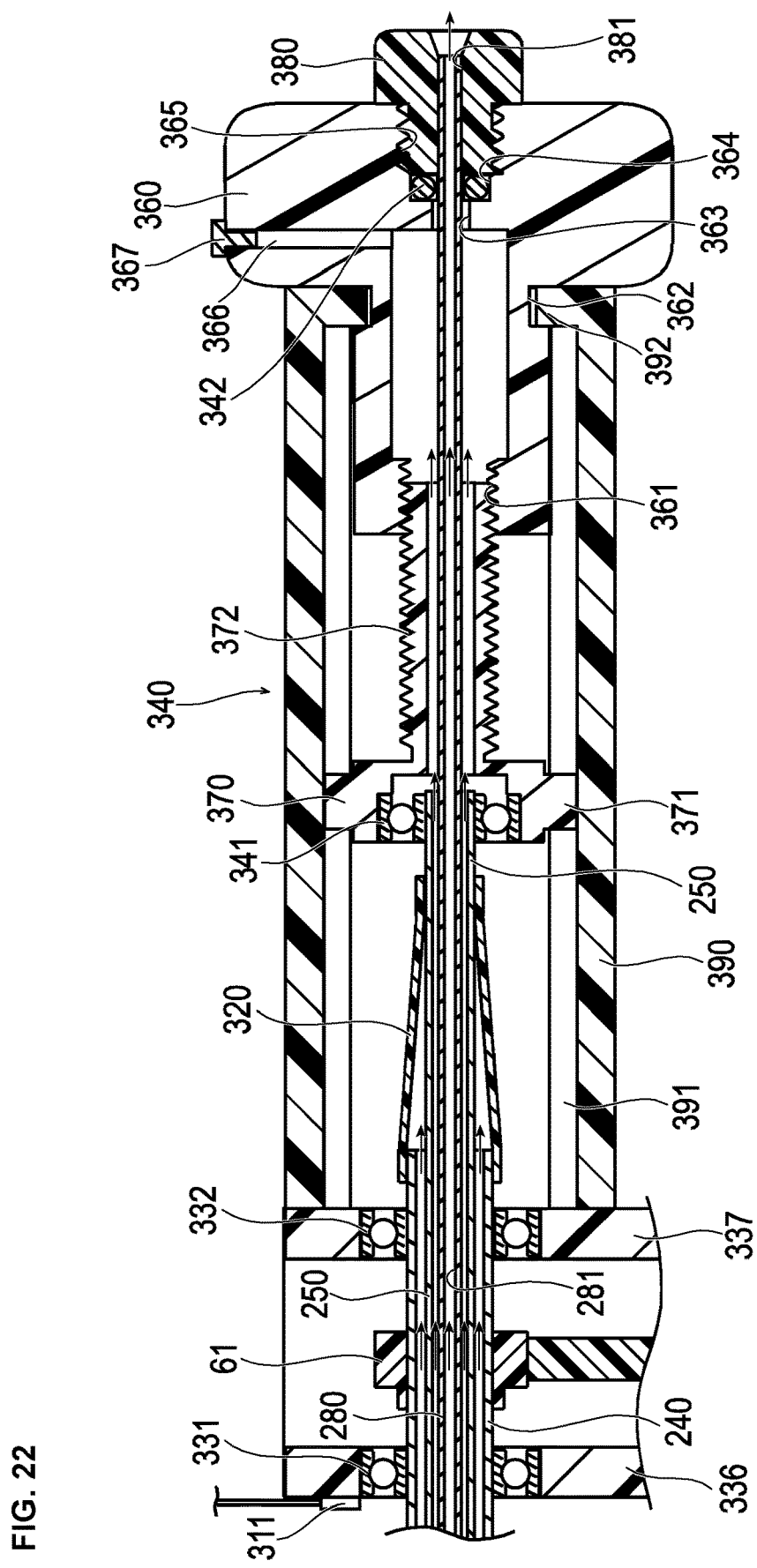
FIG. 22 is a longitudinal sectional view illustrating the proximal portion of the treatment device according to the second embodiment when the priming is performed.

Then, as illustrated in FIG. 21, the physiological salt solution flowing into the outer sheath 270, into the drive shaft 240, into the linear motion shaft 250, and into the inner tube 280 is discharged from the outer sheath 270, the drive shaft 240, the linear motion shaft 250, and the opening portion on the distal side of the inner tube 280. Furthermore, as illustrated in FIG. 22, the movement of the physiological salt solution flowing into the drive shaft 240 is restricted by the interlock portion 320 interlocking with the proximal portion of the drive shaft 240 and the linear motion shaft 250. The physiological salt solution flowing into the linear motion shaft 250 flows in the proximal direction, passes through the inside of the moving base 370, and flows into the dial 360. The physiological salt solution flowing into the dial 360 is discharged outward through the discharge hole 366. After the air inside the moving base 370 and the air inside the dial 360 are discharged, the stopper 367 can close the discharge hole 366. The physiological salt solution flowing into the inner tube 280 flows in the proximal direction, and is discharged outward from the opening portion on the proximal side. In this manner, priming is completed. Even after the priming is completed, liquid is continuously supplied from the container bag 352 until manual skills using the treatment device 210 are finished. In addition, the priming of the treatment device 210 may be performed without using the pressurizing bag 353.

Figure 23A:
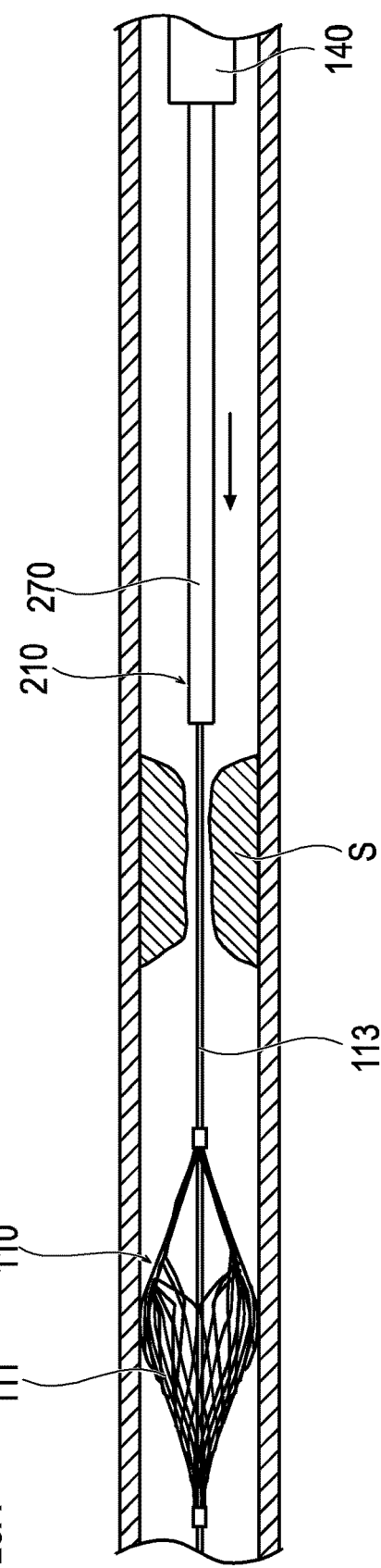
FIG. 23A is a schematic sectional view illustrating an intravascular state when manual skills are used in a state when the treatment device is inserted into the blood vessel.

Next, the proximal end portion of the shaft portion 113 is inserted into the distal side opening portion of the inner tube 280. As illustrated in FIG. 23A, the distal end portion of the treatment device 210 is caused to reach the inside of the blood vessel via the guiding catheter 140. Then, the distal end portion of the treatment device 210 is located on the proximal side of the stenosed site S by using X-ray fluoroscopy. Since the physiological salt solution is always supplied to the treatment device 210 by the container bag 352, the blood is prevented from flowing into the outer sheath 270, the drive shaft 240, the linear motion shaft 250, and the inner tube 280.

Figure 23B:
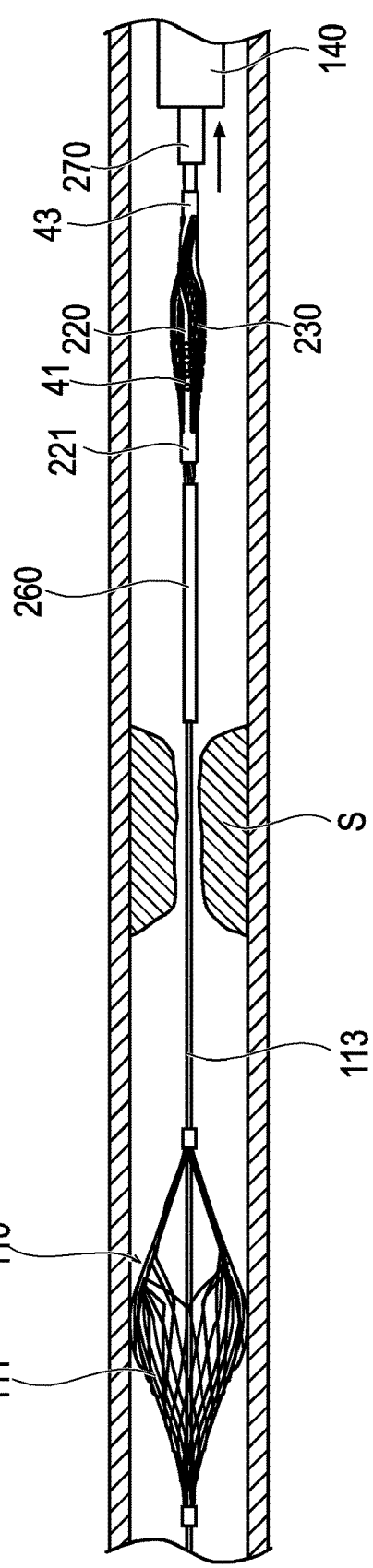
FIG. 23B is a schematic sectional view illustrating an intravascular state when manual skills are used in a state when the cutting unit and the support portion of the treatment device are exposed.
Figure 24:
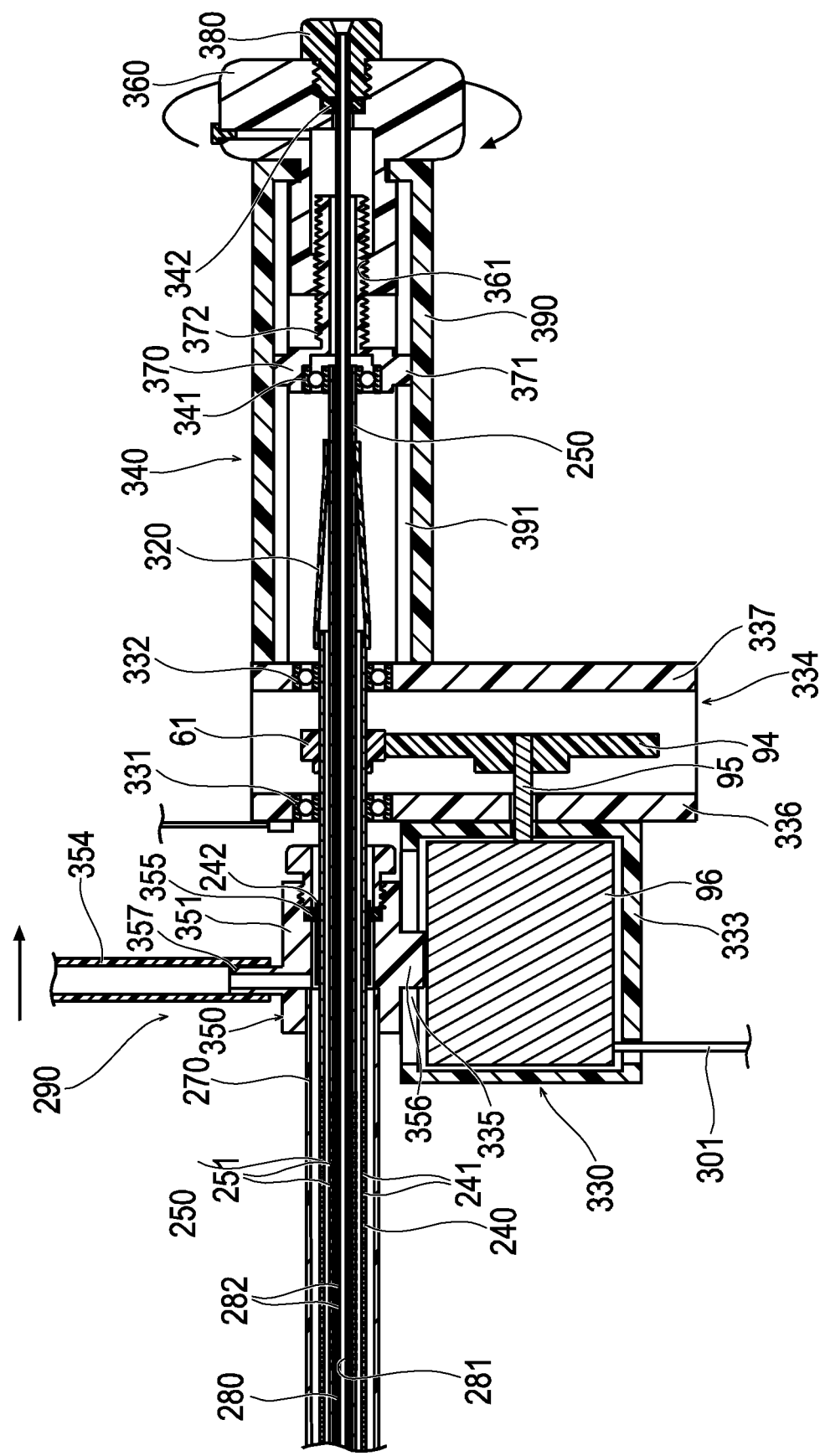
FIG. 24 is a longitudinal sectional view illustrating the proximal portion when a dial of the treatment device according to the second embodiment is rotated.

Next, if the first housing 351 is moved to the proximal side with respect to the second housing 333 as illustrated in FIG. 24, the outer sheath 270 is moved to the proximal side as illustrated in FIG. 23B, and the cutting unit 220 and the support portion 230 are exposed inside the blood vessel. This state indicates a state where the cutting unit 220 and the support portion 230 contract on the further proximal side from the stenosed site S.

Next, a gap size of the stenosed site S is detected by using the X-ray fluoroscopy. The gap size of the stenosed site S can be detected by viewing the gap size from X-ray imaged video, or can be detected by comparing a gap of the stenosed site S in the X-ray imaged video with a dimension-recognizable portion of the treatment device 210, for example (for example, the strut 41 or the support portion 230). In addition, the gap size of the stenosed site S can be detected in more detail by utilizing intravascular ultrasound (IVUS), optical coherence tomography (OCT), or optical frequency domain imaging (OFDI).

Thereafter, as illustrated in FIG. 24, if the dial 360 is rotated, the feed screw 361 is rotated, the moving base 370 is moved to the proximal side, and the linear motion shaft 250 interlocking with the moving base 370 is moved to the proximal side with respect to the drive shaft 240. If the linear motion shaft 250 is moved to the proximal side, the distal end portion 234 and the proximal end portion 235 move close to each other. As illustrated in FIGS. 19A, 19B, and 25A, the central portion of the support portion 230 is deformed so as to be bent radially outward, and is brought into an expansion state. If the central portion of the support portion 230 is bent radially outward, the strut 41 arranged on the radially outer side of the support portion 230 is pressed and expands radially outward by the support portion 230. In this case, at least when the expansion starts, the distal end portion 221 of the cutting unit 220 is not fixed to the support portion 230 and the linear motion shaft 250. Accordingly, force acting in the axial direction does not act between the distal end portion 221 and the proximal fixed end 43. As illustrated in FIG. 19A, the cutting unit 220 is caused to expand by only force acting radially outward which is received from the support portion 230. Therefore, a gap is less likely to occur between the strut 41 and the wires 231. If the linear motion shaft 250 is moved to the proximal side with respect to the drive shaft 240, as illustrated in FIG. 24, the interlock portion 320 which interlocks the proximal portion of the linear motion shaft 250 and the proximal portion of the drive shaft 240 with each other is extended, thereby maintaining a liquid-tight state. Accordingly, the physiological salt solution flowing into a portion between the linear motion shaft 250 and the drive shaft 240 does not leak out therefrom.

Then, the size of the cutting unit 220 and the support portion 230 can be optionally adjusted by using a rotation amount of the dial 360. Therefore, the cutting unit 220 can optionally adjust the size during the expansion to a desirable size, and thus can perform effective cutting.

When the dial 360 is rotated so as to expand the support portion 230 and the cutting unit 220, the X-ray fluoroscopy is used in order to expand the expansion diameter of the cutting unit 220 to be larger than the gap of the stenosed site S while the expansion diameter of the cutting unit 220 is compared with the gap of the stenosed site S. In this case, the outer diameter of the portion which expands most in the cutting unit 220 and the support portion 230 has a size between the minimum contraction state where both of these contract most and the maximum expansion state where both of these expand most.

Next, if the control unit 300 rotates the motor 96 by supplying the current to the motor 96, the driving force of the motor 96 is transmitted to the driven gear 61 from the drive gear 94, the drive shaft 240 interlocking with the driven gear 61 is rotated, and the cutting unit 220 and the support portion 230 which interlock with the drive shaft 240 are rotated. If the cutting unit 220 and the support portion 230 are rotated, the linear motion shaft 250 interlocking with the support portion 230 on the distal side is also rotated. In addition, the linear motion shaft 250 interlocks with the drive shaft 240 by the interlock portion 320 on the proximal side. Accordingly, the linear motion shaft 250 also receives the rotating force from the proximal side. Therefore, the linear motion shaft 250 becomes likely to rotate to follow the drive shaft 240 without any delay, and thus the linear motion shaft 250 can be prevented from being twisted. Then, the linear motion shaft 250 can be prevented from being twisted, it is not necessary to carry out work for twisting the linear motion shaft 250. The driving force can be effectively transmitted to the linear motion shaft 250, thereby enabling low torque driving. In addition, since the interlock portion 320 is located outside a body when manual skills are used, safety can be ensured even if the interlock portion 320 is damaged.

Since the drive shaft 240 is rotatably supported by the first bearing portion 331 and the second bearing portion 332, the drive shaft 240 can rotate smoothly. The first sealing portion 355 is in contact with the cover portion 242 disposed on the outer peripheral surface of the drive shaft 240 inside the first housing 351, and the drive shaft 240 is rotated so as to cause the cover portion 242 to slide on the first sealing portion 355. However, since the cover portion 242 is formed by using a low frictional material, the rotation of the drive shaft 240 is hardly hindered. In addition, the linear motion shaft 250 can rotate smoothly since the proximal portion is rotatably supported by the third bearing portion 341.

Next, in a state where the cutting unit 220 and the support portion 230 are rotated, as illustrated in FIG. 25B, the treatment device 210 is pushed to move forward. In this manner, the blade 47 formed in the cutting unit 220 and the convex portion 261 (refer to FIG. 21) formed in the distal tube 260 come into contact with the stenosed site S so as to cut stenosis substances. The debris D changed from the stenosis substances flows to the distal side (downstream side). The debris D flowing to the distal side enters the inside of the filter portion 111 located on the distal side, and is filtered and collected by the filter portion 111. In this manner, the debris D can be prevented from flowing to the peripheral blood vessel. Accordingly, a new stenosed site can be prevented from developing in the peripheral blood vessel.

Then, when the stenosed site S is cut, the support portion 230 protrudes radially outward between the struts 41. Accordingly, the support portion 230 having a lower influence on biological tissues than the strut 41 comes into contact with the biological tissues. Therefore, normal biological tissues can be prevented from being damaged by the edge portion of the strut 41, and thus, safety can be improved.

In addition, the distal end portion 221 of the cutting unit 220 is not fixed to the support portion 230 and the linear motion shaft 250, and when the expansion starts, the cutting portion 220 expands by using the force acting radially outward which is received from the support portion 230.

Accordingly, a gap is less likely to occur between the strut 41 and the wires 231. In this manner, the dropped hard debris D or stenosis substances are less likely to be interposed between the strut 41 and the wires 231. Therefore, since the strut 41 is not rolled up outward, the strut 41 can be prevented from being damaged or broken, and thus, normal biological tissues can be prevented from being damaged by the edge portion of the strut 41.

When the treatment device 210 is pushed to move forward, the treatment device 210 can be pulled out, after the stenosed site S is cut by pushing the cutting unit 220 to move forward, and before the cutting unit 220 completely passes the stenosed site S. Then, the cutting unit 220 is pushed gradually move forward to the stenosed site S by repeatedly pushing and pulling the treatment device 210, thereby enabling the stenosed site S to be cut little by little. In this manner, the cutting unit 220 can be prevented from being damaged or broken by preventing excessive force from acting on the cutting unit 220.

If excessive cutting resistance (resistance in the rotating direction) acts on the cutting unit 220, a change occurs in the current for driving the motor 96. The control unit 300 detects this change in the current. The control unit 300 specifies the cutting resistance based on the detected current. When the cutting resistance exceeds a preset threshold value, the control unit 300 stops the rotation of the motor 96. Then, the control unit 300 causes the monitor 401 to display that the cutting resistance exceeds the threshold value, and causes the speaker 402 to issue the notification by using sound.

In addition, if excessive pushing/pulling resistance (resistance in the axial direction) acts on the cutting unit 220, the excessive pushing/pulling resistance is detected by the pushing/pulling resistance measuring unit 310, and is notified to the control unit 300. When the pushing/pulling resistance exceeds a preset threshold value, the control unit 300 stops the rotation of the motor 96. Then, the control unit 300 causes the monitor 401 to display that the pushing/pulling resistance exceeds the threshold value, and causes the speaker 402 to issue the notification by using sound.

If the control unit 300 stops the motor 96 when detecting the excessive cutting resistance or pushing/pulling resistance occurring in the cutting unit 220, the control unit 300 can cause the cutting unit 220 to stop cutting before the cutting unit 220 is damaged or broken. After the rotation of the motor 96 is stopped, as illustrated in FIG. 26A, the treatment device 210 is pulled out therefrom, and the control unit 300 is operated so as to rotate the motor 96 again, thereby enabling the treatment device 210 to restart the cutting. When the cutting resistance or the pushing/pulling resistance exceeds the threshold value, the control unit 300 may decelerate the rotation speed instead of stopping the rotation of the motor 96. In addition, without stopping the rotation of the motor 96, the control unit 300 may cause the notification unit 400 to prompt a user to stop the motor 96.

As illustrated in FIG. 26B, after the cutting unit 220 passes the stenosed site S, the treatment device 210 is pulled out therefrom. As illustrated in FIG. 27A, the cutting unit 220 is moved to the proximal side of the stenosed site S, and the rotation of the drive shaft 240 is stopped. Next, the dial 360 is rotated again, and as illustrated in FIG. 27B, the cutting unit 220 is caused to expand further. Then, similarly to the above-described operation, the cutting unit 220 is rotated, and the treatment device 210 is repeatedly pushed and pulled. When the cutting resistance or the pushing/pulling resistance exceeds the threshold value, the control unit 300 stops the rotation. As illustrated in FIGS. 28A and 28B, the stenosed site S is cut little by little. After the cutting unit 220 passes the stenosed site S, the treatment device 210 is pulled out therefrom, the cutting unit 220 is moved to the proximal side of the stenosed site S, and the rotation of the drive shaft 240 is stopped. Then, the cutting unit 220 is caused to gradually expand, and the cutting unit 220 is repeatedly pushed to and pulled out from the stenosed site S so as to cut the stenosed site S. As described above, the stenosed site S is cut while the cutting unit 220 is caused to gradually expand. In this manner, the cutting unit 220 can be prevented from being damaged or broken by preventing the excessive force from acting on the cutting unit 220.

After the stenosed site S is completely cut by the cutting unit 220, the dial 360 is reversely rotated as compared to when the cutting unit 220 and the support portion 230 expand. In this manner, as illustrated in FIG. 16, the feed screw 361 is rotated, the moving base 370 is moved to the distal side, and the linear motion shaft 250 interlocking with the moving base 370 is moved to the distal side. If the linear motion shaft 250 is moved to the distal side, as illustrated in FIG. 15, the distal end portion 234 of the support portion 230 moves so as to be separated from the proximal end portion 235, thereby bringing the cutting unit 220 and the support portion 230 into a state of contracting radially inward. Next, if the first housing 351 is moved to the distal side with respect to the second housing 333, the outer sheath 270 is moved to the distal side. As illustrated in FIG. 29A, the cutting unit 220 and the support portion 230 are accommodated inside the outer sheath 270. Thereafter, the treatment device 210 is removed outward from a body via the guiding catheter 140.

Thereafter, as illustrated in FIG. 29B, the sheath 120 is inserted into the blood vessel via the guiding catheter 140, and the debris D inside the filter portion 111 is aspirated into the sheath 120. Then, the filter portion 111 is accommodated inside the sheath 120. Thereafter, the filter instrument 110 is removed therefrom together with the sheath 120. The guiding catheter 140 and the introducer sheath are removed therefrom, thereby finishing manual skills.

Then, while the manual skills are used, the treatment device 210 prevents the blood from flowing into the outer sheath 270, the drive shaft 240, the linear motion shaft 250, and the inner tube 280, since the physiological salt solution is always supplied to the treatment device 210 by the container bag 352. Accordingly, the blood is prevented from coagulating inside the treatment device 210. Therefore, operability of the treatment device 210 can be prevented from becoming poor due to coagulation of the blood. It is also possible to prevent coagulated substances from flowing into the blood vessel, thereby improving safety. In addition, since the blood can be prevented from flowing outward via the treatment device 210, the safety can be improved.

As described above, the medical device 200 according to the second embodiment is configured so that the drive shaft 240 is a tubular body, and further has the linear motion shaft 250 which is arranged inside the drive shaft 240, which is movable in the axial direction relative to the drive shaft 240, and which is rotatable together with the drive shaft 240. Then, the support portion 230 is expandable radially outward by receiving the force acting in the axial direction, which is generated by the relative movement of the drive shaft 240 and the linear motion shaft 250 in the axial direction. In the strut 41, the movement of the distal side in the axial direction with respect to the drive shaft 240 and the linear motion shaft 250 is not restricted. The strut 41 expands radially outward by being pressed due to the radially outward expansion of the support portion 230. Therefore, when the strut 41 is caused to expand, a gap is less likely to occur between the strut 41 and the support portion 230, and the stenosis substances or the debris are less likely to be interposed between the strut 41 and the support portion 230. Accordingly, the medical device 200 can prevent the strut 41 from being damaged, and can prevent normal biological tissues from being damaged by the edge portion of the strut 41.

In addition, the medical device 200 further has the inner tube 280 which is a tubular body arranged inside the drive shaft 240, and whose rotation is not restricted with respect to the drive shaft 240 and the linear motion shaft 250. Therefore, according to the medical device 200, even when the drive shaft 240 and the linear motion shaft 250 are rotated, the inner tube 280 is not rotated, and the rotating force does not act on the filter instrument 110 inserted into the inner tube 280 or the guidewire. For example, if the filter instrument 110 or the guidewire is directly inserted into a rotating tubular body, the filter instrument 110 or the guidewire slides on the inner wall surface of the tubular body, thereby causing abrasion, or causing a possibility that the rotated filter instrument 110 or the rotated guidewire may be less likely to be removed. In contrast, according to the medical device 200, the filter instrument 110 or the guidewire can be inserted into the inner tube 280, which is not rotated. Accordingly, the abrasion of the filter instrument 110 or the guidewire can be prevented, and the rotated filter instrument 110 or the rotated guidewire can be prevented from becoming less likely to be removed. In addition, if the tubular body is rotated, a fluid such as the blood or the like is likely to be drawn into the tubular body. However, since the inner tube 280 is not rotated, the blood is less likely to be drawn into the lumen 281 of the inner tube 280. Accordingly, it is possible to prevent operability from becoming poor by preventing the blood from coagulating inside the lumen 281. In addition, if the tubular body into which the filter instrument 110, the guidewire or the like is inserted is rotated, abrasion with the inner wall surface of the tubular body causes the filter instrument 110, the guidewire or the like to move in the axial direction. Consequently, in some cases, there is a possibility that the blood vessel may be damaged. However, according to the medical device 200, the inner tube 280 into which the filter instrument 110, the guidewire or the like is inserted is not rotated. Therefore, the blood vessel can be prevented from being damaged due to the movement of the filter instrument 110, the guidewire or the like in the axial direction.

In addition, according to the medical device 200, a portion of the strut 41 or the support portion 230 has the contrast portion configured to include an X-ray contrast material. Accordingly, the position or the expansion diameter of the strut 41 or the support portion 230 can be accurately recognized by using X-ray fluoroscopy, thereby further facilitating manual skills.

In addition, the medical device 200 further has the distal tube 260 which has a tubular shape and in which the multiple convex portions 261 are formed on the outer peripheral surface, on the further distal side from the strut 41. Accordingly, the distal tube 260 can also cut the stenosed site S, thereby enabling the stenosed site S to be cut quickly.

In addition, a treatment method (therapy method) is disclosed for cutting substances inside a body lumen. The treatment method is adopted by using a medical device including a drive shaft that is rotatable, at least one strut that rotatably interlocks with a distal side of the drive shaft, that extends along a rotation axis, and whose central portion is bent so as to be expandable radially outward, and a support portion that is rotatably driven by the drive shaft, that is formed in a mesh shape and a tubular shape while including multiple gaps, at least a portion of which is positioned on a radially inner side of the strut, and that is expandable radially outward by a central portion in a direction extending along the rotation axis being bent. The treatment method can include (i) a step of inserting the strut and the support portion which are in a contracted state into the body lumen, (ii) a step of detecting a size of a gap between the substances inside the body lumen, (iii) a step of expanding the strut and the support portion so as to be larger than the gap in the stenosed site on a further proximal side from the gap in the stenosed site, (iv) a step of cutting the stenosis substances by causing the drive shaft to rotate the strut and the support portion so as to be pressed into the gap in the stenosed site, (v) a step of contracting the strut and the support portion, and (vi) a step of removing the strut and the support portion from the inside of the body lumen. According to the treatment method configured as described above, it is possible to cut substances in a stenosed site after the strut and the support portion are caused to expand on the further proximal side from the stenosed site so as to have a suitable size which is larger than the gap in the stenosed site. Accordingly, the substances in the stenosed site can be effectively cut. The meaning of the stenosed site also includes an occluded site, and the occluded site is one form of the stenosed site.

In addition, according to the above-described treatment method, the step of expanding the strut and the support portion and the step of cutting the substances in the stenosed site may be repeated at least once while the strut and the support portion are caused to gradually expand. In this manner, the substances in the stenosed site can be cut little by little, thereby reducing load acting on the strut. Accordingly, the substances can be more reliably cut while the strut is prevented from being damaged or broken.

In addition, according to the above-described treatment method, in the step of expanding the strut and the support portion, the strut and the support portion may be caused to expand so as to have a size smaller than that in the maximum expansion state. For example, when the stenosed site is dilated by using a balloon, the balloon is brought into the preset maximum expansion state so as to dilate the stenosed site. However, according to this treatment method, the strut having a size smaller than that in the maximum expansion state can cut the substances in the stenosed site. Accordingly, it is easy to set desirable cutting conditions.

In addition, according to the above-described treatment method, in the step of detecting a gap size of the stenosed site, the gap size may be detected by using X-ray fluoroscopy to observe the contrast portion which is disposed in a portion of the strut or the support portion and which is configured to include an X-ray contrast material. In this manner, the position and the expansion diameter of the strut or the support portion can be accurately adjusted while the gap of the stenosed site is compared with the position and the expansion diameter by using X-ray fluoroscopy, thereby further facilitating manual skills.

In addition, the present disclosure also provides another treatment method (therapy method) for cutting substances inside a body lumen. The treatment method is adopted by using a medical device including a tubular drive shaft that is rotatable, a tubular outer sheath that can accommodate the drive shaft, at least one strut that rotatably interlocks with a distal side of the drive shaft, that extends along a rotation axis, and whose central portion is bent so as to be expandable radially outward, a linear motion shaft that is arranged inside the drive shaft, and that expands the strut by moving relative to the drive shaft in an axial direction, and a liquid supply unit that supplies liquid to any one of a portion between the outer sheath and the drive shaft and a portion between the drive shaft and the linear motion shaft. The treatment method can include (i) a step of inserting the strut in a contracted state into the body lumen, (ii) a step of expanding the strut by moving the linear motion shaft to the drive shaft, (iii) a step of cutting the substances inside the body lumen by causing the drive shaft to rotate the strut, (iv) a step of causing the liquid supply unit to supply the liquid to any one of the portion between the outer sheath and the drive shaft and the portion between the drive shaft and the linear motion shaft so that the liquid flows in a distal direction, in a state where the medical device is inserted into the body lumen, and (v) a step of contracting the strut and removing the strut from the inside of the body lumen. According to the treatment method configured as described above, the liquid flows in the distal direction through at least one portion between the outer sheath and the drive shaft, and between the drive shaft and the linear motion shaft. Accordingly, the blood becomes less likely to flow through at least one portion between the outer sheath and the drive shaft, and between the drive shaft and the linear motion shaft. Therefore, the blood is prevented from coagulating inside the treatment device, and relative movements are properly maintained between the respective tubular bodies. Accordingly, it is possible to prevent operability from becoming poor. In addition, since the blood can be prevented from flowing outward via the medical device, safety can be improved.

In addition, the present disclosure also provides further another treatment method (therapy method) for cutting substances inside a body lumen. The treatment method is adopted by using a medical device including a drive shaft that is rotatable, at least one strut that rotatably interlocks with a distal side of the drive shaft, that extends along a rotation axis, and whose central portion is bent so as to be expandable radially outward, a support portion that is rotatably driven by the drive shaft, that is formed in a mesh shape and a tubular shape while including multiple gaps, at least a portion of which is positioned on a radially inner side of the strut, and that is expandable radially outward by a central portion in a direction extending along the rotation axis being bent, and a detection unit that detects resistance including at least any one of rotating direction resistance and axial direction resistance which act on the strut. The treatment method can include (i) a step of inserting the strut and the support portion which are in a contracted state into the body lumen, (ii) a step of expanding the strut and the support portion, (iii) a step of gradually cutting the substances while repeatedly pushing and pulling the substances inside the body lumen by causing the drive shaft to rotate the strut and the support portion, (iv) a step of causing the detection unit to detect the resistance, (v) a step of stopping the rotation of the strut and the support portion when the resistance exceeds a preset threshold value or giving a notification that the resistance exceeds the threshold value, and (vi) a step of contracting the strut and the support portion and removing the strut and the support portion from the inside of the body lumen. According to the treatment method configured as described above, when the resistance exceeds the preset threshold value, the rotation of the strut and the support portion is stopped, or the fact that the resistance exceeds the preset threshold value is notified. Accordingly, when excessive resistance acts on the strut, measures can be taken in order to prevent the strut from being damaged or broken, thereby improving safety.

In addition, the above-described treatment method may further include a step of contracting the strut and the support portion or moving the strut and the support portion along the axial direction, after the step of stopping the rotation of the strut and the support portion or giving the notification that the resistance exceeds the threshold value. In this manner, when the strut restarts the cutting, the resistance acting on the strut is reduced. Accordingly, the strut can be prevented from being damaged or broken.

In addition, according to the above-described treatment method, in the step of decreasing the diameter of the strut and the support portion or moving the strut and the support portion along the axial direction, the strut and the support portion may be moved in the proximal direction so as to be separated from the substances. In this manner, when the cutting is restarted, the strut and the support portion can be pushed to the substances from the proximal side, thereby enabling the substances to be cut effectively.

Without being limited to the above-described embodiments, the present invention can be modified in various ways by those skilled in the art, within the technical idea of the present invention. For example, according to the first embodiment, the blade 47 is formed on only the distal side of the strut 41. However, the blade 47 may be formed on the proximal side of the strut 41, or may be formed on both the distal side and the proximal side.

Figure 30:
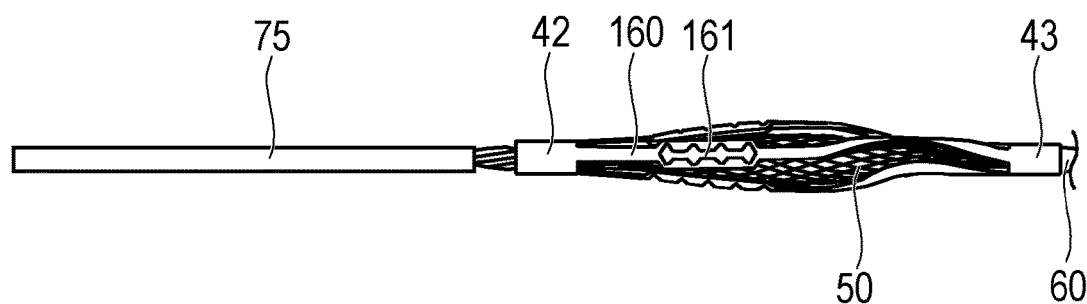
FIG. 30 is a plan view illustrating a modification example of the medical device according to the first embodiment.

In addition, according to the first embodiment, one strut 41 has the multiple opening portions 45 formed therein. However, as illustrated in FIG. 30, one strut 160 may have only one opening portion 161 which is elongated in the extending direction of the strut 160, and the inner edge portion of the opening 161 may serve as a blade. The same reference numerals are given to elements having the same function as that in the above-described embodiments, and description thereof will be omitted.

In addition, according to the first embodiment, the inner edge portion of the opening 45 of the strut 41 serves as the blade 47. However, an outside edge portion of the strut may serve as a blade.

In addition, without being limited to the blood vessel, the body lumen into which the medical device 10 is inserted may include the vascular, the urinary tract, the biliary tract, the fallopian tube, the hepatic duct and the like.

Figure 31:
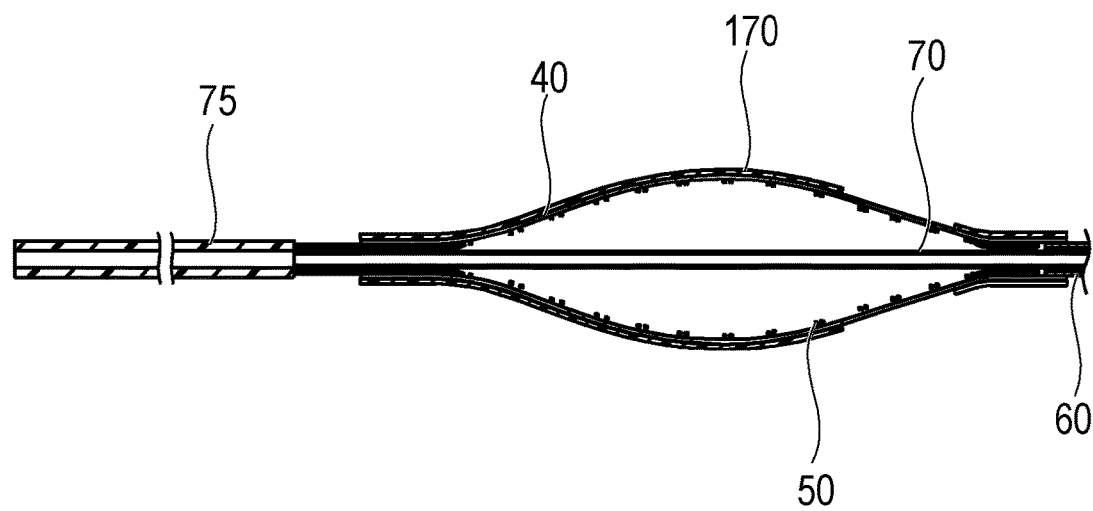
FIG. 31 is a cross-sectional view illustrating another modification example of the medical device according to the first embodiment.

In addition, at least any one of the cutting unit 40 and the support portion 50 may be covered with a cover layer 170 configured to include a hydrophilic material, as in another modification example according to the first embodiment, which is illustrated in FIG. 31. According to this configuration, at least any one of the cutting unit 40 and the support portion 50 is likely to slide between biological tissues. Accordingly, safety can be improved by preventing normal biological tissues from being damaged. The same reference numerals are given to elements having the same function as that in the above-described embodiments, and description thereof will be omitted.

For example, the hydrophilic materials include cellulose-based polymeric substances, polyethylene oxide-based polymeric substances, maleic anhydride-based polymeric substances (for example, maleic anhydride copolymer such as methyl vinyl ether-maleic anhydride copolymers), acrylamide-based polymeric substances (for example, polyacrylamide, and block copolymer of polyglycidyl methacrylate-dimethylacrylamide (PGMA-DMAA)), water-soluble nylon, polyvinyl alcohol, polyvinyl pyrrolidone, and the like.

In addition, the blade formed in the strut may be a polishing material such as diamond particles or the like which are attached to the outer surface of the strut.

In addition, according to the first embodiment, the support portion 50 is arranged on the radially inner side of the strut 41. However, a portion of the wire configuring the support portion may be arranged outside the strut. According to this configuration, a portion of the strut which is not intended to come into contact with biological tissues is covered with the wire. Therefore, it is possible to minimize damage to normal biological tissues.

In addition, according to the above-described first embodiment, the cutting unit 40 and the support portion 50 can be caused to expand so as to have any desired size by the operation in the operation unit 90. However, a configuration may be adopted in which the cutting unit 40 and the support portion 50 cannot expand so as to have any desired size. Alternatively, a structure may be adopted in which the cutting unit and the support portion expand by using self-restoring force.

In addition, according to the above-described first embodiment, the support portion 50 is formed by braiding the multiple wires 51. However, the support portion may be formed into a reticular shape by forming multiple openings in a single member.

In addition, according to the above-described first embodiment, the feed screw mechanism is employed in order to move the linear motion shaft 70. However, a structure is not limited thereto as long as the linear motion shaft 70 can be moved.

In addition, according to the above-described first embodiment, the motor 96 is employed in order to rotate the drive shaft 60. However, without being limited thereto, the drive source may be a gas turbine, which is rotated by using high pressure gas such as nitrogen gas or the like, for example.

In addition, at least a portion of the cutting unit and the support portion may be formed so that the material thereof includes the X-ray contrast material. In this manner, it is possible to accurately recognize the position by using X-ray fluoroscopy, thereby further facilitating manual skills. For example, the X-ray contrast materials preferably include gold, platinum, platinum-iridium alloy, silver, stainless steel, molybdenum, tungsten, tantalum, palladium, alloy thereof or the like.

Figure 32:
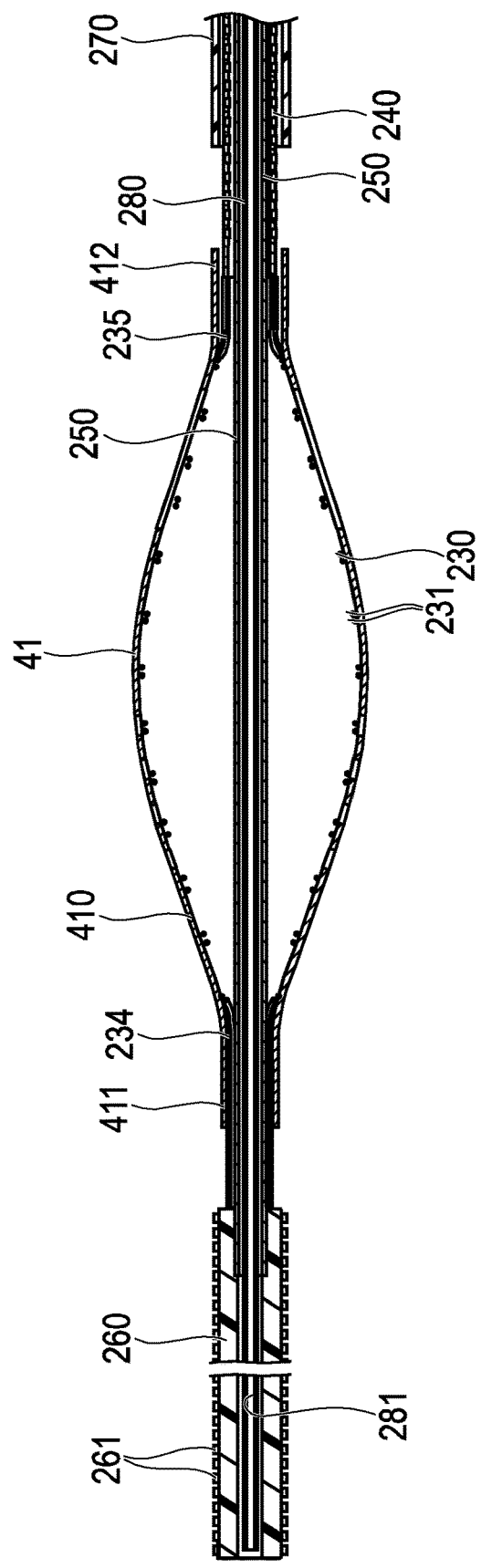
FIG. 32 is a longitudinal sectional view illustrating a modification example of the medical device according to the second embodiment.

In addition, according to a modification example of the second embodiment, which is illustrated in FIG. 32, a distal end portion 411 of a cutting unit 410 may be fixed to the distal end portion 234 of the support portion 230, and a proximal end portion 412 of the cutting unit 410 may be fixed to the proximal end portion 235 of the support portion 230 and the drive shaft 240. Accordingly, the proximal end portion 412 of the cutting unit 410 is movable in the axial direction relative to the proximal end portion 235 of the support portion 230 and the drive shaft 240. The proximal end portion 235 of the support portion 230 is fixed to the drive shaft 240, and the distal end portion 234 of the support portion 230 is fixed to the linear motion shaft 250. Even in this configuration, the distal end portion 234 and the proximal end portion 235 of the support portion 230 are moved close to each other. In this manner, force acting in the axial direction does not act between the distal end portion 411 and the proximal end portion 412 of the cutting unit 410. The strut 41 of the cutting unit 410 can be caused to expand by only force acting radially outward which is received from the support portion 230. The same reference numerals are given to elements having the same function as that in the above-described embodiments, and description thereof will be omitted.

Figure 33:
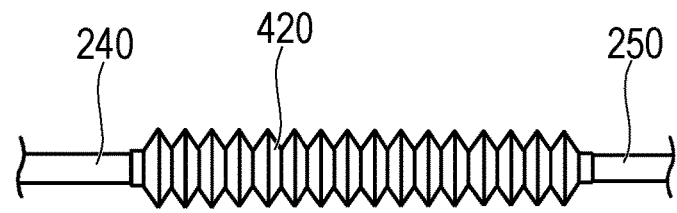
FIG. 33 is a plan view illustrating another modification example of the medical device according to the second embodiment.

In addition, as in another modification example of the second embodiment, which is illustrated in FIG. 33, an expandable and contractible interlock portion 420 which interlocks the proximal portion of the linear motion shaft 250 and the proximal portion of the drive shaft 240 with each other may be formed into a bellows shape. If the interlock portion 420 has the bellows shape, the interlock portion 420 is likely to expand and contract in the axial direction. The same reference numerals are given to elements having the same function as that in the above-described embodiments, and description thereof will be omitted.

Figure 34:
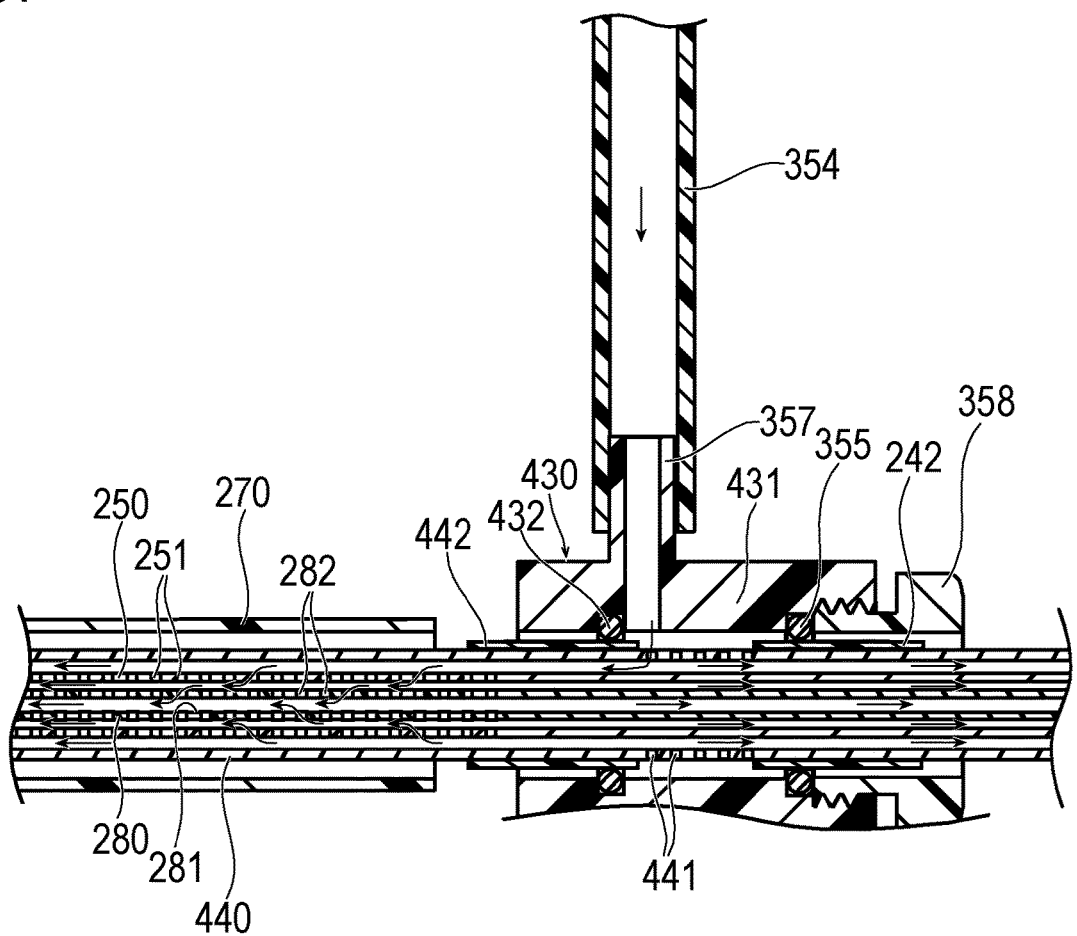
FIG. 34 is a cross-sectional view illustrating further another modification example of the medical device according to the second embodiment.

In addition, as in further another modification example of the second embodiment, which is illustrated in FIG. 34, the outer sheath 270 may not interlock with a first housing 431 of a liquid supply unit 430, and a third sealing portion 432 may be disposed on the further distal side from the port portion 357 disposed in the first housing 431. Then, in a drive shaft 440, a hole portion 441 is formed between the first sealing portion 355 and the third sealing portion 432. The outer surface of the drive shaft 440 is covered with a second cover portion 442 for decreasing a frictional force by coming into slidable contact with the third sealing portion 432. According to this configuration, without supplying the physiological salt solution from the container bag 352 to a portion between the outer sheath 270 and the drive shaft 440, the physiological salt solution can be caused to flow into a portion between the drive shaft 440 and the linear motion shaft 250 via the hole portion 441. The physiological salt solution flowing into the drive shaft 440 can flow into the linear motion shaft 250 after passing through the hole portion 251 of the linear motion shaft 250. The physiological salt solution flowing into the linear motion shaft 250 can flow into the lumen 281 of the inner tube 280 after passing through the hole portion 282 of the inner tube 280. The same reference numerals are given to elements having the same function as that in the above-described embodiments, and description thereof will be omitted.

FIG. 35A is a longitudinal sectional view illustrating the distal end portion of the treatment device 20 according to an exemplary embodiment. As shown in FIG. 35A, the treatment device 20 can include a cutting unit (or cutting part) 40 which is expandable and contractible radially outward, a drive shaft 60 which rotates the cutting unit 40, a linear motion shaft (or elongated tube) 70 which adjusts a deformation amount of the cutting unit 40, and a tip member 500 (or distal tube), which is connected with a distal side of the linear motion shaft 70. In accordance with an exemplary embodiment, the cutting unit 40 and the support portion (or expanding part) 50 (FIG. 35B) form a treatment member 502.

In accordance with an exemplary embodiment, as shown in FIG. 35A, a bearing member 510 is placed distal to the cutting unit 40 and the support portion 50 which can help separate the linear motion shaft from rotating of the cutting unit 40 and the drive shaft 60. This can help prevent a lumen of the blood vessel from being injured or damaged by the rotating guidewire (not show) inserted within the elongated tube or lumen 72 of the linear shaft 70. In addition, the bearing member 510 can help with the removal of the guidewire (not shown) from the treatment device 20. The bearing member 510 can also be used for reducing a resistance between a distal side of the treatment member 502 and the elongated tube or lumen 72 of the linear shaft 70.

FIG. 35B is a longitudinal sectional view illustrating the distal end portion of the treatment device 20 according to an exemplary embodiment. As shown in FIG. 35B, the treatment device 20 can include the cutting unit 40 which is expandable and contractible radially outward, the support portion 50 which supports the cutting unit 40, the drive shaft 60 which rotates the cutting unit 40, the linear motion shaft 70 which adjusts a deformation amount of the cutting unit 40, and a tip member 500 (or distal tube), which is connected to a distal end of the linear shaft 70.

FIG. 36 is a longitudinal sectional view illustrating the distal end portion of the treatment device 20 according to an exemplary embodiment in an expanded state. As shown in FIG. 36, in an expanded state (or expansion state), as disclosed above, the support portion 50 is expandable radially outward by receiving force acting in the axial direction, which is generated by the relative movement of the drive shaft 60 and the linear motion shaft (or elongated tube) 70 in the axial direction.

FIG. 37A is a sectional view illustrating the distal end portion of the treatment device 20 according to an exemplary embodiment. As shown in FIG. 37A, a distal side of the support portion (or expanding part) 50 is connected to an outer tube 514 of the bearing member 510. In accordance with an exemplary embodiment, the bearing member 510 comprises an inner tube 512, the outer tube 514, and a ring member (or bearing) 516 sandwiched between the inner tube 512 and the outer tube 514. The inner tube 512 can be connected to the linear shaft (or elongated tube) 70 and the outer tube 514 can be connected to the expandable support portion 50. The ring member 516 can be any suitable bearing, for example, a rolling-element bearing a ball bearing and/or a roller bearing.

In accordance with an exemplary embodiment, an inner support member (or reinforcement member) 518 can be arranged between the bearing member 510 and the linear motion shaft 70, and arranged between the linear motion shaft 70 and the tip member 500. The inner support member (or reinforcement member) 518 preferably extends from a proximal side of the bearing member 510 to a distal side of the bearing member 510. In addition, an outer support member 519 can be provided can be arranged on an outer portion of the bearing member 510. The outer support member 519 can be connected to the outer portion of the bearing member 510 and an outer portion a support housing 530, which is spaced apart from the linear motion shaft 70. As shown, the bearing member 510 can be sandwiched between the inner support member 518 and the outer support member 519. In accordance with an exemplary embodiment, the inner support member 518, the bearing member 510, and the outer support member 519 can form a tubular support member 540.

In accordance with an exemplary embodiment, on the distal side of the treatment member 502, a gap or space 520 is arranged between an inner side 522 of the support portion 50 and an outer side 524 of the linear motion shaft (or elongated tube) 70. As disclosed, the support portion 50 that is rotatably driven by the drive shaft 60 (not shown in FIG. 37A), and can be formed, for example, in a mesh shape and a tubular shape while including multiple gaps, at least a portion of which is positioned on a radially inner side of at least one strut (not shown), and that is expandable radially outward by a central portion in a direction extending along the rotation axis being bent.

As shown in FIG. 37A, on the distal end, the support portion 50 can be housed in a support housing 530, which is spaced apart from the linear motion shaft 70. In accordance with an exemplary embodiment, a distal side of the support housing 530 is connected to a tubular support member 540, which includes the bearing member 510. The support housing 530 can be configured to receive a distal end of support portion 50. In accordance with an exemplary embodiment, the tubular support member 540 can extend from a distal side of the support housing 530 to the bearing member 510.

FIG. 37B is a sectional view illustrating the distal end portion of the treatment device according to an exemplary embodiment. As shown in FIG. 37B, in accordance with an exemplary embodiment, a gap or space 560 is arranged between an inner side 562 of the support portion 50 and an outer side 564 of the linear motion shaft (or elongated tube) 70 on the proximal side of the treatment member 502. In addition, the support portion (or expanding part) 50 is connected to an inner edge 542 of the cutting unit (or cutting part) 40 on the proximal side of the treatment member 502.

FIG. 38A is a longitudinal sectional view illustrating the distal end portion of the treatment device according to an exemplary embodiment. As shown in FIG. 38A, the treatment device 20 can include a cutting unit 40 which is expandable and contractible radially outward, a drive shaft 60 which rotates the cutting unit 40, a linear motion shaft 70 which adjusts a deformation amount of the cutting unit 40, and a tip member 500 (or distal tube), which is connected with a distal side of the linear shaft 70. The cutting unit 40 and the support portion 50, which supports the cutting unit 40 form the treatment member 502.

FIG. 38B is a longitudinal sectional view illustrating the distal end portion of the treatment device 20 according to an exemplary embodiment in an expanded state. As shown in FIG. 38B, in an expanded state (or expansion state), as disclosed above, the support portion 50 is expandable radially outward by receiving force acting in the axial direction, which is generated by the relative movement of the drive shaft 60 and the linear motion shaft 70 in the axial direction.

Figure 39:
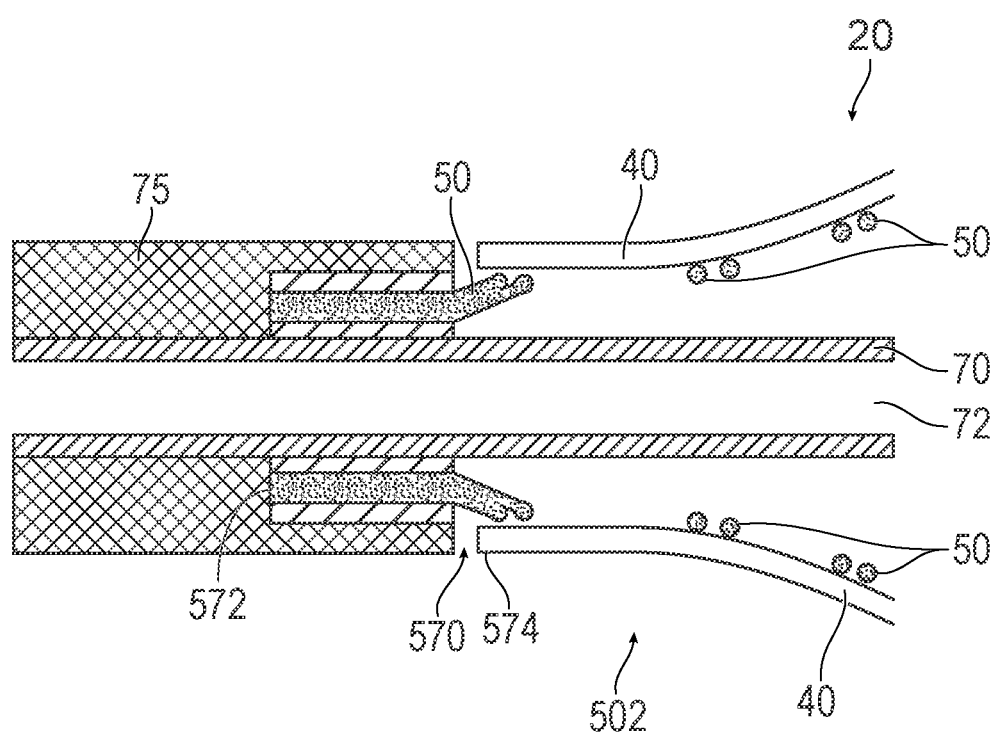
FIG. 39 is a sectional view illustrating the distal end portion of the treatment device according to an exemplary embodiment.

FIG. 39 is a sectional view illustrating the distal end portion of the treatment device 20 according to an exemplary embodiment. In accordance with an exemplary embodiment, a distal end 574 of the cutting unit 40 is spaced apart radially from a distal end 572 of the support member (or expanding part) 50 forming a gap or space 570. As shown in FIG. 39, a distal end 572 of the support portion 50 is placed distal to a distal end 574 of the cutting unit 40 of the treatment unit 502, which can help support radial forces for the cutting unit 40. In addition by spacing the distal end 572 of the support member 50 from a distal end 574 of the cutting unit 40, damage to and/or broken struts 41 (FIG. 4) on the cutting unit 40 can be avoided. In accordance with an exemplary embodiment, the support portion 50 extends distally into the distal tube 75. In accordance with an exemplary embodiment, the distal tube 75 can be fixed to a distal side of the linear motion shaft 70.

A treatment method is disclosed for cutting substances inside a body lumen by using a medical device including a rotatable tubular drive shaft 60, an expanding part 50 connected to a distal side of the drive shaft 6, a cutting part 40 covering the expanding part 50, and an elongated tube 70 extending through the drive shaft 60 and connected to the expanding part 50, wherein a distal end of the expanding part 50 is placed distal to a distal end of the cutting part 40, and wherein the distal end of the cutting part 40 is spaced apart radially from the distal end of the expanding part 50. The treatment method can include inserting the cutting part 40 and the expanding part 50 which are in a contracted state into the body lumen; detecting a size of a gap between the substances inside the body lumen; expanding the cutting part 40 and the expanding part 50 so as to be larger than the gap between the substances on a further proximal side from the gap between the substances; and cutting the substances by causing the drive shaft 60 to rotate the cutting part 40 and the expanding part 50 so as to be pressed into the gap between the substances.

The detailed description above describes medical device and treatment method. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for cutting substances inside a body lumen, the medical device comprising:
   an operation unit;
   a tubular drive shaft configured to extend in an axial direction, the tubular drive shaft having a lumen that extends from a proximal side to a distal end of the tubular drive shaft, the proximal side of the tubular drive shaft being connected to a motor or a drive gear and wherein the tubular drive shaft is configured to be driven and rotatable around the axial direction by the motor or the drive gear;
   a cutting part configured to be connected to the tubular drive shaft, and wherein the cutting part is configured to rotate around the axial direction in correspondence with the rotation of the tubular drive shaft;
   an elongated tube configured to extend in the axial direction and configured to penetrate through the lumen of the tubular drive shaft without being fixed to both the tubular drive shaft and the cutting part, the elongated tube having a lumen extending in the axial direction and configured to receive an insertable and removable guide wire, and wherein a proximal end of the elongated tube is located proximal to a proximal end of the motor or the drive gear;
   an outer sheath configured to accommodate the tubular drive shaft, the outer sheath being configured to be connected to the operation unit, and wherein the operation unit includes the motor or the drive gear;
   the proximal end of the elongated tube being located in proximity to a proximal end of the operation unit, and a proximal portion of the elongated tube is held to the proximal end of the operation unit by a proximal fixing portion arranged on an inner surface of a through-hole of the operation unit, the proximal fixing portion located between an outer surface of the proximal end of the elongated tube and the inner surface of the through-hole of the operation unit, and wherein the proximal fixing portion includes an opening in communication with an opening of the elongated tube;
   the through-hole of the operation unit being located proximal to the proximal end of the motor or the drive gear; and
   wherein the through-hole of the operation unit is placed in a proximal surface of the operation unit and the through-hole of the operation unit has a tapered portion.

2. The medical device according to claim 1, wherein a distal end of the elongated tube is placed distal to the distal end of the tubular drive shaft.

3. The medical device according to claim 1, further comprising:
   a bearing member configured to be placed on an outer surface of the elongated tube.

4. The medical device according to claim 3, wherein the bearing member is a ring member, a ball bearing, a rolling-element bearing, or a roller bearing.

5. The medical device according to claim 1, wherein a distal end of the elongated tube is placed in a vicinity to a distal end of the cutting part.

6. The medical device according to claim 1, wherein the elongated tube does not rotate with the tubular drive shaft.

7. The medical device according to claim 1, wherein the proximal fixing portion is a bolt-shaped member, which can be twisted and screwed into a screw groove formed in the through-hole of the operation unit.

8. The medical device according to claim 1, wherein the operation unit has a concave portion configured to receive the proximal fixing portion.

9. The medical device according to claim 8, wherein the proximal fixing portion is configured to be twisted into the concave portion of the operation unit, thereby deforming a sealing portion accommodated in the concave portion of the operation unit and surrounding the elongated tube.

10. The medical device according to claim 1, wherein the proximal fixing portion is configured to maintain a liquid-tight state between the operation unit and the elongated tube.

11. The medical device according to claim 1, wherein the operation unit is configured to be rotatable by rotating an outer peripheral surface of the operation unit.

12. The medical device according to claim 1, wherein the operation unit includes a discharge hole configured to discharge internal air during priming of the operation unit.

13. The medical device according to claim 12, further comprising:
   a stopper configured to open and close the discharge hole in the operation unit.

14. A medical device for cutting substances inside a body lumen, the medical device comprising:
   an operation unit;
   a tubular drive shaft configured to extend in an axial direction, the tubular drive shaft having a lumen that extends from a proximal side to a distal end of the tubular drive shaft, the proximal side of the tubular drive shaft being connected to a motor or a drive gear and wherein the tubular drive shaft is configured to be driven and rotatable around the axial direction by the motor or the drive gear;
   a cutting part configured to be connected to the tubular drive shaft, and wherein the cutting part is configured to rotate around the axial direction in correspondence with the rotation of the tubular drive shaft;
   an elongated tube configured to extend in the axial direction and configured to penetrate through the lumen of the tubular drive shaft without being fixed to both the tubular drive shaft and the cutting part, the elongated tube having a lumen extending in the axial direction and configured to receive an insertable and removable guide wire, and wherein a proximal end of the elongated tube is located proximal to a proximal end of the motor or the drive gear;
   an outer sheath configured to accommodate the tubular drive shaft, the outer sheath being configured to be connected to the operation unit, and wherein the operation unit includes the motor or the drive gear;
   the proximal end of the elongated tube being located in proximity to a proximal end of the operation unit, and a proximal portion of the elongated tube is held to the proximal end of the operation unit by a proximal fixing portion arranged on an inner surface of a through-hole of the operation unit, the proximal fixing portion located between an outer surface of the proximal end of the elongated tube and the inner surface of the through-hole of the operation unit, and wherein the proximal fixing portion includes an opening in communication with an opening of the elongated tube; and wherein the operation unit has a concave portion configured to receive the proximal fixing portion.

15. The medical device according to claim 14, wherein a distal end of the elongated tube is placed distal to the distal end of the tubular drive shaft.

16. The medical device according to claim 14, further comprising:
a bearing member configured to be placed on an outer surface of the elongated tube.

17. The medical device according to claim 16, wherein the bearing member is a ring member, a ball bearing, a rolling-element bearing, or a roller bearing.

18. The medical device according to claim 14, wherein a distal end of the elongated tube is placed in a vicinity to a distal end of the cutting part, and the elongated tube does not rotate with the tubular drive shaft.

19. The medical device according to claim 14, wherein the proximal fixing portion is a bolt-shaped member, which can be twisted and screwed into a screw groove formed in the through-hole of the operation unit.

20. The medical device according to claim 14, wherein the proximal fixing portion is configured to be twisted into the concave portion of the operation unit, thereby deforming a sealing portion accommodated in the concave portion of the operation unit and surrounding the elongated tube.

21. The medical device according to claim 14, wherein
the operation unit includes a discharge hole configured to discharge internal air during priming of the operation unit, and
a stopper configured to open and close the discharge hole in the operation unit.

* * * * *